US008673269B2

(12) United States Patent
Latham

(10) Patent No.: US 8,673,269 B2
(45) Date of Patent: Mar. 18, 2014

(54) HALOGENATED PHENOLS FOR DIAGNOSTICS, ANTIOXIDANT PROTECTION AND DRUG DELIVERY

(76) Inventor: Keith R. Latham, Abingdon, VA (US)

( * ) Notice: Subject to any disclaimer, the term of this patent is extended or adjusted under 35 U.S.C. 154(b) by 0 days.

(21) Appl. No.: 13/548,337

(22) Filed: Jul. 13, 2012

(65) Prior Publication Data

US 2013/0022549 A1 Jan. 24, 2013

Related U.S. Application Data

(60) Provisional application No. 61/507,670, filed on Jul. 14, 2011.

(51) Int. Cl.
*A61K 49/04* (2006.01)
*A61B 8/00* (2006.01)
(52) U.S. Cl.
USPC ............................ 424/9.44; 424/9.45; 424/9.6
(58) Field of Classification Search
USPC ........................................ 424/9.44, 9.45, 9.6
See application file for complete search history.

(56) References Cited

U.S. PATENT DOCUMENTS

| 5,576,138 | A | 11/1996 | Ando |
| 5,607,691 | A | 3/1997 | Hale |
| 6,265,621 | B1 | 7/2001 | Komori |
| 2004/0116391 | A1 | 6/2004 | Piccariello |
| 2005/0272076 | A1 | 12/2005 | Stengele |
| 2006/0193789 | A1 | 8/2006 | Tamarkin |
| 2006/0211697 | A1 | 9/2006 | Huang |
| 2008/0287774 | A1 | 11/2008 | Katz-Brull |

FOREIGN PATENT DOCUMENTS

| EP | 1268396 | 7/2005 |
| WO | 2007/059039 A1 | 5/2007 |

OTHER PUBLICATIONS

James et al. Applied and Environmental Microbiology vol. 62 No. 10 pp. 3868-3870, publication date: 1996.*
International Search Report (ISR) and Written Opinion for PCT/US12/46725.
International Search Report (ISR) and Written Opinion for PCT/US12/46725, Publication Date: Mar. 7, 2013.

(Continued)

*Primary Examiner* — Richard Schnizer
*Assistant Examiner* — Katherine Peebles

(57) ABSTRACT

The present invention relates to a composition and method for the detection of a detectable product formed from a compound of the present invention in the body of an individual. The detectable product may include a halide or a benzenetriol-based or benzenetetrol-based product of a dehalogenation reaction in the presence of FROS. In many embodiments, an indigo-like product formed from an indigogenic compound of the present invention may also be a detectable product for diagnostic purposes. This indigo-like product may have a higher residence time in tissues where it is formed, thus providing a detectable product localized to sites of high FROS. An indigogenic compound containing one or more radioactive isotopes is further provided for therapeutic purposes.

27 Claims, 27 Drawing Sheets (Formula 29)

(Indigo-like compound)

(Benzenetriol)

(56) References Cited

OTHER PUBLICATIONS

Sellitti, D.F. et al., "Effect of 3,5,3'-Triiodo-L-thyronine on the Incidence and Growth Kinetics of Spontaneous Mammary Tumors in C3H/HeN Mice," Cancer Research, 41:5015-19 (1981).

Salamonczyk, G.M. et al., Tetrahedron Letters, 38(40):6965-6968 (1997).

Leonard, J. et al., The Thyroid, Lippincott-Raven (Braverman, L.E. and Utiger, R.D., Eds.), pp. 125-161 (1996).

Holt, S.J., "General Cytochemical Methods," J.F. Danielli, Ed., Academic Press, New York, NY, p. 375 (1958).

Hong et al., "Identification of Electrical Degradation Products of 4-Chlorophenol in Water," Analytical Sciences, 19:537-542 (Apr. 2003).

ChenZuo, "Studies on the Synthesis and Antimicrobial Activities of Brominated Dihydroxy Nitro Diphenyl Ethers," Master's Thesis, Sichuan University (2007) (Summary).

Office Action for U.S. Appl. No. 13/548,352 (mailed on Oct. 7, 2013).

Office Action for U.S. Appl. No. 13/548,358 (mailed on Oct. 16, 2013).

* cited by examiner (Formula 6)

(Benzenetetrol product)    (drug 1)

(Formula 7)

(Formula 7)

(Benzenetriol product)

(Compound 8)

(dopamine)

(Formula 26)

(Formula 29)

(Indigo-like compound)

(Benzenetriol)

HALOGENATED PHENOLS FOR DIAGNOSTICS, ANTIOXIDANT PROTECTION AND DRUG DELIVERY

CROSS-REFERENCE TO RELATED APPLICATIONS

This application claims the benefit of priority to U.S. Provisional Patent Application No. 61/507,670, entitled "Halogenated Phenol Ethers for Diagnostics and Drug Delivery," filed on Jul. 14, 2011, the entire contents and disclosure of which are incorporated herein by reference.

BACKGROUND

1. Field of the Invention

The present invention relates generally to compositions and methods for detecting elevated levels of oxidative species and/or free radicals in the body of an individual, which may be characteristic of inflammation and/or disease.

2. Related Art

The presence of elevated levels of free radicals and/or oxidative species (FROS) in the body of an individual may be an indicator of abnormal conditions or physiology that may be associated with injury, inflammation and/or disease. These reactive FROS can be detrimental and cause damage to cells and tissues, including genetic mutations, which may ultimately contribute to aging and disease. Immunological and inflammatory responses also generate FROS, which is partly utilized to fight infection. Thus, measuring the FROS load in the body of an individual, as well as specific sites of FROS generation, may provide useful information for diagnosis and treatment of an individual and serve as an indicator of inflammation and/or disease. Currently, C-reactive protein (CRP) is one approach used for measuring the level of inflammation in the body.

There is a need in the art for the development of new and improved techniques and compositions for the measurement and/or localization of high levels of FROS in the body of an individual, which may be associated with disease and/or inflammation.

SUMMARY

According to a first broad aspect of the present invention, indigogenic compounds are provided as shown, for example, in FIGS. 28 and 29. These indigogenic compounds may contain one or more halogens on the benzene ring of its idolyl portion, which may impart color and/or radiographic properties to an indigo-like product formed from the indigogenic compounds in the body of an individual in the presence of FROS, which may be an indication of inflammation or disease. The indigo-like product may be detected in situ in the body of the individual due to the residence time of the product formed or in a sample taken from the individual. Methods of administering and detecting the same are further provided.

According to a second broad aspect of the present invention, compositions and methods are provided for compounds of the present invention as shown, for example, in FIGS. 1-25 and 28-29, to form a detectable benzenetriol-based and/or benzenetetrol-based product that may be detected in a sample as a measure of FROS levels, which may indicate inflammation or disease. A halide product, such as iodide, of the dehalogenation reaction may also be detected in a sample taken from an individual formed from any of the compounds of the present invention as shown in FIGS. 1-29 after administering the composition or compound to the individual.

According to a third broad aspect of the present invention, indigogenic compounds containing one or more radioactive isotopes are provided as shown, for example, in FIG. 28. Such radioactive indigogenic compounds may be administered to an individual for the treatment of disease, such as cancer. Due to the indigo-like product having residence time in the tissue of its formation, these radioactive indigogenic compounds may be used for targeted delivery of the radioactive dose to selectively irradiate the diseased tissue. Methods of administering the same are further provided.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION

Definitions

Figure 1:
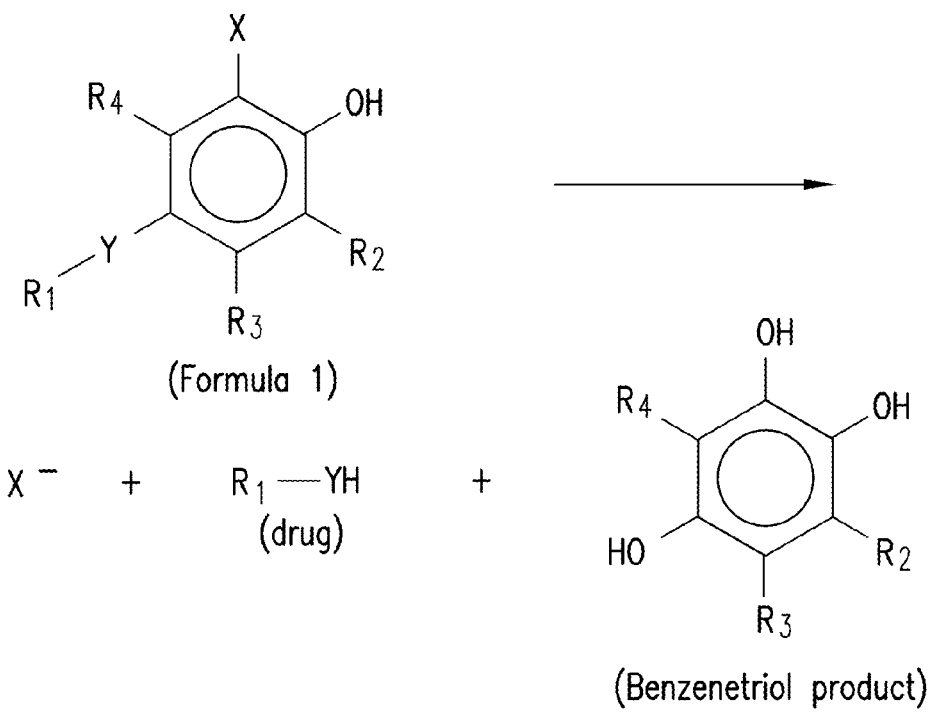
FIG. 1 is a diagram of a dehalogenation and cleavage reaction according to formula embodiments of the present invention with an ether or thioether linkage.

Where the definition of terms departs from the commonly used meaning of the term, applicant intends to utilize the definitions provided below, unless specifically indicated.

For purposes of the present invention, the term "halogenated phenol ring" refers to at least a portion of an arene molecule or compound having a benzene ring and a hydroxyl group and a halogen as substituents bonded to adjacent carbons of the benzene ring.

For purposes of the present invention, the terms "arene" or "arenes" refer to organic molecules or compounds based on the aromatic benzene ring as a structural unit.

For purposes of the present invention, the term "linkage" refers to a chemical linkage or bond(s) of a starting compound that connects a halogenated phenol ring to a compound, such as a drug compound. As described further herein, the "linkage" may be an ether linkage, thioether linkage, nitrogen linkage, an internal nitrogen linkage, a carbonyl linkage, a sulfinyl linkage, a metal linkage or possibly a C—C bond. According to some embodiments, this linkage is cleaved or broken during or following the dehalogenation reaction involving the starting compound.

For purposes of the present invention, the terms "ether linkage," "ether group," and "ether linked" refer to a functional group of a compound, such as a starting compound of the present invention, consisting of an oxygen atom singly bonded to two carbons of the compound (i.e., R—O—R'). For example, an "ether linkage" may join a halogenated phenol ring (R) to a core structure (R') of a compound.

For purposes of the present invention, the terms "thioether linkage," "thioether group," and "thioether linked" refer to a functional group of a compound, such as a starting compound of the present invention, consisting of an sulfur atom singly bonded to two carbons of the compound (i.e., R—S—R'). For example, a "thioether linkage" may join a halogenated phenol ring (R) to a core structure (R') of a compound.

For purposes of the present invention, the terms "carbonyl linkage," "carbonyl group" or "carbonyl linked" refer to a functional group of a compound, such as a starting compound of the present invention, consisting of a carbon doubly bonded to an oxygen and singly bonded to two carbons of the compound (i.e., R—[C=O]—R', with the R, R' each bonded to the C). For example, a "carbonyl linkage" may join a halogenated phenol ring (R) to a core structure (R') of a compound.

For purposes of the present invention, the terms "sulfoxide linkage," "sulfinyl linkage," "sulfinyl group" or "sulfinyl linked" refer to a functional group of a compound, such as a starting compound of the present invention, consisting of a sulfur atom doubly bonded to an oxygen and singly bonded to two carbons of the compound (i.e., R—[S=O]—R', with the R, R' each bonded to the S). For example, a "sulfoxide linkage" may join a halogenated phenol ring (R) to a core structure (R') of a compound.

For purposes of the present invention, the terms "nitrogen linkage" and "nitrogen linked" refer to a functional group of a secondary amine compound, such as a starting compound of the present invention, consisting of a nitrogen atom singly bonded to a hydrogen and two R-groups of the compound (i.e., R—NH—R', with the R, R' each bonded to the N). For example, a "nitrogen linkage" may join a halogenated phenol ring (R) to a core structure (R') of a compound. In some instances, a "nitrogen linkage" may further include an alternate nitrogen linkage consisting of a nitrogen atom singly bonded to two hydrogens and two R-groups of a compound, such as a starting compound of the present invention, (i.e., R—NH$_2$—R', with the R, R' each bonded to the N) due to the particular chemical features of the compound that permits four bonds with the nitrogen. The nitrogen of this alternate nitrogen linkage may be positively charged.

For purposes of the present invention, the terms "internal nitrogen linkage" or "internal nitrogen linked" refer to a nitrogen of a tertiary amine compound, such as a starting compound of the present invention, consisting of a nitrogen atom singly bonded to three R-groups of the compound (i.e., R, R', R" each bonded to the N). For example, an "internal nitrogen linkage" may join a halogenated phenol ring (R) to a core structure (R'—N—R") of a compound with the nitrogen (N) of the "internal nitrogen linkage" forming part of the core structure of the compound.

For purposes of the present invention, the terms "metal linkage" refers to a bond directly between a first R-group and a metal or metalloid atom or element (as identified in the periodic table). The metal or metalloid element may be part of a second R-group (R'). For example, the metal atom or element may include boron (B) or mercury (Hg). In the case of boron, for example, the boron atom may be able to directly bond to three R-groups (i.e., R, R', R" each bonded to the B), one or more of which may include a halogenated phenol ring. In other cases, such as with mercury, the metal atom (i.e., Hg) directly bonded to the first R-group may be ionized, which may also pair with an anion to form a salt. A metal linkage between a halogenated phenol ring and the metal or metalloid atom or element (which may be part of an R'-group) may become cleaved in a dehalogenation to release the metal or metalloid atom or element that may be part of the R'-group.

For purposes of the present invention, the terms "oxidizing agent" or "oxidative agent" or "oxidizing species" or "oxidative species" refer interchangeably to a substance or compound that accepts an electron(s) from another substance or compound in an oxidation-reduction (redox) reaction. During the redox reaction, the oxidizing agent is reduced while the other substance or compound is oxidized.

For purposes of the present invention, the terms "oxidizing stress" or "oxidative stress" refer interchangeably to a state or condition in a tissue or cellular environment having an elevated level of oxidizing agents relative to a normal or controlled state or condition for such tissue or cellular environment. For example, such oxidative stress may be associated with inflamed and/or diseased cells or tissues.

For purposes of the present invention, the terms "free radical" or "free radicals" refer to reactive substances or molecules having one or more unpaired electron(s).

For purposes of the present invention, the term "free radical stress" refers to a state or condition in a tissue or cellular environment having an elevated level of free radicals relative to a normal or controlled state or condition for such tissue or cellular environment. For example, such free radical stress may be associated with inflamed and/or diseased cells or tissues.

For purposes of the present invention, the terms "chemical group," "functional group," or "group" with regard to chemical compounds and compositions refer interchangeably to an atom or a group of atoms bonded together that form part of the chemical structure of a compound.

For purposes of the present invention, the terms "substituent" or "substituents" with regard to chemical compounds and compositions refer to an atom, radical, or group of bonded atoms of a chemical compound that may be substituted for another atom, radical, or group of bonded atoms. For example, a substituent may refer to an individual chemical group bonded to a carbon, nitrogen or other atom of a chemical compound. Such a substituent may be a functional group providing physical or chemical properties to the compound.

For purposes of the present invention, the term "adjacent" with regard to the chemical structure of a compound in reference to two atoms of that compound refers to a first atom of a ring, such as a benzene ring, of the compound that is next to (i.e., bonded directly to) another atom of the ring. For example, the term may refer to two adjacent carbons of a benzene ring that are bonded to one another. However, the term "adjacent" may also refer to a carbon and a nitrogen of a ring structure that are bonded directly to each other.

For purposes of the present invention, the term "individual," "subject," or "patient" refer interchangeably to a mammal, such as a rat or a human, that may take or be administered, given or provided a compound or composition of the present invention but may most commonly refer to a human. In the case of drug delivery, such an individual may be any mammal, typically a human, having or suffering from inflammation or a condition or disease caused or mediated by, or associated with, higher levels of free radicals and/or oxidative species (FROS), or suspected of having or suffering from the same. Such an individual may also include a mammal, typically a human, that is considered normal (i.e., not necessarily suspected of having or suffering from any of the above conditions) when, for example, a test, screen or preventive treatment is conducted on the individual.

For purposes of the present invention, the term "starting compound" or "original compound" refer interchangeably to a compound of the present invention prior to becoming modified in a dehalogenation (or a dehalogenation and cleavage) reaction.

For purposes of the present invention, the terms "electron donating," "electron releasing," "electron donor," or "electron donating group" in reference to a substituent bonded to a carbon of the benzene ring of a halogenated phenol ring-containing compound of the present invention refer to a substituent that donates electrons to or increases the electron density of the benzene ring of the halogenated phenol ring-containing compound.

For purposes of the present invention, the terms "electron withdrawing," "electron withdrawer," or "electron withdrawing group" in reference to a substituent bonded to a carbon of a halogenated phenol ring-containing compound of the present invention refer to a substituent that withdraws electrons from or reduces the electron density of the halogenated phenol ring-containing compound.

For purposes of the present invention, the terms "benzenetriol" or "benzenetriol-based" refer to compounds containing a benzene ring having three hydroxyl substituents bonded to the benzene ring. A "benzenetriol-based" compound may have hydrogen or substituent(s) other than hydrogen at the other positions of the benzene ring.

For purposes of the present invention, the terms "benzenetetrol" or "benzenetetrol-based" refer to compounds containing a benzene ring having four hydroxyl substituents bonded to the benzene ring. A "benzenetetrol-based" compound may have hydrogen or substituent(s) other than hydrogen at the other positions of the benzene ring.

For purposes of the present invention, the term "hydroquinone" refers to a compound containing a benzene ring having two para-hydroxyl groups.

For purposes of the present invention, the terms "hydroxyhydroquinone" or "hydroxyhydroquinone-based" refer to a compound containing a benzene ring having three hydroxyl groups, such as 1,2,4-benzenetriol.

For purposes of the present invention, the term "indigo" refers to a chemical compound having the chemical formula, $C_{16}H_{10}N_2O_2$ and composed to two indole heterocylic rings joined by a double bond as commonly understood.

For purposes of the present invention, the term "indigo-like compound" refers to a compound having the chemical structure of indigo, but which may also have one or more substituents other than hydrogen on the benzene ring(s) of one or both of the two heterocyclic indole rings. For example, an indigo like compound may include an indigo compound having a halogen and/or a radioactive isotope as a substituent on the benzene ring(s) of one or both of the two heterocyclic indole rings.

For purposes of the present invention, the terms "indole" or "indole containing compound" refer to a molecule or compound containing one or more heterocyclic indole rings. For purposes of the present invention, the terms "indole rings" or "heterocyclic indole rings" refer to a bicyclic chemical structure having a six-membered benzene ring fused to a five-membered nitrogen-containing pyrrole ring.

For purposes of the present invention, the term "residence time" refers to a property of a compound having a tendency to linger or remain in a tissue or cellular environment due to its chemical properties. A compound having a high residence time may include a hydrophobic or lipophilic compound. For example, a compound having a high residence time may include an indigo-like compound.

For purposes of the present invention, the term "sensitivity of cleavage" refers to a property of how easily a linkage (e.g., ether linkage, etc.) between a compound, such as a drug compound, and a halogenated phenol ring of a starting compound becomes cleaved or broken in the presence of free radicals and/or oxidative agents. A starting compound having a high sensitivity of cleavage has a low threshold of cleavage (i.e., the linkage between the compound and the halogenated phenol ring is easily cleaved in the presence of free radicals and/or oxidative agents). In contrast, a starting compound having a low sensitivity of cleavage has a high threshold of cleavage (i.e., the linkage between the compound and the halogenated phenol ring is not easily cleaved in the presence of free radicals and/or oxidative agents). In general, it is believed that halogenated phenol compounds having more destabilization of the phenol ring will have a higher sensitivity of cleavage.

For purposes of the present invention, the term "infectious agent" refers to an infectious particle or organism which can infect a cell or tissue, such as a virus, bacterium, protozoan, fungus, etc.

For purposes of the present invention, a "drug compound" refers to any compound having a known chemical structure that is currently used or administered as an existing form of therapy for the treatment, alleviation, prevention, etc., of a disease or a physiological, veterinary or medical condition. In the case of drugs for medical use, a "drug compound" includes any such compound that is available either over-the-counter (OTC) or by prescription, which may be administered by any suitable route of administration. A "drug compound" for purposes of the present invention may include not only drug compounds that are taken or administered into the body, but also any known and anticipated metabolites of these drugs having a known chemical structure. For example, a metabolite of a taken or administered drug compound may include a known "active form" of the administered drug compound having a known chemical structure produced by chemical modification of the drug from its taken or administered "pro-drug" foam (due to bodily mechanisms in the liver and other tissues of the individual receiving the "pro-drug" form of the drug).

For purposes of the present invention, the term "core structure" refers to the majority portion of a compound or drug compound minus (i.e., without) the substituent that participates in forming the linkage with a halogenated phenol ring (HPR). For example, if a drug compound ($R_1$—YH) is linked to a halogenated phenol ring (i.e., $R_1$—Y—HPR) by an ether or thioether linkage (with Y being oxygen or sulfur), then the "core structure" of the drug compound would be $R_1$. Likewise, if a drug compound ($R_1$—$NH_2$) is linked to a halogenated phenol ring (i.e., $R_1$—NH—HPR) by a nitrogen linkage, or if a drug compound ($R_1$—COOH) is linked to a halogenated phenol ring (i.e., $R_1$—[C=O]-HPR) by a carbonyl linkage, or if a drug compound ($R_1$—$CH_2OH$) is linked to a halogenated phenol ring (i.e., $CH_2$—HPR) by a C—C bond, or if a drug compound ($R_1$—$SO_3H$) is linked to a halogenated phenol ring (i.e., $R_1$—[S=O]—HPR) by a sulfinyl linkage, then (in each case) the "core structure" of the drug compound would be $R_1$. Similarly, if a drug compound ($R_1$—H consisting of R'—NH—R" with $R_1$ the same as R'—N—R") is linked to a halogenated phenol ring (i.e., R'/R"—N—HPR or, in other words, the N singly bonded to R', R" and HPR) by an internal nitrogen linkage, then the "core structure" of the drug compound would be $R_1$ (i.e., R'—N—R"). With regard to the core structure of a compound or drug compound, the "substituent" refers only to the limited set of substituents on the compound or drug compound that are identified herein as being capable of being converted or reacted to form a linkage with a halogenated phenol ring: a hydroxyl (—OH), keto (C=O), carboxyl (—COOH), amino (—$NH_2$), alcohol (—$CH_2OH$), sulfonic acid ($SO_3H$) or sulfhydryl (—SH) group(s) or a hydrogen (—H) bonded to a nitrogen of a core structure (in the case of an internal nitrogen linkage).

For purposes of the present invention, the terms "empty unit" or "empty units" refer to a monomer or unit of a polymer of the present invention that is not directly bonded to a drug compound via a linkage (i.e., an ether linkage, etc.).

For purposes of the present invention, the term "purify" in reference to a substance or compound in a sample means to selectively remove other components from the sample relative to the amount of the substance or compound to produce a purified sample of the substance or compound. The term "concentrate" in reference to a substance or compound in a sample means increasing the concentration of the substance or compound relative to other components to produce a concentrated sample of the substance or compound. In either case, the "purified sample" or "concentrated sample" may be referred to simply as a "sample" with the substance or compound purified or concentrated therein, respectively, from an initial or original sample taken from an individual.

For purposes of the present invention, the terms "administer," "administering," and "administration" in reference to a composition, compound or drug mean taking, placing, putting, etc., the composition, compound or drug into the body of an individual by any method and by any route of administration. Such "administering" or "administration" may be performed by the individual, a health care provider or any other person.

Description

Site specific drug delivery systems generally attempt to exploit unique characteristics of target tissues or cells. In addition to targeting specific cell surface markers or achieving targeted delivery through local administration, drug delivery systems have been proposed to release drugs or therapeutics under specific chemical conditions (e.g., altered pH, temperature, etc.) that may exist in a target tissue. Other specialized approaches for targeted delivery of drugs (e.g., use of external magnets with magnetic carriers) have also been proposed. See, e.g., Torchlin, V. P., "Drug Targeting." *Eur. J. Pharm. Sci.*, 11 (Suppl 2): S81-91 (2000). The present invention provides for the targeted delivery and release of a drug or therapeutic compound to sites of inflamed, diseased, neoplastic, metastatic, infected, etc., cells or tissue, which are generally characterized by high levels of oxidizing agents and/or free radicals resulting from the inflammation or pathology of the targeted cells or tissue.

Various diseases and conditions are associated with affected cells and tissues (including diseased cells and tissues, such as tumors, etc.) becoming hypermetabolic. This hypermetabolism may lead to elevated levels of free radicals and/or oxidative species (FROS) in those cells and tissues, which may be due in part to the release of these FROS from "leaky" mitochondria. Such hypermetabolism may be evidenced by weight loss, cachexia, etc., and referred to as "free radical catastrophe" in extreme cases. Many conditions or disease states may also lead to hyperthyroidism, which may also increase the rate of metabolism in affected tissues or cells. In addition, sites of immunity and inflammation, which may be associated with tissue injury, transplantation rejection or other diseases, may also lead to conditions of increased FROS within those tissues and be amenable to treatment by present embodiments. These diseases and conditions may thus be amenable to treatment, prevention, etc., according to embodiments of the present invention, which as described below, may be used to provide targeted delivery of drug compound(s) and/or other activities at sites of high FROS.

Hypometabolic events associated with ischemic may also result in FROS generation. For example, myocardial infarct and stroke may result in at least temporary, localized ischemic deprivation of oxygen and nutrients, resulting in metabolic failure and depletion of natural FROS quenching mechanisms. Failure of mitochondrial integrity can also result in FROS generation through membrane leakage and hyper-compensatory metabolic responses. Reperfusion of such ischemic tissues, as a standard course of therapy, can also result in further FROS damage to the tissues affected. The combination of depleted FROS defenses and/or increased FROS can lead to cellular or tissue damage or death. Thus, embodiments of the present invention may also be beneficially applied in these contexts to help protect or rescue these tissues during or following these events. For example, compound embodiments may be administered in conjunction with reperfusion therapy.

According to embodiments of the present invention, these properties of diseased and/or inflamed cells or tissues are exploited by designing compounds that will provide targeted release and unmasking of drug compounds at these high FROS sites within the body of an individual. As described further below, such compounds may generally comprise a drug compound conjugated to a halogenated phenol ring via a chemical linkage, which may include an ether, thioether, carbonyl, sulfinyl, nitrogen, internal nitrogen or possibly a C—C bond or linkage. When such a compound of the present invention comes in contact with, or is present within, an oxidizing and/or free radical containing environment, such as in a diseased and/or inflamed tissue, a spontaneous reaction may occur resulting in cleavage of the chemical linkage and release of the liberated drug compound from the halogenated phenol ring. Because this cleavage reaction involves the consumption of free radicals or oxidative species (FROS), it is further proposed that compounds of the present invention may also be used as FROS scavengers. In addition, this cleavage reaction may also be used for diagnostic purposes as a basis for releasing or forming detectable compounds as an indicator of high FROS systemically in the body or in specific tissues.

Enzymatic reductive deiodination of thyroid hormones, replacing the covalently bound iodine of the thyronine nucleus with a hydrogen, has been observed. See, e.g., Leonard, J. et al., *The Thyroid*, Lippincott-Raven (Braverman, L. E. and Utiger, R. D., Eds.), pp. 125-161 (1996), the contents and disclosure of which is incorporated herein by reference. For example, thyroxine may be converted to 3,5, 3'-triiodo-L-thyronine (T3) by this process. However, reductive deiodination is contrary to the present invention which describes an oxidative process in which the halogen (i.e., iodine) is removed and replaced with a hydroxyl group along with cleavage of the relevant linkage or bond, such as an ether linkage, etc. It is proposed that this chemical mechanism may be utilized in the design of new targeted drugs and the development of new therapeutic and diagnostic approaches. The general use of this oxidative and/or free radical process according to the present invention may define a new platform or paradigm, which may be referred to as Oxidative or Free Radical Medicine to distinguish it from other therapeutic approaches.

In contrast to reductive deiodination, spontaneous dehalogenation (e.g., deiodination) of a halogentated phenol ring in the presence of an oxidizing agent(s) and/or free radical(s) with cleavage of a chemical linkage, such as an ether linkage, etc., between the phenol ring and a conjugated compound has not been described. According to the present invention, cleavage of the ether linkage between the aromatic rings of thyroid hormone may form visibly colored quinone and iodine-containing products in buffered aqueous solutions in vitro, and this ether cleavage reaction may be accelerated under basic pH conditions and with exposure to ionizing radiation or light. These conditions favor the increased formation of oxidizing agents and/or free radicals, which are believed to promote the reaction. For example, it has been discovered that if about 1 mM of thyroxine is dissolved in carbonate buffer (pH 8.0) and exposed to sunlight for about one hour, the ether linkage is broken spontaneously, and a clear yellow/orange solution is formed as iodide is released from the phenolic 3-ring. A quinone and an iodotyrosine product are also formed by cleavage of the ether linkage during the reaction. According to embodiments of the present invention, a spontaneous reaction of dehalogenation and cleavage of a chemical bond is proposed for the targeted delivery and release of a drug compound at or to sites of inflammation or disease. This spontaneous reaction is further proposed as a basis for scavenging free radicals and/or oxidative agents (FROS) as well as for the creation of a detectable compound(s) that may be used for diagnostic purposes.

The discovery that an ether linkage between a halogentated phenol ring and a conjugated compound becomes cleaved upon dehalogenation of the halogenated phenol ring in the presence of oxidizing agents and/or free radicals is unexpected since ether linkages are considered to be especially stable (i.e., a bond energy of greater than about 200 kcal/mol), compared to C—C bonds (i.e., about 102 kcal/mol) and C—H bonds (i.e., about 80 kcal/mol), which are also regarded as stable bonds. However, it has been found that following supposed free radical attack of the phenol ring, the ether linkage becomes surprisingly labile and is subsequently cleaved to reach a lower energy state.

It has also been discovered that other types of bonds or linkages may also be cleaved by oxidative or free radical-mediated dehalogenation of the phenol ring. For example, as described herein, it has now been observed that a carbonyl linkage, a nitrogen linkage, a sulfinyl linkage and possibly a C—C bond on the phenol ring may also be cleaved by the oxidative dehalogenation reaction. These bonds are also considered stable, and their cleavage in connection with the dehalogenation reaction is surprising as well. One caveat with the C—C bond or linkage is that depending on the particular starting compound structure and the substituents or groups attached to the halogenated phenol ring via the C—C bond, the C—C bond or linkage may or may not be generally cleaved during or following the dehalogenation reaction (see below). For example, mono-iodotyrosine (MIT) discussed below is found generally not to be cleaved with the reaction. However, other compounds do become cleaved. It is important to note that whether a C—C bond of a particular starting compound is "cleavable," or becomes cleaved, may not be all-or-nothing (i.e., the C—C bond may be considered non-cleavable even though a small or minute amount of cleavage may occur, and vice versa). Thus, the amount or percentage of cleavage may be partial with the alternatively cleaved or non-cleaved product being possibly undetected or minute.

Without being bound by any theory, it is believed that upon free radical attack or oxidation of the halogen bond of a halogenated phenol ring, the halogen becomes removed and replaced with a hydroxyl and changes occur to the cloud of electrons within the phenol ring. These changes to the electron cloud are believed to result in the bond or linkage (e.g., ether linkage, carbonyl linkage, etc.) connecting the conjugated compound to the ring to become labile, which may ultimately become cleaved (and replaced with another hydroxyl group). For this chemistry to work, water molecules (or their ions) from a surrounding aqueous environment are needed to supply the hydroxyl groups added to the ring during the reaction, as well as hydrogen(s), oxygen(s) and/or hydroxyl(s) that may be added to the (drug) compound cleaved from the ring. This requirement for an aqueous environment is met under physiological conditions, making this technology suitable for pharmaceutical applications. It is further observed that linkages at positions further away from the hydroxyl group on the halogenated phenol ring may generally tend to be more sensitive to cleavage, which may reflect the spatial reorganization of the electron cloud that takes place during or following the dehalogenation reaction. Thus, the para position relative to the hydroxyl may be the most sensitive to cleavage, as compared to the meta and ortho positions. However, the exact changes to the electron cloud during or following the dehalogenation reaction (and the sensitivity at any one position) may depend on other substituents present on the phenol ring.

According to a first broad aspect of the present invention, it is proposed that the oxidation and/or free radical mediated cleavage reaction may be generally applied to a wide variety of drug compound(s) linked, bonded, conjugated, etc., to a halogenated phenol ring by an ether, thioether, carbonyl, sulfinyl, nitrogen, internal nitrogen or C—C bond or linkage to form (starting) compounds of the present invention. These starting compounds comprising a halogenated phenol ring conjugated or linked to the drug compound may be used to achieve site-specific delivery and targeted release of the drug compound(s) to locations within the body of an individual experiencing or having elevated levels of oxidative and/or free radical stress, which are often associated with diseased and/or inflamed cells or tissues. For the reaction to work effectively, the halogen substituent bonded to the phenol ring of the starting compound of the present invention needs to be adjacent to (i.e., in the ortho position relative to) the hydroxyl group or substituent of the phenol ring. However, the linkage(s) between the phenol ring and the drug compound(s) of the starting compound of the present invention, may potentially be positioned anywhere on the phenol ring not occupied by the halogen and hydroxyl group (i.e., bonded to any one of the four remaining carbons on the phenol ring), and a variety of different chemical groups or substituents may be bonded to the remaining carbons of the phenol ring.

According to embodiments of the present invention, the linkage between the halogenated phenol ring and a linked compound, such as a drug compound, may comprise: an ether linkage or group (—O—), a thioether linkage or group (—S—), a carbonyl linkage or group (—[C=O]—), a sulfinyl linkage or group (—[S=O]—), a nitrogen linkage or group (—NH—), or possibly a C—C bond. The linkage may also include an internal nitrogen linkage if a nitrogen of a secondary amine (drug) compound is linked to the halogenated phenol ring (to form a starting compound having a tertiary amine structure). However, for a linked compound, such as a drug compound, to become covalently bonded to the halogenated phenol ring, such compound must contain at least one suitable substituent capable of forming one of these types of bonds or linkages. Thus, the linked (drug) compound may include any such compound having one or more of: a hydroxyl (—OH), a keto (C=O), a carboxyl (—COOH), an amino (—NH$_2$), an alcohol (—CH$_2$OH), a sulfonic acid (—SO$_3$H) or a sulfhydryl (—SH) group, or a hydrogen (—H) bonded to an "internal" nitrogen of a secondary amine (drug) compound, which is capable of being converted or used to form one of the respective cleavable linkages listed above with the halogenated phenol ring.

Compounds or drug compounds having a keto group in their most stable form may be ether linked to the halogenated phenol ring in some circumstances. A compound having (i) a keto group and (ii) an adjacent single bond that may be engineered into a double bond, may be ether linked to a halogenated phenol ring via the carbon having the keto group. This approach relies on the carbon of the keto group (of the (drug) compound) to have the engineered double bond with an adjacent carbon. Although a hydroxyl group may be initially formed by the cleavage reaction on the carbon at the ether linkage position, this hydroxyl group may then spontaneously resonate or tautomerize with the adjacent double bond to form the keto group on the liberated (drug) compound, which will eliminate the adjacent double bond. Therefore, drug compounds having a keto group that may be ether linked to a halogenated phenol ring of a starting compound of the present invention must have a single bond adjacent to the keto carbon that is capable of forming a double bond (usually by elimination of a bond to a hydrogen). Accordingly, an adjacent carbon of a drug compound may not be bonded to more than three non-hydrogen atoms, and an adjacent nitrogen may not be bonded to more than two non-hydrogen atoms, so that they are able to accept the double bond. According to some embodiments, for a drug compound having a keto group to be ether linked to a halogenated phenol ring such that the starting compound will reform the drug compound upon cleavage, the carbon of the keto group and the adjacent double bond may preferentially be part of a six-membered ring structure having partial aromaticity (i.e., with one or two double bonds including the adjacent double bond). Without being bound by any theory, it is believed that in some cases, the electrons of the partially aromatic ring may assist in forming the intermediate, which then resonates to form the lower energy keto-tautomer, although this may not always be necessary.

Due to the wide range of chemical groups that may be covalently linked to a halogenated phenol ring, the general applicability of the present invention is potentially very broad. The range of drugs or compounds containing one or more of: a hydroxyl, keto, carboxyl, amino, alcohol, sulfonic acid or sulfhydryl group, or a hydrogen (—H) bonded to an "internal" nitrogen of a secondary amine compound, that may be linked to a halogenated phenol compound is very large. Indeed, these chemical groups or substituents are ubiquitously present in natural and synthetic compounds. Thus, according to embodiments of the present invention, the compound or drug linked or bonded to the halogenated phenol ring (and released during the cleavage reaction) may theoretically include a large variety of drugs or compounds containing one or more of: a hydroxyl (—OH), keto (C═O), carboxyl (—COOH), amino (—NH$_2$), alcohol (—CH$_2$OH), sulfonic acid (SO$_3$H) or sulfhydryl (—SH) group(s), or a hydrogen (—H) bonded to an "internal" nitrogen in the case of a secondary amine compound, that may be linked as described herein. To name a few, examples of drug compounds that may be linked to a halogenated phenol ring as a part of a starting compound of the present invention may include steroids, some of which may be anti-inflammatory steroid including corticosteroids, such as cortisol, cortisone, corticosterone, hydrocortisone, prednisone, prednisolone, methylprednisolone, betamethasone, etc., or other steroids, such as estrogen, etc., peptide and non-steroidal hormones, such as insulin, etc., thyroid hormones, such as thyroxine, triiodothyronine, etc., catecholamines, such as dopamine, L-DOPA, etc., adrenergics, such as epinephrine, norepinephrine, etc., amino acids, such as tyrosine, cysteine, serine, etc., antibiotics, such as β-lactam antibiotics including penicillins, cephalosporins, etc., anti-inflammatories, antipyretics, analgesics and NSAIDs, such as aspirin, acetaminophen, ibuprofen, naproxen, etc., vitamins, such as vitamin A, vitamin E, etc., narcotics and opioids, such as methadone, morphine, amphetamine, etc., serotonergics, such as serotonin, etc., chemotherapies or cytotoxic drugs, such as methotrexate, etc., and many others.

A person skilled in the art would be able to select compounds, as well as drug compounds or their metabolites in the body, that contain at least one of the suitable substituents: a hydroxyl (—OH), a keto (C═O), a sulfonic acid (—SO$_3$H), a carboxyl (—COOH), an amino (—NH$_2$), an alcohol (—CH$_2$OH) or a sulfhydryl (—SH) group(s), or a hydrogen (—H) bonded to an "internal" nitrogen of a secondary amine compound, based on their known chemical structure. See, e.g., *The Merck Index: an encyclopedia of chemicals, drugs and biological*, 14th Edition, Merck, Whitehouse Station, N.J. (2006); and *Aldrich Structure Index*, Aldrich Chemical Company (1996), the contents and disclosure of which are incorporated by reference, providing a long list of known chemical compounds from which candidate compounds having one or more of these substituent(s) may be identified and selected for purposes of the present invention. According to the principles described herein, the appropriate linkage between the selected (candidate) compound and a halogenated phenol ring may be determined based on the respective substituent, and the chemical structure or formula of the starting compound formed by such linkage may then be further determined according to the principles of the present invention as provided herein. Although it would not be feasible to draw every chemical structure covered by the present invention, enough enabling description and examples are provided herein to determine the chemical structure of any starting compound of the present invention.

According to some embodiments, a compound that may be linked to a halogenated phenol ring to form a starting compound of the present invention may include not only known or existing drug compounds, but also their known and anticipated metabolites. Many drugs are chemically or enzymatically modified in hepatic and other tissues of the body. Indeed, many drugs have structures that anticipate these mechanisms to form the active compound after being taken or administered. Since a key advantage of the present invention is the formation or release of a drug compound at a site of need, such as a site of inflammation or disease having high FROS), the drug compound may not undergo such modification at the site or release and formation and thus may be attached in its active form. However, a drug compound may alternatively be attached in its "pro-drug" form in some circumstances, especially if it can be readily converted into its active form at the site where it is formed.

According to the principles of the present invention as described herein, any such compound or drug compound known in the art and identified as having: a hydroxyl (—OH), keto (C═O), carboxyl (—COOH), amino (—NH$_2$), alcohol (—CH$_2$OH) sulfonic acid (—SO$_3$H), or sulfhydryl (—SH) group(s) or substituent(s), or a hydrogen (—H) bonded to an "internal" nitrogen of a secondary amine compound, may potentially be linked to a halogenated phenol ring by modification of the respective substituent. As described further herein, a hydroxyl group (or possibly a keto group) of a (drug) compound may be ether linked (—O—) to a halogenated phenol ring, a sulfhydryl group of a (drug) compound may be thioether linked (—S—) to a halogenated phenol ring, a carboxyl group may be carbonyl linked (—[C═O]) to a halogenated phenol ring, a sulfonic acid group may be sulfinyl linked (—[S═O]—) to a halogenated phenol ring, and an amino group may be nitrogen linked (—NH—) to a halogenated phenol ring. Likewise, a hydrogen bonded to an "internal" nitrogen of a secondary amine (drug) compound may be internal nitrogen linked to a halogenated phenol ring. In some circumstances, an alcohol substituent (—CH$_2$OH) of a (drug) compound may be linked to a halogenated phenol ring by a cleavable C—C bond.

As discussed further below, (i) cleavage of an ether linkage will produce a hydroxyl on the liberated (drug) compound (which may resonate into a keto group depending on the identity of the compound), (ii) cleavage of a thioether bond will produce a sulfhydryl group on the liberated compound, (iii) cleavage of a nitrogen linkage will produce an amino group on the liberated compound, (iv) cleavage of a carbonyl linkage may generally produce a carboxyl group on the liberated compound, (v) cleavage of a sulfinyl linkage will generally produce a sulfinic acid group, (vi) cleavage of an internal nitrogen linkage will generally produce a secondary amine group on the liberated compound, and (vii) cleavage of a C—C bond may generally produce an alcohol group on the liberated compound if cleavage occurs. In these cases, the cleavage reaction will liberate the (drug) compound as a result of the dehalogenation reaction. Thus, starting compounds of the present invention may potentially include any suitable compound (or drug compound) linked to a halogenated phenol ring by any of these cleavable linkages via a suitable substituent on the linked compound.

Cleavage of an ether, thioether or nitrogen linkage will produce a hydroxyl (or keto), sulfhydryl, or amino group, respectively, on the liberated compound by the addition of a hydrogen (the keto group presumably forms by tautomerization of the initially formed hydroxyl). However, in the case of a carbonyl linkage or C—C bond, cleavage will produce a carboxyl or alcohol group by addition of a hydroxyl group. It is not clear why some cleavage reactions add only a hydrogen to the liberated compound, while other reactions result ultimately in the addition of a hydroxyl, but the difference may derive from the presence of a carbon in both cases involving a carbonyl linkage or C—C bond. One theory could be that, in the case of a cleaved carbonyl linkage, an aldehyde (by addition of only a hydrogen) is first formed as an intermediate, which is then subsequently converted into the carboxylic acid by oxidation. However, examples showing the formation of an alcohol (—CH$_2$OH) upon cleavage of a C—C bond would seem to counter this theory and suggest direct addition of the hydroxyl group in these cases. Moreover, cleavage of a sulfinyl linkage will produce a sulfonic acid group on the liberated compound by the addition of an oxygen atom and a hydroxyl, which presents another curious distinction for this linkage and substituent.

As mentioned above, a variety of drug compounds may be linked to a halogenated phenol ring for targeted release and delivery at high FROS sites in body. The following list of examples of drug compounds are provided with the possible types of linkages to a halogenated phenol ring listed in parenthesis (not necessarily exhaustive): E=ether linkage at a hydroxyl group; T=thioether linkage; N=nitrogen linkage; C=carbonyl linkage; IN=internal nitrogen linkage; Ek=ether linkage at a keto group.

Examples of chemotherapeutic agents that may be linked to a halogenated phenol ring may include alkylating agents, such as nitrogen mustards including chlorambucil (C), cyclophosphamide (IN), ifosfamide (IN), and melphalan (C, N), nitrosureas including carmustine (IN), streptozocin (E, IN) and lomustine (IN), and triazines including dacarbazine (N) and temozolomide (N); antimetabolites, such as 5-fluorouridine or 5-FU (Ek, IN), 6-mercaptopurine (IN, T), capecitabine (E, IN), cladribine (E, N), clofarabine (E, N), floxuridine (E, IN), fludarabine (N, E), gemcitabine (E, N), cytarabine (E, N), azacitadine (E, N), azathioprine (IN), doxifluridine (E, IN), hydroxyurea (N, E), methotrexate (N, C, IN, Ek), pemetrexed (N, C, IN, Ek), pentostatin (E, IN), thioguanine (N, IN, T); antitumor antibiotics, such as actinomycin (IN, N, Ek), bleomycin (E, N, IN), mitomycin (N, Ek), and anthracyclines including daunorubicin (E, N), doxorubicin (E, N), epirubicin (E, N), idarubicin (E, N), mitoxantrone (E, IN) and valrubicin (E, IN); topoisomerase inhibitors, such as etoposide (E), teniposide (E), tafluposide (Ek), topotecan (E), irinotecan (E); mitotic inhibitors, such as taxanes including paclitaxel (E, IN), docetaxel (E, IN), epothilones including ixabepilone (E, IN), vinka alkaloids including vinblastine (E, IN), vincristine (E, IN), vindesine (E, IN) and vinorelbine (E, IN), and estramustine (E); corticosteroids, such as dexamethasone (E, Ek); kinase inhibitors, such as bortezomib (IN, Ek), erlotinib (IN), sunitinib (IN, Ek), gefitinib (IN), imatinib (IN, Ek) and vismodegib (IN, Ek); histone deacetylase inhibitors, such as vorinostat (IN, Ek) and romidepsin (IN, Ek); retinoids, such as tretinoin (C), alitretmoin (C) and bexarotene (C); Pt-based agents, such as carboplatin (N), cisplatin (N) and oxaliplatin (N); and others, such as fulvestrant (E), exemestane (Ek), megestrol acetate (E), bicalutamide (E, IN), flutamide (Ek, IN), nilutamide (Ek, IN), leuprolide (E, IN) and goserelin (E, IN), Examples of analgesics, NSAIDs and anesthetics that may be linked to a halogenated phenol ring may include acetaminophen (E, IN); NSAIDs, such as diclofenac (C, IN), diflunisal (C, E), etodolac (C), fenoprofen (C), flurbiprofen (C), ibuprofen (C), indomethacin (C), ketoprofen (C), ketorolac (C), meclofenamate (C, IN), mefenamic acid (C, IN), meloxicam (E, IN), nabumetone (Ek), naproxen (C), oxaprozin (C), phenylbutazone (Ek), piroxicam (E, IN), sulindac (C), tolmetin (C); Cox-2 inhibitors, such as celecoxib (N); narcotics, such as buprenorphine (E), butorphanol (E), codeine (E), dihydrocodeine (E), hydrocodone (Ek), hydromorphone (E), levorphanol (E), methadone (Ek), morphine (E), nalbuphine (E), oxycodone (E), oxymorphone (E), pentazocine (E), propoxyphene (Ek) and tapentadol (E); central analgesics, such as tramadol (E); and anesthetics, such as benzocaine (N), dibucaine (IN, Ek), and lidocaine (IN, Ek).

Examples of antibiotics that may be linked to a halogenated phenol ring may include aminoglycosides, such as amikacin (E, N), gentamicin (E, N), kanamycin (E, N), neomycin (E, N), netilmicin (E, N), tobramycin (E, N) and paromomycin (E, N); ansamycins, such as geldanamycin (E, N) and herbimycin (N, Ek); carbacephems, such as loracarbef (C, N); carbapenems, such as ertapenem (C, E, IN), doripenem (C, E, N), imipenem (E, C, IN), cilastatin (C, N, IN) and meropenem (C, E, IN); cephalosporins, such as cefadroxil (E, N, C), cefazolin (C, IN), cefalotin (C, IN), cefalexin (C, N), cefaclor (C, N), cefamandole (C, E, IN), cefoxitin (C, N), cefprozil (C, N, E), cefuroxime (C, N), cefixime (C, N), cefdinir (C, N), cefditoren (C, N), cefoperazone (C, E), cefotaxime (C, N), cefpodoxime (C, N), ceftazidime (C, N), ceftibuten (C, N), ceftizoxime (C, N), ceftriaxone (C, N), cefepime (N), ceftaroline fosamil (C, IN, Ek) and ceftobiprole (C, N); glycopeptides, such as teicoplanin (E, N), vancomycin (E, N, C) and telavancin (E, N); lincosamides, such as clindamycin (E, IN) and lincomycin (E, IN); lipopeptides, such as daptomycin (C, N, E); macrolides, such as azithromycin (E), clarithromycin (E), dirithromycin (E), erythromycin (E), roxithromycin (E), troleandomycin (Ek), telithromycin (E), spectinomycin (E, IN) and spiramycin (E); monobactams, such as aztreonam (N, C, Ek); and nitrofurans, such as nitrofurantoin (Ek).

Further examples of antibiotics that may be linked to a halogenated phenol ring may include penicillins; such as amoxicillin (E, N, C), ampicillin (C, N, Ek), azlocillin (C, IN, Ek), carbenicillin (C, IN, Ek), cloxacillin (C, IN, Ek), dicloxacillin (C, IN, Ek), flucloxacillin (C, IN, Ek), mezlocillin (C, IN, Ek), methicillin (C, IN, Ek), nafcillin (C, IN, Ek), oxacillin (C, IN, Ek), penicillin G (C, IN, Ek), penicillin V (C, IN, Ek), piperacillin (C, IN, Ek), temocillin (C, IN, Ek) and ticarcillin (C, IN, Ek); polypeptides, such as bacitracin (C, N, Ek), colistin (E, N) and polymyxin b (N, E); quinolones, such as ciprofloxacin (C, IN, Ek), enoxacin (C, IN), gatifloxacin (C, IN), levofloxacin (C), lomefloxacin (C, IN), moxifloxacin (C, IN), nalidixic acid (C), norfloxacin (C, IN), ofloxacin (C), trovafloxacin (C, IN), grepafloxacin (C, IN), sparfloxacin (C, N) and temafloxacin (C, IN); sulfonamides, such as mafenide (N), sulfonamidochrysoidine (N), sulfacetamide (N), sulfadiazine (N), sulfamethizole (N), sulfamethoxazole (N), sulfanilimide (N), sulfasalazine (C, E) and sulfisoxazole (N); tetracyclines, such as demeclocycline (E, N), doxycycline (E, N), minocycline (E, N), oxytetracycline (E, N) and tetracycline (E, N); mycobacterial agents, such as clofazimine (IN), dapsone (N), capreomycin (N, E), cycloserine (N, Ek), ethambutol (E, IN), ethionamide (N), isoniazid (N, Ek), pyrazinamide (N, Ek), rifampicin (E, IN), rifabutin (E, IN), rifapentine (E, IN) and streptomycin (E, N); and others, such as arsphenamine (E, N), chloramphenicol (E, IN), fusidic acid (C, E), linezolid (IN), metronidazole (E), mupirocin (C, E), platensimycin (E, C), rifaximin (E), thiamphenicol (E), tigecycline (N, E) and trimethoprim (N).

As mentioned above, one of the key advantages of present embodiments is the targeted release of therapeutic compounds at sites of free radicals and/or oxidative stress, which may reduce side effects in non-targeted tissues. Sites of infection or autoimmunity will generally be associated with inflammation and higher levels of FROS. For example, the targeted release of cortisone and antioxidants may occur in arthritic joints while minimizing systemic effects of the cortisone due to its masking prior to release. As another example, an antibiotic may have targeted release preferentially at sites of infection, which may reduce unwanted side effects. Likewise, targeted release of neurotransmitters, perhaps in concert with antioxidants, within brain regions affected by damage and/or free radical/oxidative stress resulting from disease processes, such as Parkinson's or Alzheimer's diseases, may alter the course of further neuro-degeneration in these brain regions. As a further example, targeted release of chemotherapeutic agents may be achieved at sites of cancer or tumors, which may reduce side effects on normal or healthy cells or tissues. Indeed, tumors may be hypermetabolic and elicit a local inflammatory response, which may each lead to the release and/or leakage of FROS at these sites.

With regard to the targeted delivery of drugs, FIGS. 1-14 provide general formulas and examples of compounds or drugs that are ether (or thioether) linked to a halogenated phenol ring, which may be released by cleavage of the ether or thioether bond by the dehalogenation reaction. Later discussion in the text and figures will present examples for other types of chemical linkages introduced above (e.g., carbonyl linkage, etc.) that may be used in place of an ether or thioether linkage for these embodiments.

FIG. 1 provides a general class of compounds (Formula 1) according to embodiments of the present invention. According to these embodiments, a compound ($R_1$—YH), such as a drug compound, may be bonded or linked by an ether or thioether linkage to a halogenated phenol ring to form part of a compound of the present invention. The ether or thioether linkage (—Y—) may be an ether linkage or group if Y is an oxygen atom and the —YH group is a hydroxyl group, or a thioether linkage or group if Y is a sulfur atom and the —YH group is a sulfhydryl group. X is a halogen in the ortho position relative to a hydroxyl group (—OH) on the phenol ring (i.e., X is a halogen that is bonded to a carbon that is adjacent to a carbon bonded to a hydroxyl group (—OH) on the phenol ring). The halogen X may be selected from either iodine (I) or bromine (Br), but generally may not include fluorine (F) or chlorine (Cl). According to these embodiments, the ether or thioether linkage (—Y—) is positioned in the meta position relative to the halogen X on the phenol ring and in the para position relative to the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. According to some alternative embodiments, one, two, or three of these variable substituents may be hydrogen. Furthermore, combinations of these other substituents, $R_2$, $R_3$, and $R_4$, present on the phenol ring may themselves form fused rings with the halogenated phenol ring.

The substituents $R_1$—Y and $R_2$, $R_3$, and $R_4$ are each shown in FIG. 1 to bisect the bonds between carbons of the phenol ring as a standard and conventional depiction to represent that the actual positions of those substituents may vary among the carbons of the ring in relation to each other and in relation to the halogen (X) and the hydroxyl (OH) groups. This standard depiction is also used throughout this specification and accompanying figures to represent variable positioning of substituents. By contrast, when a substituent is shown directly bonded to a carbon of a ring structure, then that positioning is fixed. In addition, hydrogens that are part of a chemical structure may or may not be shown. As is customary, when a substituent that must be present according to the chemical laws of valency is not shown, then it is hydrogen. Thus, if a carbon atom of a compound is shown with fewer than four bonds, then the remainder of the substituents on that carbon are hydrogen(s).

According to embodiments of the present invention shown in FIG. 1, when a compound of Formula 1 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the ether or thioether linkage (—Y—) between the drug compound and the phenol ring to release the drug compound ($R_1$—YH), and the ether or thioether linkage is replaced by a hydroxyl group on the phenol ring. The origin of the two hydroxyls replacing the halogen and the former ether (or thioether) linkage on the phenol ring is presumably from the water molecules of the surrounding aqueous environment, and the hydrogen added to the oxygen or sulfur atom (Y) on the liberated drug compound is also presumably from the aqueous environment. In addition to release of a proton ($H^+$; not shown), a halide ($X^-$) and drug compound, a benzenetriol-based or hydroxyhydroquinone-based compound (e.g., 1,2, 4-benzenetriol) may be formed. However, the exact formula name for this product of the reaction will depend on the identity of the additional substituents, $R_2$, $R_3$, and $R_4$. Indeed, one or more of these additional substituents may be hydroxyl groups.

Figure 2:
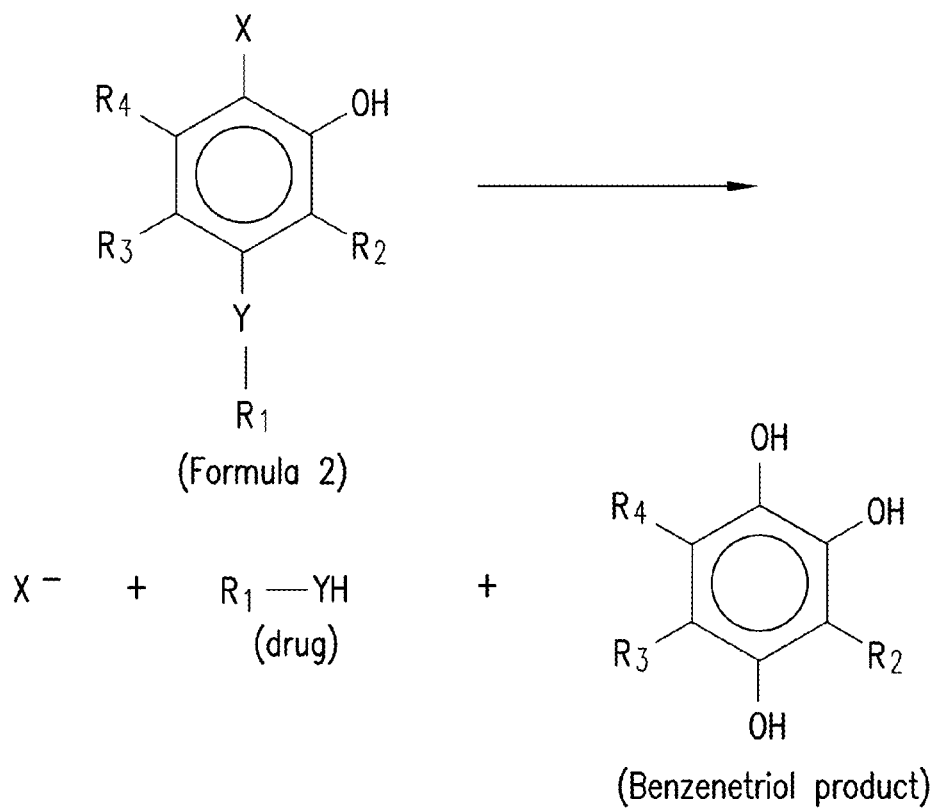
FIG. 2 is a diagram of a dehalogenation and cleavage reaction according to formula embodiments of the present invention with an ether or thioether linkage.

FIG. 2 provides a general class of compounds (Formula 2) according to embodiments of the present invention. According to these embodiments, a compound ($R_1$—YH), such as a drug compound, may be bonded or linked by an ether or thioether linkage to a halogenated phenol ring to form part of a compound of the present invention. The ether or thioether linkage (—Y—) may be an ether linkage if Y is an oxygen atom and the —YH group is a hydroxyl group, or a thioether linkage if Y is a sulfur atom and the —YH group is a sulfhydryl group. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring).

The halogen X may be selected from either iodine (I) or bromine (Br), but generally may not include fluorine (F) or chlorine (Cl). According to these embodiments, the ether or thioether linkage (—Y—) is positioned in the para position relative to the halogen X on the phenol ring and in the meta position relative to the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. According to some alternative embodiments, one, two, or three of these variable substituents may be hydrogen. Furthermore, combinations of these other substituents, $R_2$, $R_3$, and $R_4$, present on the phenol ring may themselves form fused rings with the halogenated phenol ring.

According to these embodiments in FIG. 2, when a compound of Formula 2 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the ether or thioether linkage (—Y—) between the drug compound and the phenol ring to release the drug compound ($R_1$—YH), and the ether or thioether linkage is replaced by a hydroxyl group on the phenol ring. In addition to release of a proton ($H^+$; not shown), a halide ($X^-$) and drug compound, a benzenetriol-based or hydroxyhydroquinone-based compound (e.g., 1,2,4-benzenetriol) may be formed. However, the exact formula name for this product of the reaction will depend on the identity of the additional substituents, $R_2$, $R_3$, and $R_4$. Indeed, one or more of these additional substituents may be hydroxyl groups.

Figure 3:
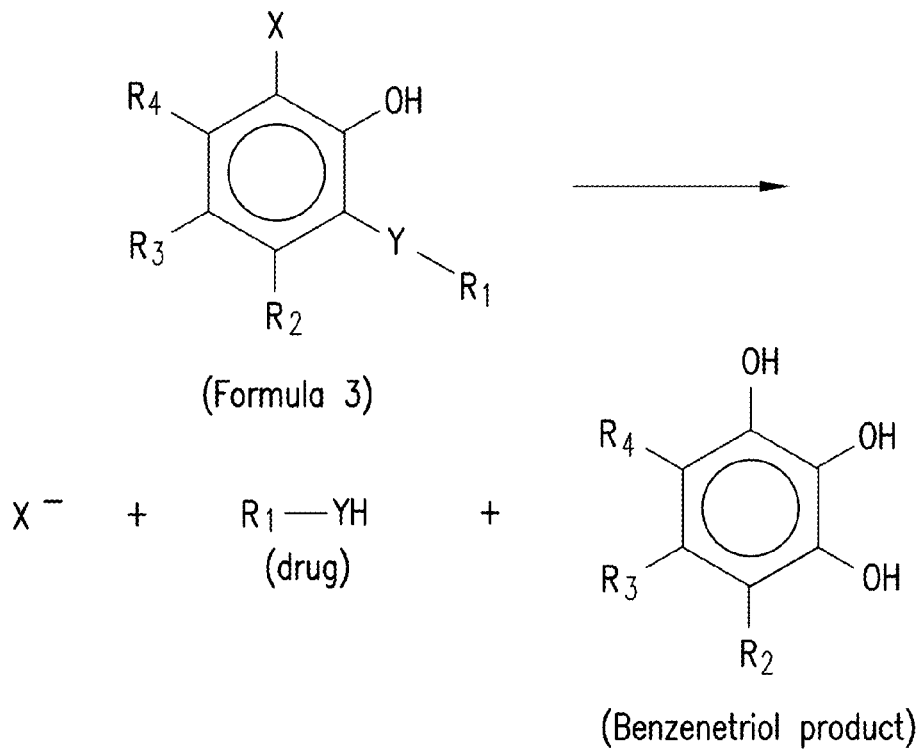
FIG. 3 is a diagram of a dehalogenation and cleavage reaction according to formula embodiments of the present invention with an ether or thioether linkage.

FIG. 3 provides a general class of compounds (Formula 3) according to embodiments of the present invention. According to these embodiments, a compound ($R_1$—YH), such as a drug compound, may be bonded or linked by an ether or thioether linkage to a halogenated phenol ring to form part of a compound of the present invention. The ether or thioether linkage (—Y—) may be an ether linkage if Y is an oxygen atom and the —YH group is a hydroxyl group or a thioether linkage or group if Y is a sulfur atom and the —YH group is a sulfhydryl group. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl). According to these embodiments, the ether or thioether linkage (—Y—) is positioned in the meta position relative to the halogen X on the phenol ring and in the ortho position relative to the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. According to some alternative embodiments, one, two, or three of these variable substituents may be hydrogen. Furthermore, combinations of these other substituents, $R_2$, $R_3$, and $R_4$, present on the phenol ring may themselves form fused rings with the halogenated phenol ring.

According to these embodiments in FIG. 3, when a compound of Formula 3 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the ether or thioether linkage (—Y—) between the drug compound and the phenol ring to release the drug compound ($R_1$—YH), and the ether or thioether linkage is replaced by a hydroxyl group on the phenol ring. In addition to release of a proton ($H^+$; not shown), a halide ($X^-$) and drug compound, a benzenetriol-based compound (e.g., 1,2,3-benzenetriol or pyrogallol) may be formed. However, the exact formula name for this product of the reaction will depend on the identity of additional substituents, $R_2$, $R_3$, and $R_4$.

Figure 4:
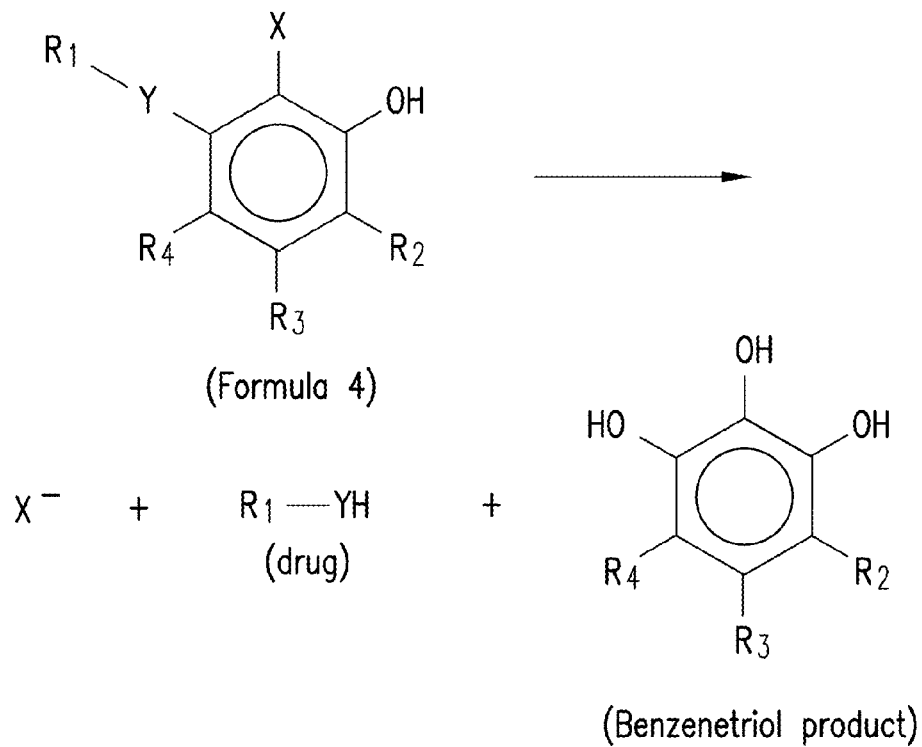
FIG. 4 is a diagram of a dehalogenation and cleavage reaction according to formula embodiments of the present invention with an ether or thioether linkage.

FIG. 4 provides a general class of compounds (Formula 4) according to embodiments of the present invention. According to these embodiments, a compound ($R_1$—YH), such as a drug compound, may be bonded or linked by an ether or thioether linkage to a halogenated phenol ring to form part of a compound of the present invention. The ether or thioether linkage (—Y—) may be an ether linkage if Y is an oxygen atom and the —YH group is a hydroxyl group or a thioether linkage if Y is a sulfur atom and the —YH group is a sulfhydryl group. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl). According to these embodiments, the ether or thioether linkage (—Y—) is positioned in the ortho position relative to the halogen X on the phenol ring and in the meta position relative to the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. According to some alternative embodiments, one, two, or three of these variable substituents may be hydrogen. Furthermore, combinations of these other substituents, $R_2$, $R_3$, and $R_4$, present on the phenol ring may themselves form fused rings with the halogenated phenol ring.

According to these embodiments in FIG. 4, when a compound of Formula 4 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the ether or thioether linkage (—Y) between the drug compound and the phenol ring to release the drug compound ($R_1$—YH), and the ether or thioether linkage is replaced by a hydroxyl group on the phenol ring. In addition to release of a proton ($H^+$; not shown), a halide ($X^-$) and drug compound, a benzenetriol-based compound (e.g., 1,2,3-benzenetriol or pyrogallol) may be formed. However, the exact formula name for this product of the reaction will depend on the identity of additional substituents, $R_2$, $R_3$, and $R_4$.

According to embodiments of the present invention, two or more compounds, such as drug compounds, may be bonded or linked by an ether or thioether linkage to the same halogenated phenol ring. According to these embodiments, two or more compounds may be concertedly or simultaneously (or nearly simultaneously) released upon exposure of the halogenated phenol ring to free radicals and/or oxidizing agents.

In the case of drug compounds, such an approach may have utility for co-administering two or more drug compounds to a site of disease or inflammation within the body of an individual as part of a combined therapy, for example when simultaneous exposure of a tissue, cells, tissue/cell environment, infectious agent, etc., at the site of disease or inflammation to the two or more drug compounds has a particular benefit or synergistic effect compared to the separate taking or administration of the drug compounds.

Figure 5:
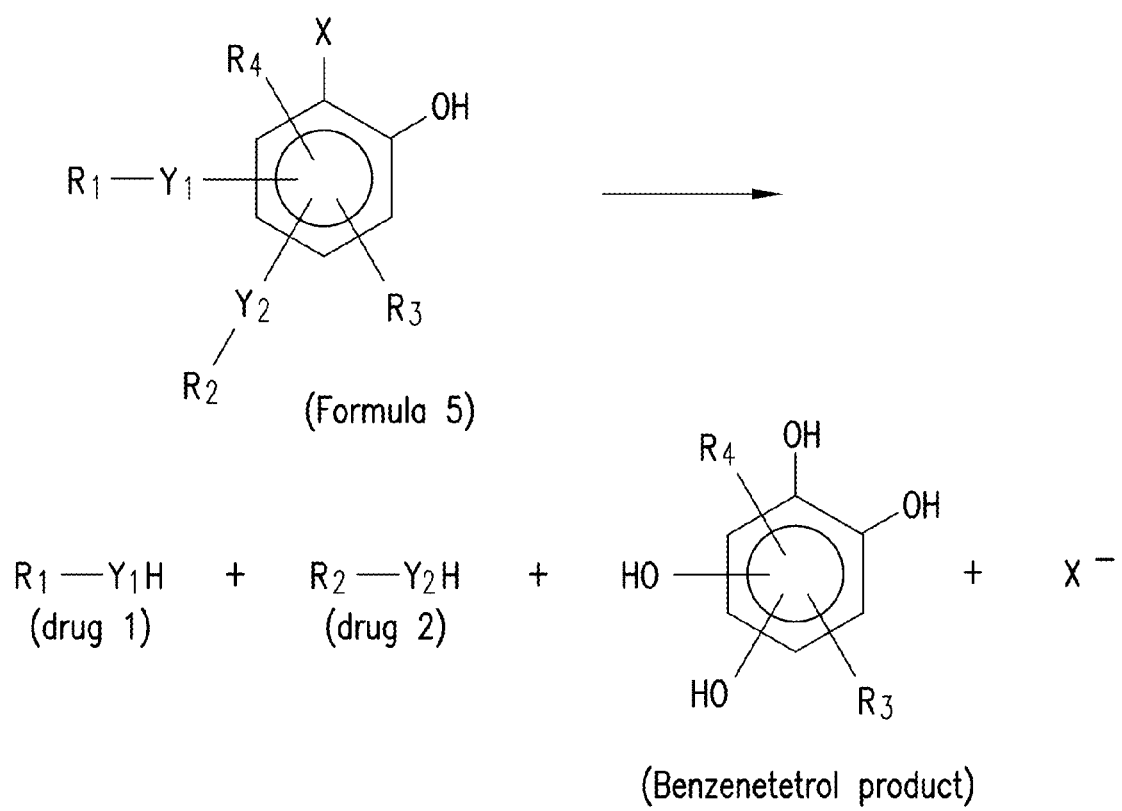
FIG. 5 is a diagram of a dehalogenation and cleavage reaction according to formula embodiments of the present invention with two drugs ether or thioether linked to the ring.

FIG. 5 provides a general class of compounds (Formula 5) according to embodiments of the present invention. According to these embodiments, two compounds ($R_1$—$Y_1H$ and $R_2$—$Y_2H$), such as two drug compounds, may each be bonded or linked by an ether or thioether linkage to a halogenated phenol ring to form parts of a compound of the present invention. The ether or thioether linkages (—$Y_1$— and —$Y_2$—) may each be an ether linkage if $Y_1$ or $Y_2$ is an oxygen atom and the —$Y_1H$ group or the —$Y_2H$ group is a hydroxyl group, or a thioether linkage if $Y_1$ or $Y_2$ is a sulfur atom and the —$Y_1H$ group or the —$Y_2H$ group is a sulfhydryl group. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl).

According to these embodiments, the ether or thioether linkages (—$Y_1$— and —$Y_2$—) may be positioned anywhere on the phenol ring not occupied by the ortho-positioned hydroxyl group and halogen (X) (i.e., on any of the remaining carbons of the phenol ring). Similarly, additional substituents $R_3$ and $R_4$ may be positioned anywhere on the phenol ring not occupied by the ortho-positioned hydroxyl group and halogen (X) (i.e., on any of the remaining carbons of the phenol ring). The identity of each of the additional substituents, $R_3$ and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_3$ and $R_4$ may be any halogen atom. According to some alternative embodiments, one or both of these variable substituents may be hydrogen. Furthermore, substituents $R_3$ and $R_4$ may together form a fused ring with the halogenated phenol ring. In all of the figures, the drawing of a bond line between carbons of a benzene or phenol ring means that such a bond may involve (i.e., be bonded to) any of the remaining carbons of the ring (in the alternative) that are not fixedly or otherwise occupied or bonded to another substituent or group.

According to embodiments of the present invention in FIG. 5, when a compound of Formula 5 comes in contact with an oxidizing agent or free radical or is present in an oxidizing and/or free radical containing environment, the halogen (X) is cleaved and removed from the phenol ring and replaced with a hydroxyl group. This free radical attack or oxidation of the phenol ring further results in the breaking or cleavage of the ether or thioether linkages (—$Y_1$— and —$Y_2$—) between the drug compound and the phenol ring to release the drug compounds ($R_1$—$Y_1H$ and $R_2$—$Y_2H$), and each of the ether or thioether linkages is replaced by a hydroxyl group on the phenol ring. In addition to release of a halide ($X^-$) and drug compounds, a benzenetetrol-based compound (e.g., 1,2,3,4-benzenetetrol, 1,2,3,5-benzenetetrol, or 1,2,4,5-benzenetetrol) may be formed. However, the exact formula name for this product of the reaction will depend on the identity of the additional substituents, $R_3$ and $R_4$.

According to embodiments of the present invention, two or more compounds, such as drug compounds, may be bonded or linked by an ether or thioether linkage to two or more halogenated phenol rings. According to these embodiments, two or more compounds may be released in a sequential fashion upon exposure of the halogenated phenol rings to free radicals and/or oxidizing agents. In the case of drug compounds, such an approach may have utility for delivering or co-administering two or more drug compounds to a site of disease or inflammation within the body of an individual as part of a combined therapy, especially when an ordered or sequential exposure of a tissue, cells, tissue or cell environment, infectious agent, etc., at the site of disease or inflammation to the two or more drug compounds has a particular benefit or synergistic effect compared to the separate taking or administration of the drug compounds. Such an approach may be useful as an alternative to treatments involving multivalent treatments or cocktails of drugs and for synergistic or complementary drug combinations. There may also be an advantage to attaching drug compounds to two or more ether or thioether linked halogenated phenol rings. For example, there may be an advantage to attaching drug compounds to two or more ether or thioether linked halogenated phenol rings to improve chemical synthesis (e.g., to overcome steric hindrance if the two drug compounds are attached to the same phenol ring) or reactive properties. Release of a first drug compound may have a particular effect that improves the subsequent impact of a second drug compound at the site. For example, release of the first drug compound may render the target of the drug compounds (e.g., tissue, cells, tissue or cell environment, infectious agents, etc.) at the site of disease or inflammation more vulnerable, susceptible or sensitive to treatment by the second compound.

Figure 6A:
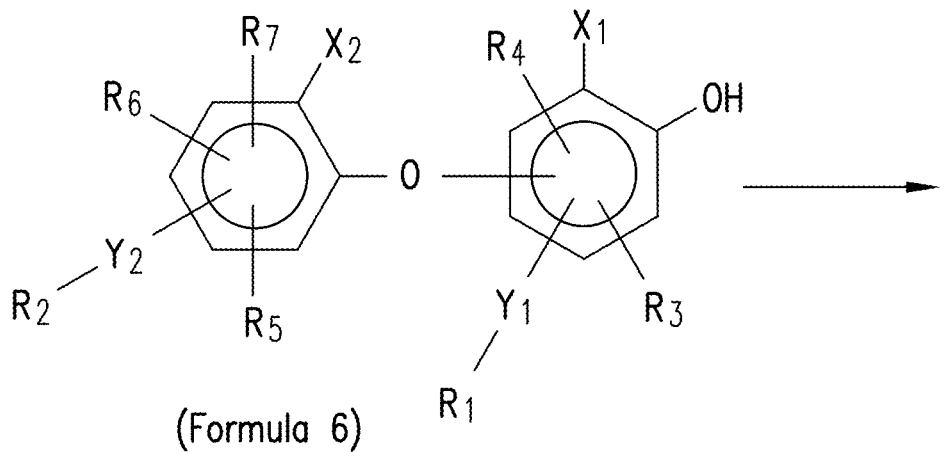
FIG. 6A is a diagram of a first dehalogenation and cleavage reaction of a two-step reaction according to formula embodiments of the present invention for sequential release of two drugs ether or thioether linked to the ring.
Figure 6A:
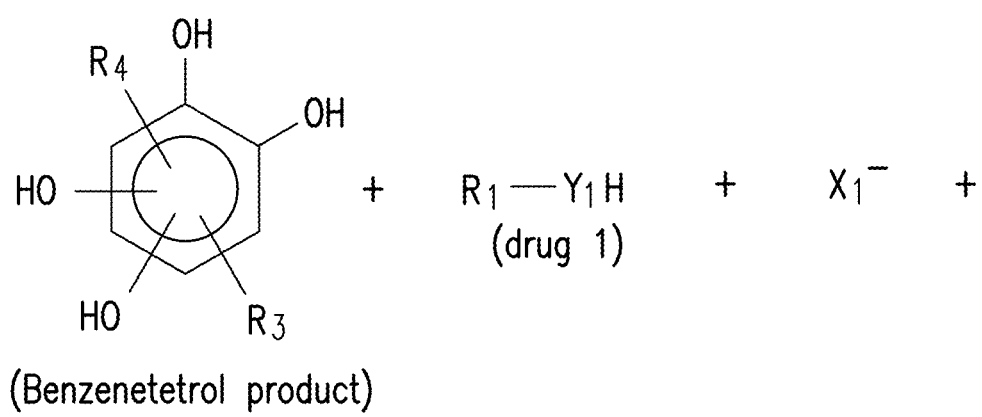
Figure 6A:
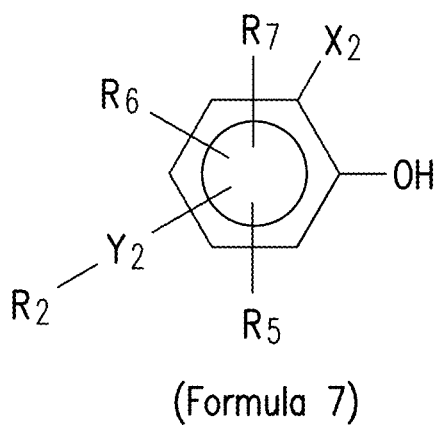

FIG. 6A provides a general class of compounds (Formula 6) according to embodiments of the present invention. According to these embodiments, two conjugated compounds, such as two drug compounds, consisting of a first compound ($R_1$—$Y_1H$) and a second compound ($R_2$—$Y_2H$), may each be bonded or conjugated by ether or thioether linkage to two halogenated phenol rings including a first phenol ring and a second phenol ring, with the first phenol ring and the second phenol ring linked together by an ether (—O—) linkage. The first compound ($R_1$—$Y_1H$) is bonded by an ether or thioether linkage to the first phenol ring, and the second compound ($R_2$—$Y_2H$) is bonded by an ether or thioether linkage to a second phenol ring, such that the first and second compounds form part of the compound of the present invention. Ether or thioether linkage (—$Y_1$—) on the first phenol ring may be either an ether linkage if $Y_1$ is an oxygen atom and the —$Y_1H$ group is a hydroxyl group or a thioether linkage if $Y_1$ is a sulfur atom and the —$Y_1H$ group is a sulfhydryl group. Ether or thioether linkage (—$Y_2$—) on the second phenol ring may be either an ether linkage if $Y_2$ is an oxygen atom and the —$Y_2H$ group is a hydroxyl group or a thioether linkage if $Y_2$ is a sulfur atom and the —$Y_2H$ group is a sulfhydryl group.

According to these embodiments in FIG. 6A, substituents $X_1$ and $X_2$ of Formula 6 are each halogens present on the first and second phenol rings, respectively, with each halogen $X_1$ and $X_2$ in the ortho position relative to either the hydroxyl group (—OH) on the first phenol ring or the ether linkage on the second phenol ring (i.e., $X_1$ is a halogen bonded to a carbon of the first phenol ring that is adjacent to a carbon of the first phenol ring that is bonded to the hydroxyl group, and $X_2$ is a halogen bonded to a carbon of the second phenol ring that is adjacent to a carbon of the second phenol ring that is linked by an ether linkage to the first phenol ring). Each of the halogens $X_1$ and $X_2$ may be either iodine (I) or bromine (Br), but generally may not include fluorine (F) or chlorine (Cl).

According to these embodiments in FIG. 6A, ether or thioether linkage (—$Y_1$—) as well as additional substituents $R_3$ and $R_4$ may each be positioned on any of the remaining three carbons of the first phenol ring that are not occupied by the ortho-positioned hydroxyl group (—OH) and halogen $X_1$ or by the ether linkage connecting the first and second phenol ring. Ether or thioether linkage (—$Y_2$—) as well as additional substituents $R_5$, $R_6$, and $R_7$ may each be positioned on any of the remaining four carbons of the second phenol ring that is not occupied by the halogen $X_2$ or by the ether linkage connecting the first and second phenol ring. The identity of each of the additional substituents, $R_3$, $R_4$, $R_5$, $R_6$, and $R_7$, may vary and may include, for example, a hydrogen, a hydroxyl, a sulfhydryl, an alkyl, a halogen, an amino, a nitro, etc., groups. Unlike halogens $X_1$ or $X_2$, substituents $R_3$, $R_4$, $R_5$, $R_6$, and $R_7$ may be any halogen atom. According to some alternative embodiments, one, two, three, four or five of these variable substituents may be hydrogen. Furthermore, any combination of substituents $R_3$ and $R_4$ and/or any combination of substituents $R_5$, $R_6$, and $R_7$ may together form a fused ring with their respective halogenated phenol ring.

According to embodiments of the present invention, when a compound of Formula 6 comes in contact with an oxidizing agent or free radical or is present in an oxidizing and/or free radical containing environment, the halogen $X_1$ of the first phenol ring may be cleaved from the first phenol ring and replaced with a hydroxyl group. This free radical attack or oxidation of the first phenol ring may further result in the breaking or cleavage of the ether linkage (—O—) between the first and second phenol rings and the ether or thioether linkage (—$Y_1$—) to release the first drug compound $R_1Y_1H$ and the second phenol ring from the first phenol ring. Both the ether linkage (—O—) between the first and second phenol rings and the ether or thioether linkage (—$Y_1$—) between the first phenol ring and the first drug compound are replaced on the first phenol ring by a hydroxyl group. In addition to the release of a halide ($X_1^-$), first drug compound, and second phenol ring, a benzenetetrol-based compound (e.g., 1,2,3,4-benzenetetrol, 1,2,3,5-benzenetetrol, or 1,2,4,5-benzenetetrol) may be formed. However, the exact formula name for this product will depend on the identity of the additional substituents, $R_3$ and $R_4$. As a product of this reaction, the second drug compound will remain bonded to the second phenol ring via the second ether or thioether linkage (—$Y_2$—), and the ether linkage (—O—) between the first and second phenol rings will also be replaced by a hydroxyl group on the second phenol ring as shown in Formula 7.

According to the embodiments shown in FIG. 6A, one of the products of the reaction is the second phenol ring bonded to the second drug compound (Formula 7). The second drug compound may then be released in a second chemical event when a compound of Formula 7 comes in contact with an oxidizing agent or free radical, or is present in an oxidizing and/or free radical containing environment. Therefore, a compound of Formula 6 has the effect of releasing a first drug compound and a second drug compound sequentially in time with the first drug compound being released during a first chemical event triggered by an oxidizing agent or free radical and the second drug compound being released subsequently during a second chemical event triggered by another oxidizing agent or free radical.

Figure 6B:
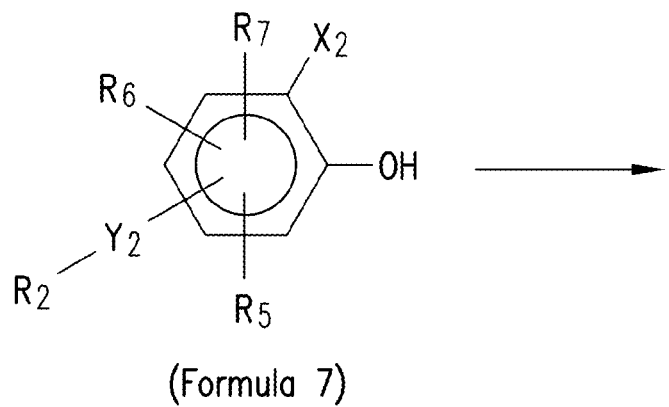
FIG. 6B is a diagram of a second dehalogenation and cleavage reaction of a two-step reaction according to formula embodiments of the present invention for sequential release of two drugs ether or thioether linked to the ring.
Figure 6B:
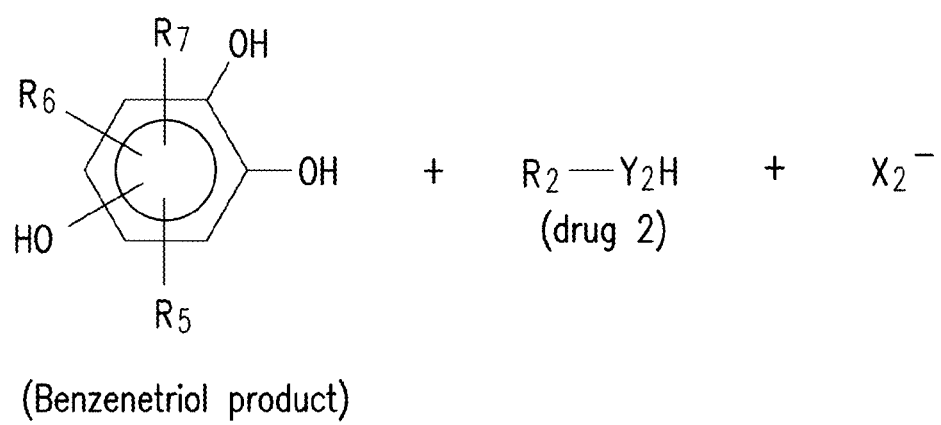

According to the embodiments shown in FIG. 6B, when a compound of Formula 7 comes in contact with an oxidizing agent or free radical, the halogen $X_2$ of the second phenol ring is cleaved from the second phenol ring and replaced with a hydroxyl group. This free radical attack or oxidation of the second phenol ring further results in the breaking or cleavage of the ether or thioether linkage (—$Y_2$—) between the second phenol ring and the second drug compound to release the second drug compound $R_2$—$Y_2H$ from the second phenol ring, and the ether or thioether linkage (—$Y_2$—) is replaced by a hydroxyl group on the second phenol ring. In addition to the release of a halide ($X_2^-$) and second drug compound, a benzenetriol-based or hydroxyhydroquinone-based compound (e.g., 1,2,4-benzenetriol or 1,2,3-benzenetriol) may be formed. However, the exact formula name for this product will depend on the identity of the additional substituents, $R_5$, $R_6$, and $R_7$.

Figure 7:
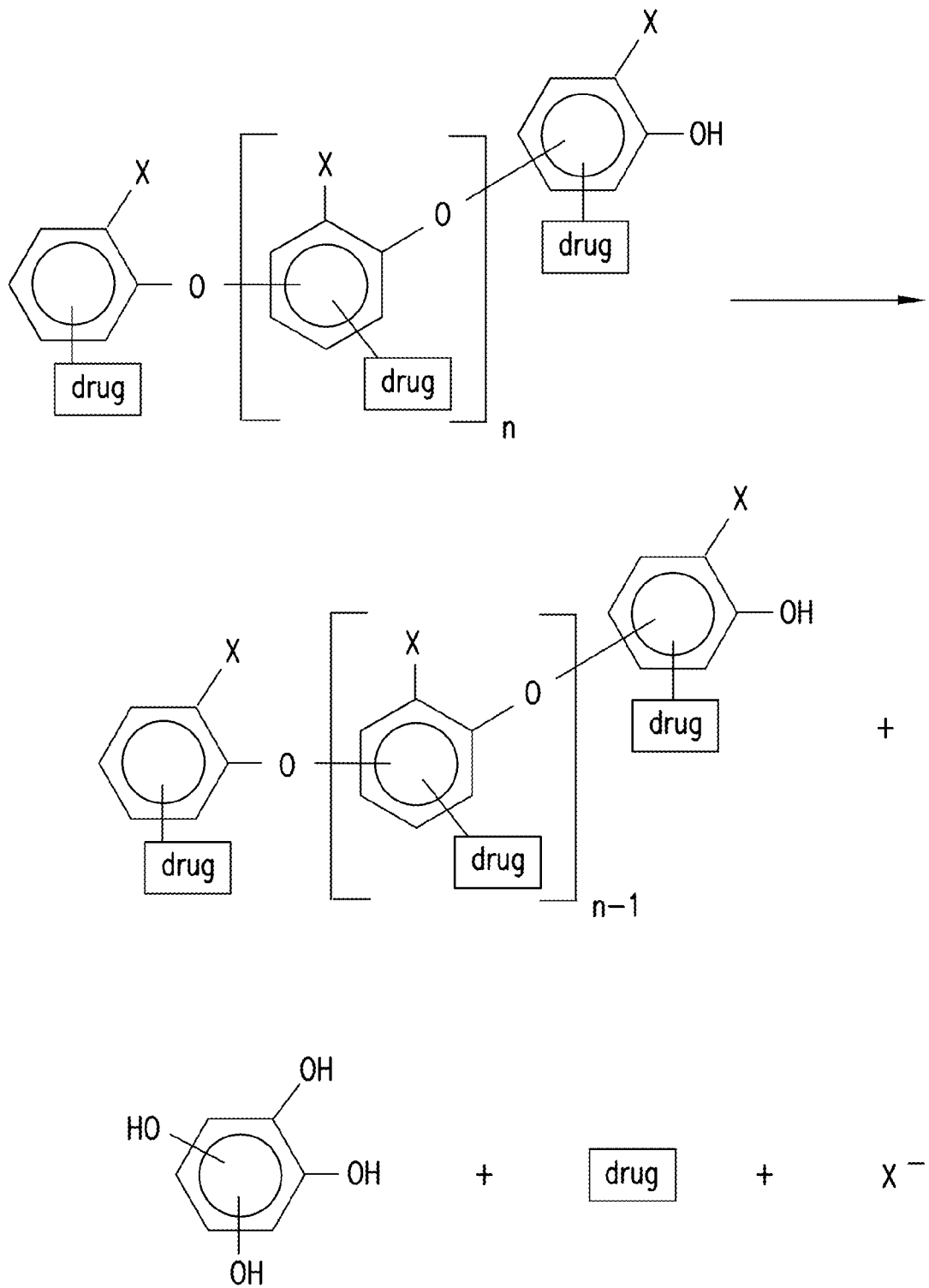
FIG. 7 is a diagram of a series of dehalogenation and cleavage reactions to occur with a formula of polymer embodiments of the present invention, which may result in successive release of drugs from respective monomers.

As supported by the general classes of compounds in FIGS. 6A and 6B, embodiments of the present invention may potentially include polymers of halogenated phenol ring units of any length with each unit of the polymer ether or thioether linked to a drug compound and linked to its neighboring unit(s) of the polymer by an ether linkage. As shown conceptually in FIG. 7, drug compounds may be released sequentially (one at a time) through successive reaction events or steps triggered by exposure of the polymer to oxidizing agents and/or free radicals. Drug compounds are shown in FIG. 7 bonded to each of the units of the polymer. These drug compounds, which form part of the polymer compound of the present invention, are released sequentially to yield a polymer of shorter length along with a benzenetetrol- or benzenetriol-based product and a halide ($X^-$). Although the other substituents on each unit of the polymer shown in FIG. 7 are depicted as being hydrogens, these other substituents may also vary similarly as shown described above in reference to FIG. 6 and Formula 6 therein. As an alternative to the general class of formulas encompassed by FIGS. 6 and 7, the ether or thioether linkages may instead be replaced with the other types of linkages (e.g., carbonyl linkage, etc.) as described further herein with the other substituents of these formulas possibly remaining the same.

According to embodiments of the present invention, any combination of the same, similar, or different drug compounds may be bonded to the units of the polymer. According to some embodiments, not all units of a polymer need to be bonded (i.e., ether or thioether linked) to a compound, such as a drug compound. These "empty" units of the polymer may be used to create a desired spacing between units bonded to one or more compound(s) or drug compound(s) to achieve a preferred timing or sustained release of the compound(s) or drug compound(s). For example, the number of "empty" polymer units ahead of unit(s) bonded to drug compound(s) may be used to engineer the timing or delay of release for the drug compound(s) after its initial administration to an individual, or alternatively, the spacing between units of a polymer bonded to drug compound(s) may be used to engineer the relative timing of release for two or more drug compounds. Polymer compounds according to these embodiments may range greatly in size and may include polymers of 2-200 units in length, or alternatively polymers of 2-100 units, 2-50 units, 2-25 units, 2-10 units, or 2-5 units in length, but longer polymers are also possible. According to some embodiments, the polymers may have a minimum of three (3) units in a range having the same upper limits. Likewise, the amount of spacing or number of "empty" units may vary widely and may include continuous lengths of 1-100, 1-50, 1-10, etc., but longer spacings or lengths of empty units may also be used. The number of middle units (n) may correspond to these total lengths. According to FIG. 7, if the total number of units (i.e., total length) is two (2), then n would equal zero (0). If the total number of units was three (3), then n would equal one (1), and so on.

Another advantage of these embodiments of the present invention is that by combining one or more drug compound(s) on the same molecule, polymer or chain, such as in FIGS. 5-7, the relative amounts of the drug compound(s) on the molecule may be controlled, and the relative amounts of these drugs formed or liberated by the dehalogenation reaction and thus delivered to high FROS target tissues may be controlled stoichiometrically.

According to embodiments of the present invention, such as those presented in the figures above, the identity and position of substituents on the halogentated phenol ring including, for example, the halogen (X) at the ortho position of the phenol ring relative to the hydroxyl group as well as the additional substituents $R_2$, $R_3$, etc., may be chosen to achieve desired characteristics. For example, the identity and position of substituents on the halogentated phenol ring may be chosen to adjust the sensitivity with which the linkage (e.g., ether linkage, etc.) between a phenol ring and a (drug) compound is broken or cleaved in response to free radicals or oxidative agents. Without being bound by theory, it is believed that stabilizing the phenol ring will generally result in lowering the sensitivity of cleavage and raising the threshold for cleavage and release of a drug compound. Generally speaking, it is believed that increasing the number and/or strength of electron withdrawing groups on the phenol ring of a halogenated phenol compound may result in destabilizing the phenol ring, while increasing the number and/or strength of electron donating groups on the phenol ring of a halogenated phenol compound may result in stabilizing the phenol ring. For example, increasing the number of halogen substituents may destabilize the phenol ring and lower the threshold (i.e., increase the sensitivity) for cleavage of the ether or thioether linkage and release of a drug compound. Using bromine (Br) for the halogen (X) of the phenol ring at the ortho position relative to the hydroxyl group may have the effect of stabilizing the halogenated phenol ring (thus raising the threshold and lowering the sensitivity) compared to iodine (I). Other possibilities include the use of amino groups, which may destabilize the ring and lower the threshold of sensitivity, or the use of nitro groups, which may stabilize the ring and raise the threshold of sensitivity. Also, as stated above, linking the (drug) compound at the para position relative to the hydroxyl group on the halogenated phenol ring may result in a higher sensitivity of cleavage relative to linkages at the meta and ortho positions.

Although these principles are proposed as possible bases for modifying or designing the sensitivity of cleavage for a halogenated phenol compound in response to free radicals or oxidative stress, the precise effects of any given substituent on the sensitivity of cleavage for a particular halogenated phenol compound may depend greatly on the full chemical formula of the halogenated phenol compound and the circumstances under which the compound is used. To determine the sensitivity of cleavage directly for a particular halogenated phenol compound, empirical or trial-and-error methods may be used. For example, the amount of detectable product(s) (e.g., including quinone products or halides) of the reaction may be measured in vitro under controlled conditions to determine the sensitivity of cleavage for a given halogenated phenol compound.

Figure 8A:
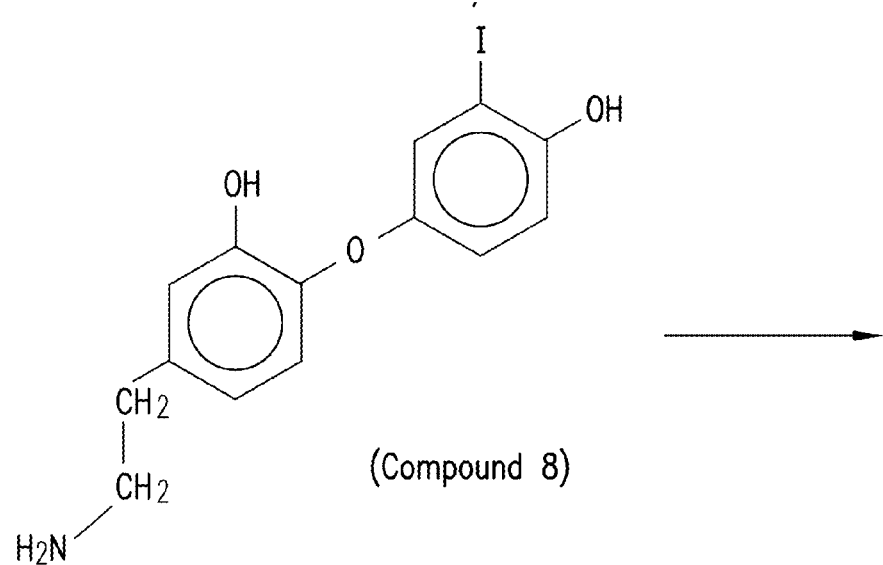
FIG. 8A is a diagram of a dehalogenation and cleavage reaction according to an embodiment of the present invention for the formation of dopamine.
Figure 8A:
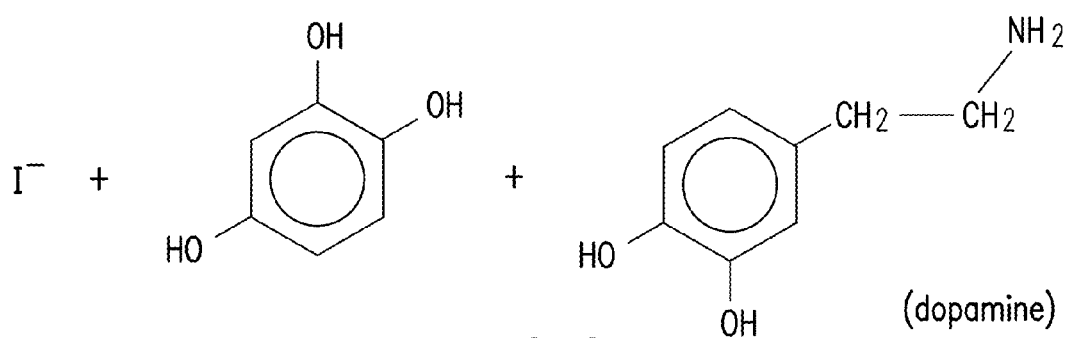

FIG. 8A shows an example embodiment of the present invention for a 3-hydroxy-3'-iodo-L-thyronamine or 1-ethylamine-3-hydroxy-3'-iodo-4'-hydroxy-diphenyl ether compound (Compound 8) that may be converted into a 3-hydroxytyramine compound (i.e., dopamine). According to this embodiment, when Compound 8 comes in contact with an oxidizing agent or free radical, or is present in an oxidizing and/or free radical containing environment, the iodine (I) of the outer phenol ring is cleaved and replaced with a hydroxyl group. This free radical attack or oxidation of the outer phenol ring further results in the breaking or cleavage of the ether linkage (—O—) between the inner and outer phenol rings to release the dopamine drug compound. In addition to the release of dopamine and an iodide ($I^-$), a benzenetriol-based compound (e.g., 1,2,4-benzenetriol or 1,2,3-benzenetriol) is formed. Formation of dopamine in the brain may be effective in treating brain disorders, such as Parkinson's disease.

Figure 8B:
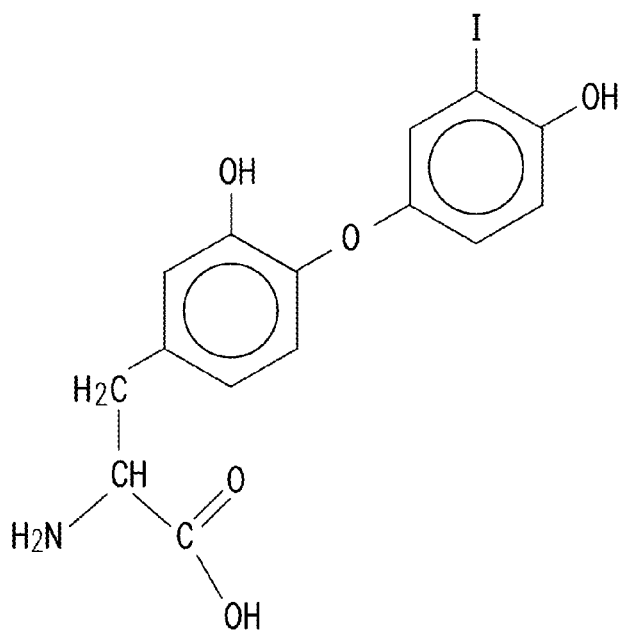
FIG. 8B is a formula of a starting compound according to an embodiment of the present invention for the formation of L-DOPA.

As another alternative shown in FIG. 8B, a starting compound may be a 3-hydroxy-3'-iodo-L-thyronine compound that may be used to release a 3,4-dihydroxy compound (i.e., L-DOPA) in FROS-containing tissue. The L-DOPA product of this reaction may then be further converted into dopamine via the activity of a DOPA decarboxylase enzyme present in a targeted tissue where the L-DOPA compound is formed. According to another similar embodiment, the outer phenol ring may comprise two or more iodine (or other halogen) atoms instead of one. For example, the starting compound may be a 3-hydroxy-3',5'-diiodo-thyronine compound.

Figure 9:
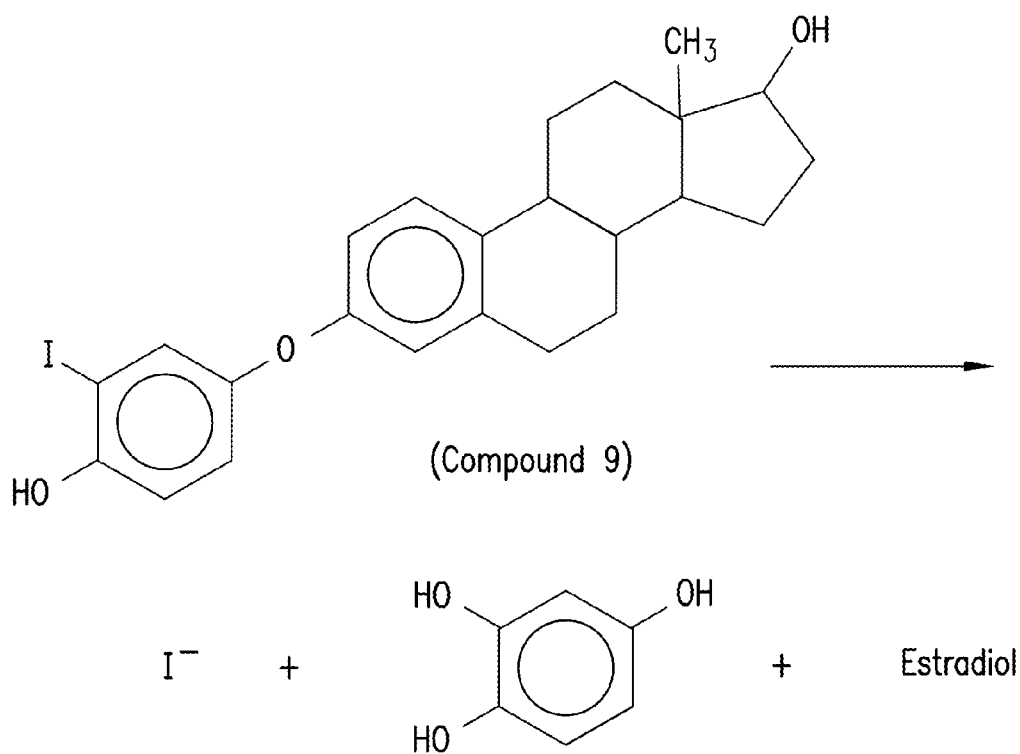
FIG. 9 is a diagram of a dehalogenation and cleavage reaction according to an embodiment of the present invention for the formation of estradiol.

FIG. 9 shows an example embodiment of the present invention for an iodo-phenol compound linked by an ether linkage to an Estradiol drug to form part of the compound (Compound 9). According to this embodiment, when the Estradiol-linked iodo-phenol compound comes in contact with an oxidizing agent or free radical, or is present in an oxidizing and/or free radical containing environment, the iodine (I) of the phenol ring is cleaved and replaced with a hydroxyl group. This free radical attack or oxidation of the phenol ring further results in the breaking or cleavage of the ether linkage (—O—) between the phenol ring and the Estradiol drug compound to release the Estradiol drug compound. In addition to the release of Estradiol and an iodide ($I^-$), a benzenetriol-based or hydroxyhydroquinone-based compound (e.g., 1,2,4-benzenetriol or 1,2,3-benzenetriol) is formed.

Figure 10:
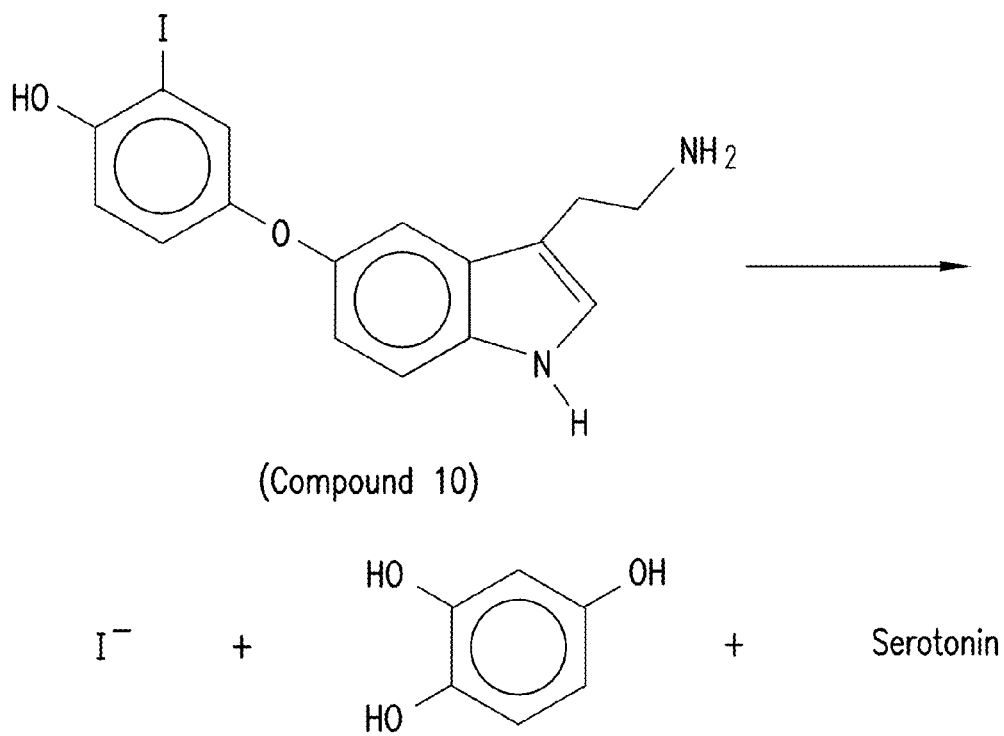
FIG. 10 is a diagram of a dehalogenation and cleavage reaction according to an embodiment of the present invention for the formation of serotonin.

FIG. 10 shows an example embodiment of the present invention for an iodo-phenol compound linked by an ether linkage to serotonin to form part of the compound (Compound 10). As an alternative to Compound 10, this serotonin-releasing compound may be 3,5-diiodo-4-hydroxy-(N-acetyl tryptamine)-1,5'-diphenyl ether. According to this embodiment, when the serotonin-linked iodo-phenol compound comes in contact with an oxidizing agent or free radical, or is present in an oxidizing and/or free radical containing environment, the iodine (I) of the phenol ring is cleaved and replaced with a hydroxyl group. This free radical attack or oxidation of the phenol ring further results in the breaking or cleavage of the ether linkage (—O—) between the phenol ring and the serotonin drug compound to release the serotonin drug compound. In addition to the release of serotonin and an iodide ($I^-$), a benzenetriol-based or hydroxyhydroquinone-based compound (e.g., 1,2,4-benzenetriol or 1,2,3-benzenetriol) is formed.

Figure 11A:
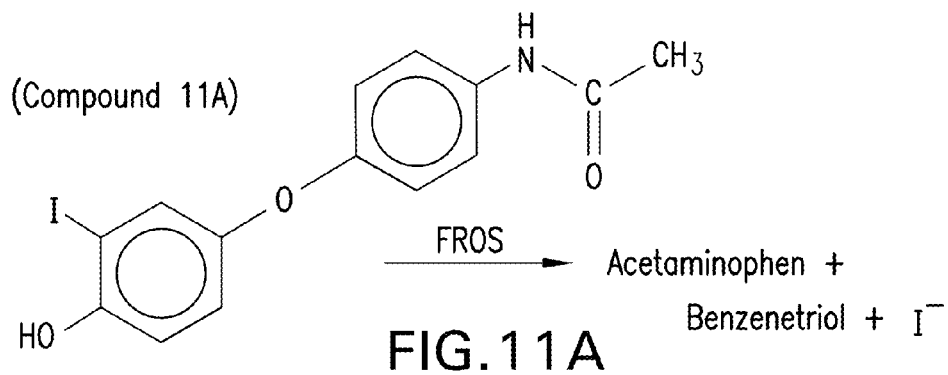
FIG. 11A is a diagram of a dehalogenation and cleavage reaction according to an embodiment of the present invention for the formation of acetaminophen.
Figure 11B:
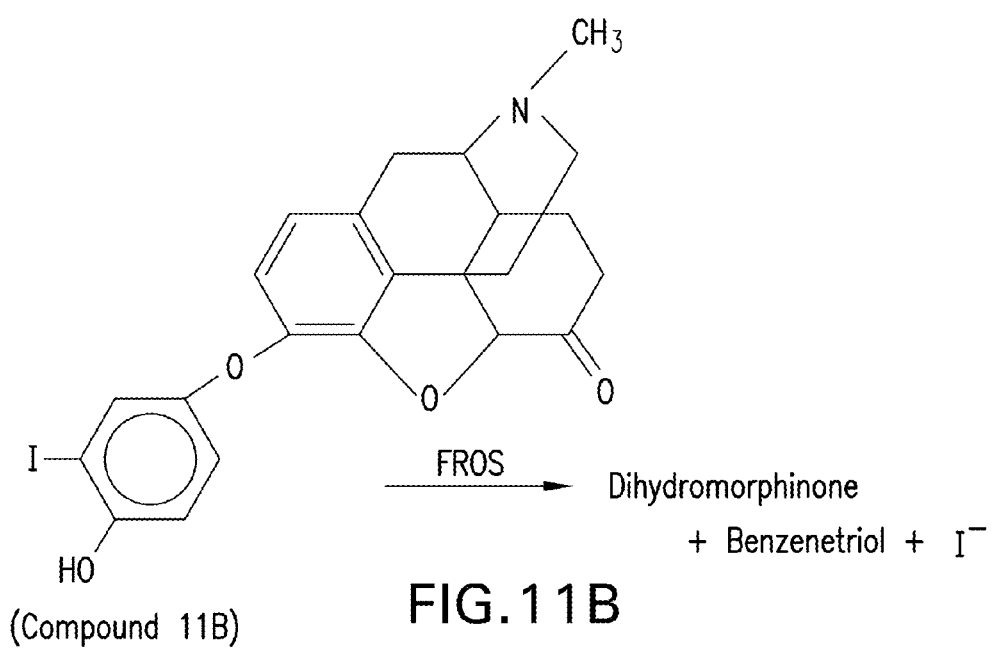
FIG. 11B is a diagram of a dehalogenation and cleavage reaction according to an embodiment of the present invention for the formation of dihydromorphinone.

FIG. 11 shows some additional examples of starting compounds that may be used to form common drug compounds as a result of the dehalogenation and cleavage reaction. FIG. 11A shows a drug, acetaminophen, ether linked to a halogenated phenol ring. Upon cleavage in the presence of FROS, acetaminophen is formed along with a 1,2,4-benzenetriol and a halide. FIG. 11B shows another drug, dihydromorphinone or DILAUDID®, ether linked to a halogenated phenol ring. Upon cleavage in the presence of FROS, the dihydromorphinone is formed along with a 1,2,4-benzenetriol and a halide.

Figure 11C:
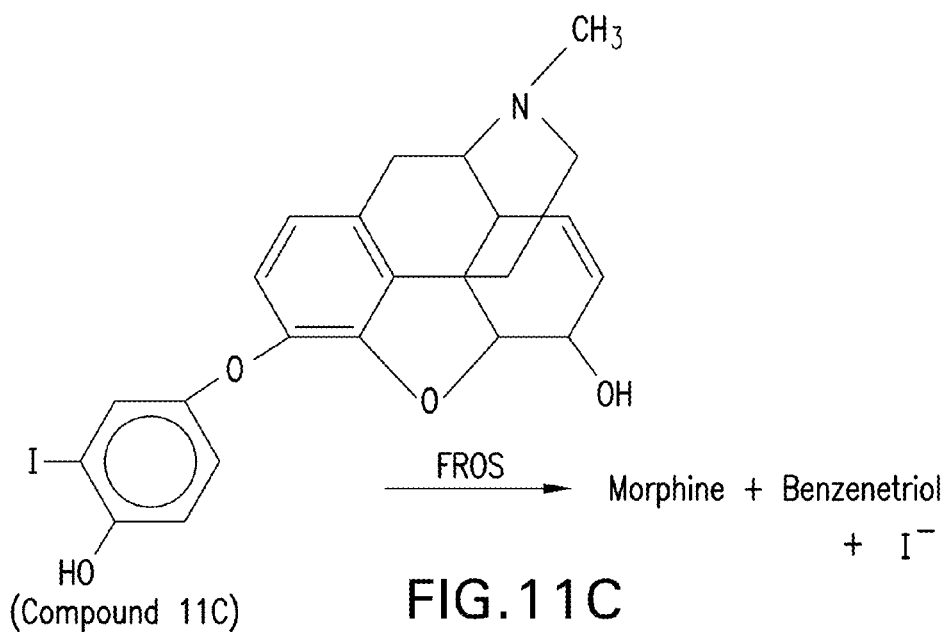
FIG. 11C is a diagram of a dehalogenation and cleavage reaction according to an embodiment of the present invention for the formation of morphine.

FIG. 11C shows yet another drug, morphine, ether linked to a halogenated phenol ring. Upon cleavage in the presence of FROS, morphine is formed along with a 1,2,4-benzenetriol and a halide. These compounds may be useful in treating specific sites of inflammation, injury, infection or disease that may be associated with pain or discomfort by targeted delivery of the analgesic.

Figure 12:
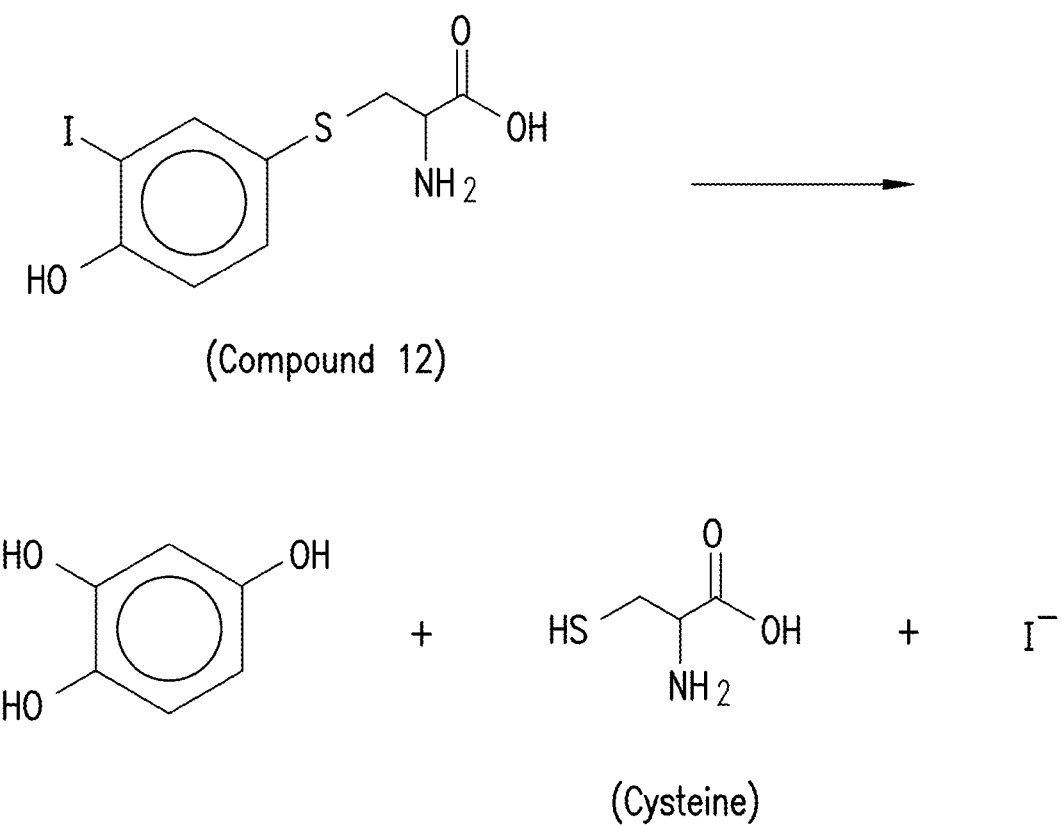
FIG. 12 is a diagram of a dehalogenation and cleavage reaction according to an embodiment of the present invention for the formation of cysteine.

FIG. 12 shows an example embodiment of the present invention for an iodo-phenol compound linked by a thioether linkage to the amino acid cysteine to form part of the compound (Compound 12). This example is provided in part as an example to demonstrate how molecules containing a sulfhydryl group may be linked to a halogenated phenol group by a thioether linkage according to embodiments of the present invention. According to this example, when the cysteine-linked iodo-phenol compound comes in contact with an oxidizing agent or free radical, or is present in an oxidizing and/or free radical containing environment, the iodine (I) of the phenol ring is cleaved and replaced with a hydroxyl group. This free radical attack or oxidation of the phenol ring further results in the breaking or cleavage of the thioether linkage (—S—) between the phenol ring and cysteine to release the cysteine molecule. In addition to the release of the amino acid cysteine and an iodide ($I^-$), a benzenetriol-based or hydroxy-hydroquinone-based compound (e.g., 1,2,4-benzenetriol or 1,2,3-benzenetriol) is also formed.

Figure 13:
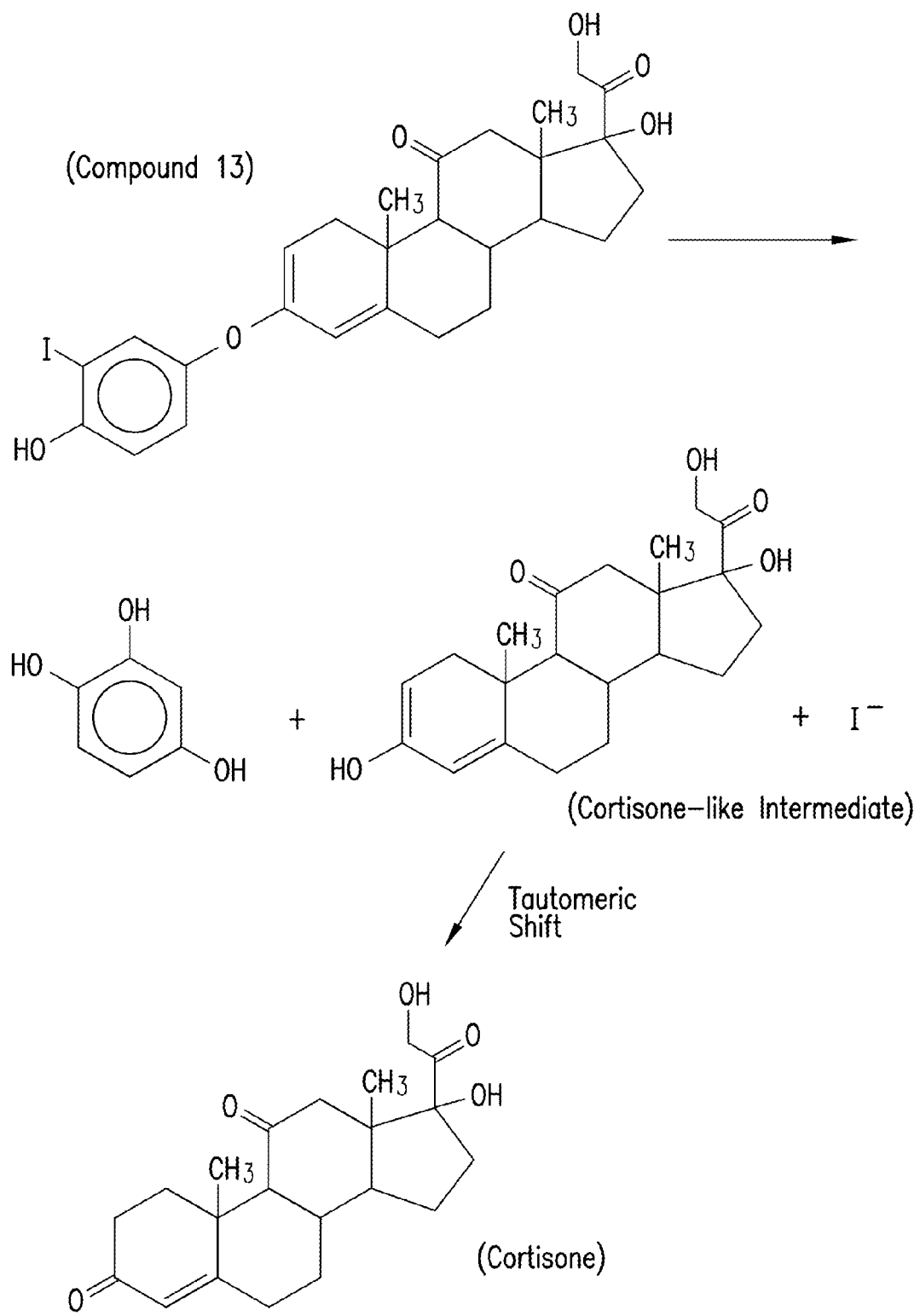
FIG. 13 is a diagram of a dehalogenation and cleavage reaction according to an embodiment of the present invention for the formation of cortisone.

FIG. 13 shows yet another example embodiment of the present invention for an iodo-phenol compound linked by an ether linkage to a molecule resembling cortisone, which forms part of the starting compound (Compound 13). This example is provided in part to demonstrate how molecules may be designed based on predictions about changes that may occur spontaneously or chemically in the arrangement of bonds and/or side groups of compounds that are ether linked to a halogenated phenol ring once such a compound is released as a result of the dehalogenation and cleavage reaction. This example shows how a compound, such as a drug compound, having a keto group and an adjacent double bond may be linked to a halogenated phenol ring by an ether linkage to take advantage of a tautomeric shift of a hydroxyl to form the keto group.

According to this example in FIG. 13, when Compound 13 comes in contact with an oxidizing agent or free radical, or is present in an oxidizing and/or free radical containing environment, the iodine (I) of the phenol ring is cleaved and replaced with a hydroxyl group. This free radical attack or oxidation of the phenol ring further results in the breaking or cleavage of the ether linkage (—O—) between the phenol ring and the cortisone-like molecule to release the cortisone-like intermediate molecule. In addition, an iodide ($I^-$), a benzenetriol-based compound (i.e., 1,2,4-benzenetriol) is formed. However, to achieve a lower energy state, this cortisone-like intermediate molecule may then spontaneously undergo a further conversion by tautomerization to become a cortisone molecule in the targeted tissue where the cortisone-like intermediate is formed.

Localized or targeted cortisone release may be useful in treating sites of inflammation, such as arthritis, multiple sclerosis (MS), ischemic bowel disease, or other diseases associated with high levels of free radical or oxidative species (FROS). Cortisone is a glucocorticoid with potent anti-inflammatory activity, but it also causes undesired systemic side effects in non-target tissues that are not inflamed Coupling of cortisone to the halogenated phenol ring via a linkage, such as an ether linkage, provides a bulky substitution that sterically blocks cortisone activity prior to release (and activation) by cleavage. Thus, the halogenated phenol-linked product allows targeted delivery of the product to the inflamed site. Oxidative dehalogenation, with concerted cleavage of the linkage (e.g., the ether linkage) produces a transient 3-hydroxy-cortisone at the site, which spontaneously converts or resonates to the 3-keto parent cortisone. As such, this mechanism provides concentrated delivery of cortisone to the inflamed site.

Figure 14:
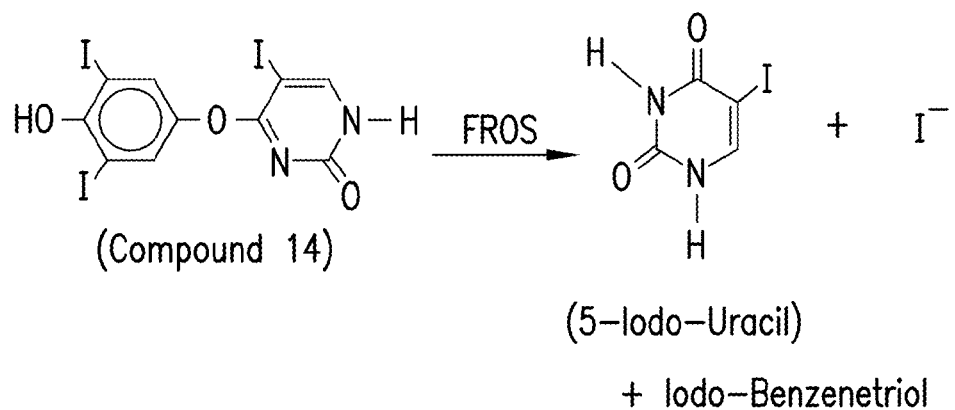
FIG. 14 is a diagram of a dehalogenation and cleavage reaction according to an embodiment of the present invention for the formation of 5-iodo-uracil.

Another example embodiment of a drug compound containing a keto group that is ether linked to a halogenated phenol ring to form a starting compound (Compound 14) of the present invention is shown in FIG. 14. The drug compound in this example is a 5-iodo-uracil that may be used for the treatment of cancer. When Compound 13 comes in contact with an oxidizing agent or free radical, or is present in an oxidizing and/or free radical containing environment, one of the iodines (I) of the phenol ring adjacent to the hydroxyl group is cleaved and is replaced with a hydroxyl group. This free radical attack or oxidation of the phenol ring further results in the breaking or cleavage of the ether linkage (—O—) between the phenol ring and the core structure of the drug compound, thus releasing an intermediate with a hydroxyl group in place of a keto group (not shown). In addition, an iodide ($I^-$), a benzenetriol-based compound (i.e., iodo-benzenetriol) is formed. However, to achieve a lower energy state, this intermediate may then spontaneously undergo keto-enol transition or tautomerization to become the 5-iodo-uracil molecule in the targeted tissue where formed.

As with other chemotherapeutic drugs linked to a halogenated phenol ring, Compound 14 may be delivered selectively to a targeted, high-FROS tissue (e.g., a cancerous tissue or tumor), which may help to reduce side effects on normal tissue. Compound 14 consists of 5-iodo-uracil (5-IU) ether linked to the halogenated phenol ring at the site of one of its keto groups. A similar compound, 5-fluoro-uracil (5-FU), is currently used as a chemotherapy agent. Indeed, 5-FU may also be a drug compound linked to a halogenated phenol ring as part of starting compound of the present invention. However, 5-iodo-uracil is less stable than 5-FU and can form 5-hydroxy-uracil at some rate through spontaneous deiodination. The 5-hydroxy-uracil product is cytotoxic and not preferred due to its side effects on normal tissue. However, according to embodiments of the present invention, masking by the linked halogenated phenol ring results in delivery and release at the targeted site. Thus, Compound 14 may be used to form 5-IU despite the cytotoxicity of its downstream 5-hydroxy-uracil product due to its selective formation in the targeted tissue. In fact, the greater potency of the 5-hydroxy-uracil product in conjunction with its targeted delivery may prove more efficacious at treating these sites. This example highlights another possible advantage of the present invention. Drug compounds that may have been previously considered to be too cytotoxic and/or produce too many unwanted side effects may be used according to the present invention due to their masking by the halogenated phenol ring and their targeted delivery to desired sites of treatment. Another advantage discussed elsewhere herein is that the increased hydrophobicity of these starting compounds will aid their ability to cross the blood-brain barrier (BBB) for target sites in the CNS.

As described above, the linkage between the halogenated phenol ring of a starting compound and the linked (drug) compound may include other types of linkages apart from an ether linkage (for a hydroxyl or keto group on the liberated compound) or a thioether linkage (for a sulfhydryl group on the liberated compound). In addition, the breakable or cleavable linkage between the halogenated phenol compound and the linked (drug) compound may also include a nitrogen linkage (see, e.g., FIG. 15), carbonyl linkage (see, e.g., FIG. 17) or a C—C bond (see, e.g., FIG. 20). The following provides general formulas and examples for starting compounds having these alternative linkages.

Figure 15:
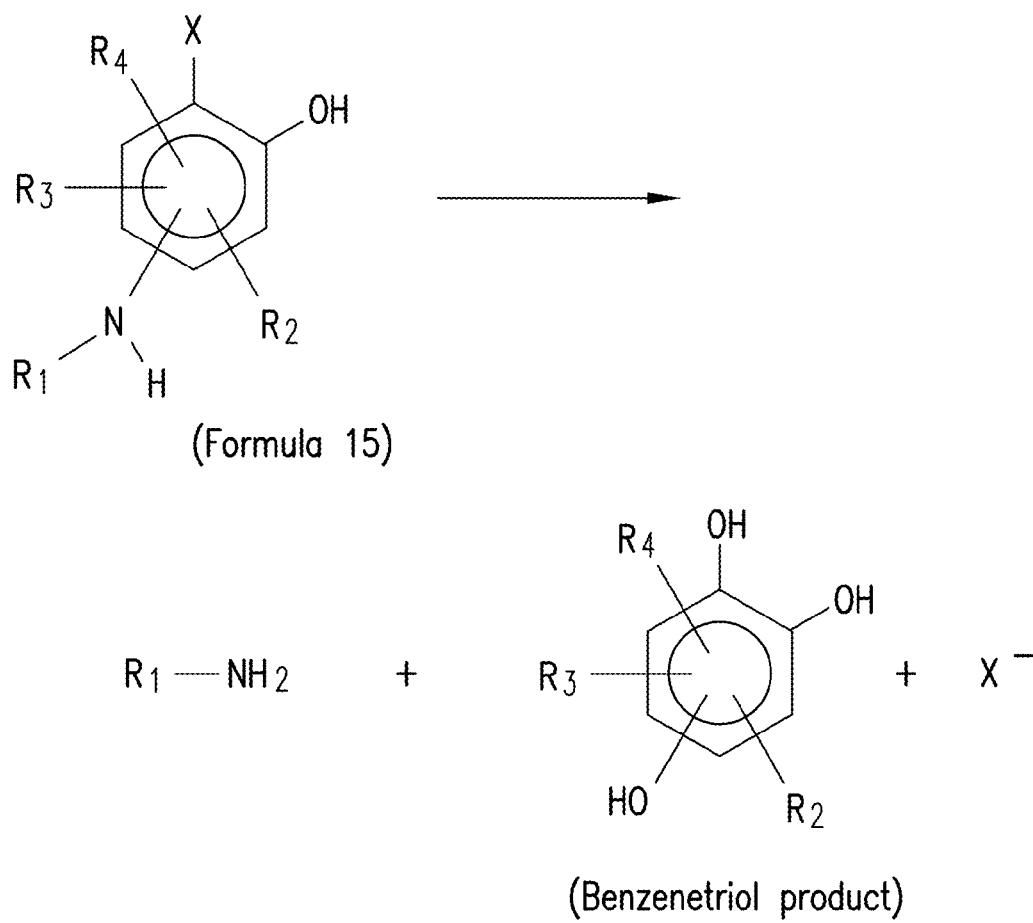
FIG. 15 is a diagram of a dehalogenation and cleavage reaction according to formula embodiments of the present invention with a nitrogen linkage.

FIG. 15 provides a general class of compounds (Formula 15) according to embodiments of the present invention. According to these embodiments, a compound having an amino group ($R_1$—$NH_2$), such as a drug compound, may be bonded or linked by a nitrogen linkage to a halogenated phenol ring to form part of a starting compound of the present invention. The nitrogen of the nitrogen linkage (—NH—) links the rest of the compound ($R_1$) to the halogenated phenol ring. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl). According to these embodiments, the nitrogen linkage (—Y—) may potentially be positioned anywhere relative to the halogen X and the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. Furthermore, combinations of these other substituents, $R_2$, $R_3$, and $R_4$, present on the phenol ring may themselves form fused rings with the halogenated phenol ring.

According to these embodiments in FIG. 15, when a compound of Formula 15 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the nitrogen linkage (—NH—) between the drug compound and the phenol ring to release the drug compound ($R_1$—$NH_2$) by bonding a hydrogen to form the amino group, and the nitrogen linkage on the phenol ring is replaced by a hydroxyl group. In addition to release of a halide ($X^-$) and the drug compound, a benzenetriol-based compound (e.g., 1,2,4-benzenetriol or 1,2,3-benzenetriol) may be formed. However, the exact formula name for this product of the reaction will depend on the identity of additional substituents, $R_2$, $R_3$, and $R_4$.

Figure 16:
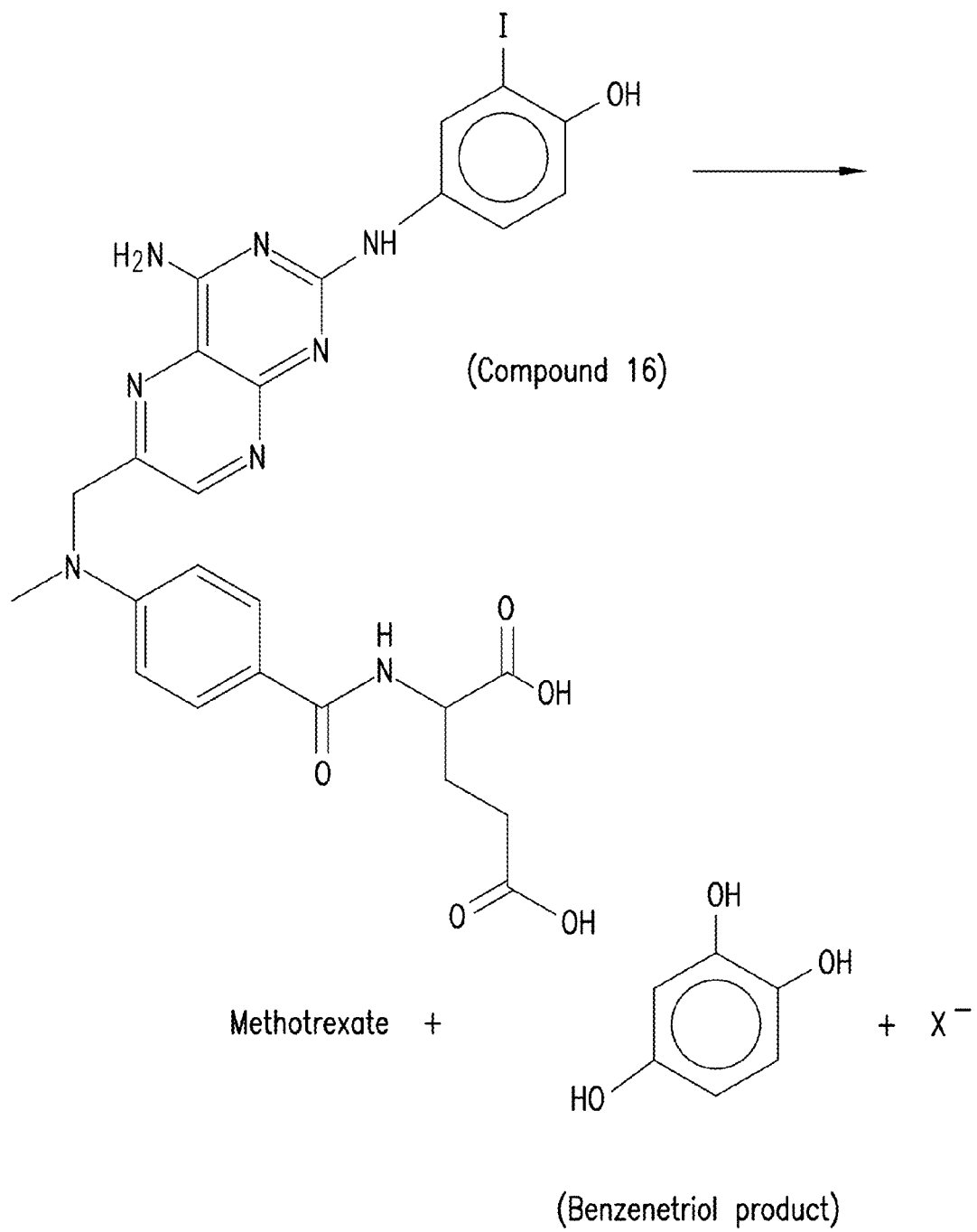
FIG. 16 is a diagram of a dehalogenation and cleavage reaction according to an embodiment of the present invention for the formation of methotrexate.

According to an embodiment of the present invention, FIG. 16 shows an example of a starting compound (Compound 16) containing a chemotherapeutic agent or drug, methotrexate, nitrogen linked to the halogenated phenol ring, which may be used to treat cancer. According to this example, when Compound 16 comes in contact with an oxidizing agent or free radical, or is present within an oxidizing and/or free radical containing environment, the iodine (I) is cleaved and removed from the phenol ring and replaced with a hydroxyl group. This free radical attack or oxidation of the phenol ring further results in the breaking or cleavage of the nitrogen linkage to liberate or form the methotrexate in addition to a benzenetriol compound (e.g., 1,2,4-benzenetriol) due to a hydroxyl group replacing the nitrogen linkage on the phenol ring, and a halide. Thus, targeted delivery of the methotrexate chemotherapy may be achieved at a cancerous or tumor site in the body having high FROS.

Figure 17:
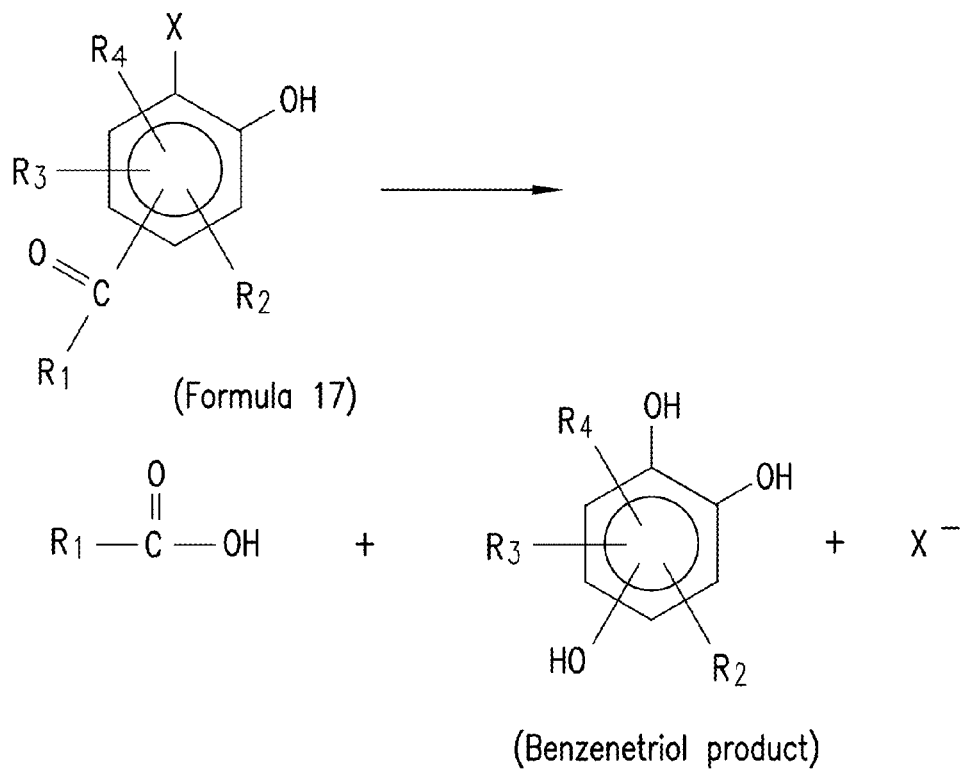
FIG. 17 is a diagram of a dehalogenation and cleavage reaction according to formula embodiments of the present invention with a carbonyl linkage.

FIG. 17 provides a general class of compounds (Formula 17) according to embodiments of the present invention. According to these embodiments, a compound having a carboxylic acid group ($R_1$—COOH), such as a drug compound, may be bonded or linked by a carbonyl linkage to a halogenated phenol ring to form part of a starting compound of the present invention. The carbon of the carbonyl linkage (—[C=O]—) links the rest of the compound ($R_1$) to the halogenated phenol ring. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl). According to these embodiments, the carbonyl linkage (—[C=O]—) may potentially be positioned anywhere relative to the halogen X and the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. Furthermore, combinations of these other substituents, $R_2$, $R_3$, and $R_4$, present on the phenol ring may themselves form fused rings with the halogenated phenol ring.

According to these embodiments in FIG. 17, when a compound of Formula 17 comes in contact with an oxidizing agent or free radical or is present in an oxidizing and/or free radical containing environment, the halogen X is cleaved and removed from the phenol ring and replaced with a hydroxyl group. This free radical attack or oxidation of the phenol ring further results in the breaking or cleavage of the carbonyl linkage (—[C=O]—) between the (drug) compound and the phenol ring to release the (drug) compound ($R_1$—COOH) by bonding of a hydroxyl to the carbonyl group, and the carbonyl linkage on the phenol ring is replaced by a hydroxyl group. In addition to release of a halide ($X^-$) and the (drug) compound, a benzenetriol-based compound (e.g., 1,2,4-benzenetriol or 1,2,3-benzenetriol) may be formed. However, the exact formula name for this product of the reaction will depend on the identity of additional substituents, $R_2$, $R_3$, and $R_4$.

Figure 18:
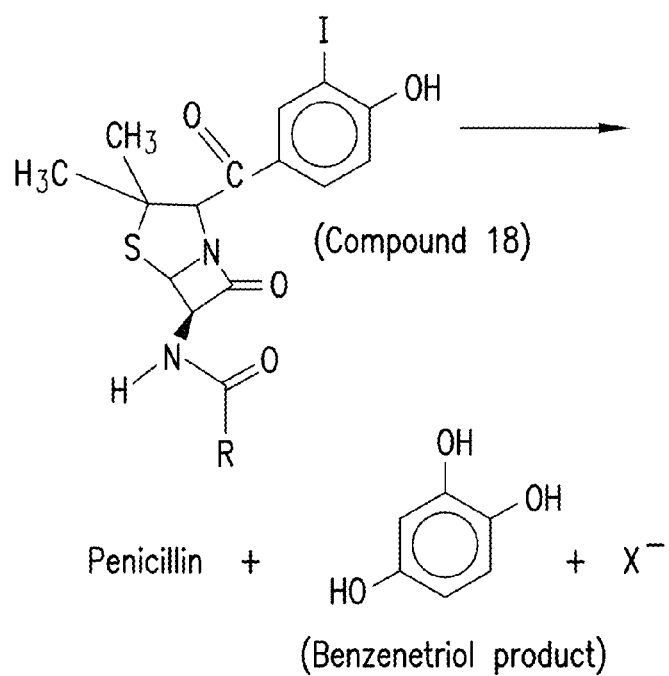
FIG. 18 is a diagram of a dehalogenation and cleavage reaction according to an embodiment of the present invention for the formation of penicillin.

According to an embodiment of the present invention, FIG. 18 shows an example of a starting compound (Compound 18) containing an antibiotic, penicillin or its derivatives, carbonyl linked to the halogenated phenol ring, which may be used to treat infection. The R group may vary according to the type or derivative of penicillin used. For example, "penicillin" may include penicillin G, penicillin V, ampicillin, amoxicillin, etc. For penicillin G, the R group is a benzyl, whereas the R group is a phenoxymethyl for penicillin V. According to this example, when Compound 18 comes in contact with an oxidizing agent or free radical, or is present within an oxidizing and/or free radical containing environment, the iodine (I) is cleaved and removed from the phenol ring and replaced with a hydroxyl group. This free radical attack or oxidation of the phenol ring further results in the breaking or cleavage of the carbonyl linkage to liberate or form the penicillin molecule in addition to a benzenetriol compound (e.g., 1,2,4-benzenetriol) due to a hydroxyl group replacing the nitrogen linkage on the phenol ring, and a halide. Thus, targeted delivery of the penicillin may be achieved to sites of infection in the body having high FROS.

Figure 19A:
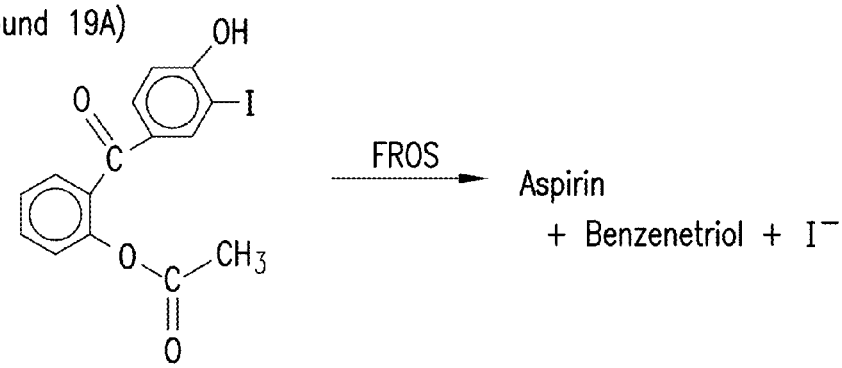
FIG. 19A is a diagram of a dehalogenation and cleavage reaction according to an embodiment of the present invention for the formation of aspirin.
Figure 19B:
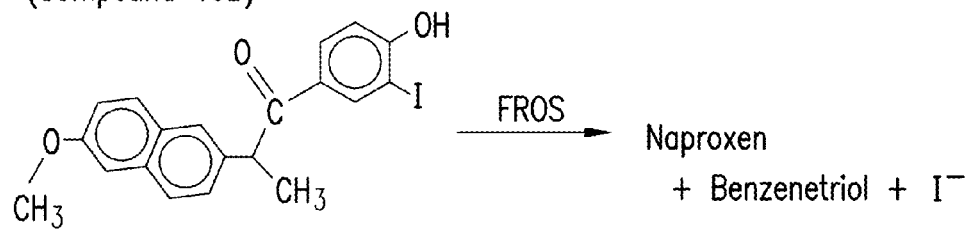
FIG. 19B is a diagram of a dehalogenation and cleavage reaction according to an embodiment of the present invention for the formation of naproxen.
Figure 19C:
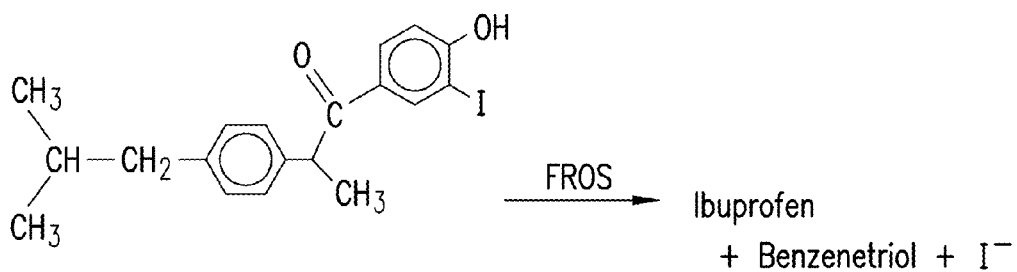
FIG. 19C is a diagram of a dehalogenation and cleavage reaction according to an embodiment of the present invention for the formation of ibuprofen.

FIG. 19 provides some additional examples of starting compounds containing drugs carbonyl linked to a halogenated phenol ring. FIG. 19A shows an example of a starting compound with aspirin carbonyl linked to a halogenated phenol ring. Upon cleavage in the presence of FROS, aspirin is formed along with a benzenetriol compound and a halide. FIG. 19B shows an example of a starting compound with naproxen carbonyl linked to a halogenated phenol ring. Upon cleavage in the presence of FROS, naproxen is formed along with a benzenetriol compound and a halide. Finally, FIG. 19C shows an example of a starting compound with ibuprofen carbonyl linked to a halogenated phenol ring. Upon cleavage in the presence of FROS, ibuprofen is formed along with a benzenetriol compound and a halide. Each of these example compounds of the present invention may be taken or administered to achieve targeted delivery of the drug to sites of inflammation and/or pain for relief of these symptoms.

Figure 20:
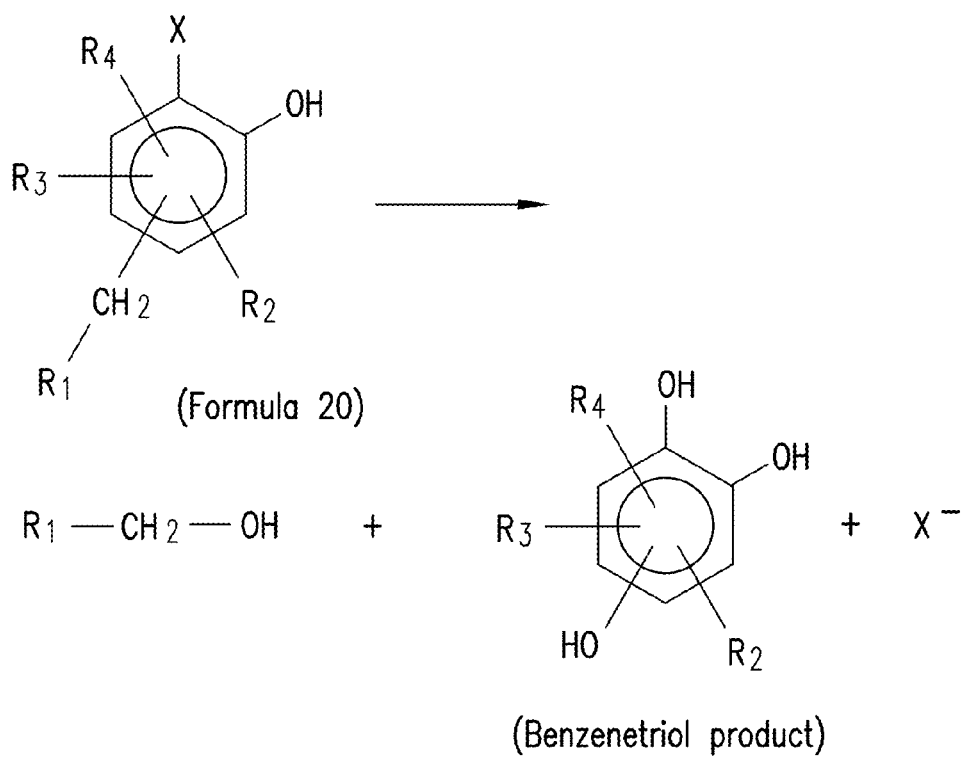
FIG. 20 is a diagram of a dehalogenation and cleavage reaction according to formula embodiments of the present invention with a C—C bond.

FIG. 20 provides a general class of compounds (Formula 20) according to embodiments of the present invention. According to these embodiments, a compound having an alcohol group ($R_1$—$CH_2$—OH), such as a drug compound, may be bonded or linked by a C—C bond to a halogenated phenol ring to form part of a starting compound of the present invention. The C—C bond links the rest of the compound ($R_1$) to the halogenated phenol ring. X is a halogen in the ortho position relative to the hydroxyl group (—OH) on the phenol ring (i.e., X is a halogen that is bonded to a carbon that is adjacent to a carbon bonded to the hydroxyl group (—OH) on the phenol ring). The halogen X may be selected from either iodine (I) or bromine (Br), but generally may not include fluorine (F) or chlorine (Cl). According to these embodiments, the C—C bond may potentially be positioned anywhere relative to the halogen X and the hydroxyl group (—OH) on the phenol ring. The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. Furthermore, combinations of these other substituents, $R_2$, $R_3$, and $R_4$, present on the phenol ring may themselves form fused rings with the halogenated phenol ring.

As noted above and further below, a C—C bond or linkage between a halogenated phenol ring and the rest of the compound ($R_1$) in some circumstances may not generally be cleaved during or following the dehalogenation reaction. Indeed, the starting compound (MIT) in FIG. 27 below is found to generally not be cleaved with the dehalogenation reaction. However, other starting compounds may be cleaved to form the alcohol in conjunction with the reaction. The full set of reasons for why cleavage does result in some circumstances (i.e., for some starting compounds), but not for others, are not entirely clear. However, it is believed that as a general rule $R_1$ groups (according to FIG. 20) comprising an aromatic ring near the C—C bond or linkage may generally be cleaved during or following a dehalogenation reaction, whereas those $R_1$ groups lacking an aromatic ring near the C—C bond may resist cleavage, which may reflect the different electronic states near the bond. Given the (surprising) discovery described herein that cleavage generally occurs with the various types of bonds or linkages, it is further surprising that cleavage would not then generally occur for compounds linked by the C—C bond given the bond energies. Further work would be needed to elucidate the mechanisms underlying the cleavage reaction and why some compounds may undergo cleavage while others do not.

According to these embodiments in FIG. 20, when a compound of Formula 20 comes in contact with an oxidizing agent or free radical or is present in an oxidizing and/or free radical containing environment, the halogen X is cleaved and removed from the phenol ring and replaced with a hydroxyl group. Depending on the compound, this free radical attack or oxidation of the phenol ring may potentially further result in the breaking or cleavage of the C—C bond between the (drug) compound and the phenol ring to release the (drug) compound ($R_1$—$CH_2$—OH) by bonding of a hydroxyl to the carbon, and the C—C bond on the phenol ring is replaced by a hydroxyl group. In addition to release of a halide ($X^-$) and the (drug) compound, a benzenetriol-based compound (e.g., 1,2,4-benzenetriol or 1,2,3-benzenetriol) may be formed. However, the exact formula name for this product of the reaction will depend on the identity of additional substituents, $R_2$, $R_3$, and $R_4$.

According to other embodiments, an organometallic starting compound of the present invention may comprise a halogenated phenol ring directly bonded to a metal or metalloid atom or element, which may be part of an R-group (i.e., via a "metal linkage"). For example, the metal atom or element may be a toxic element, such as mercury (Hg), which is bound to the halogenated phenol ring by the metal linkage, and the metal atom or element may be part of a larger R-group. When such a compound comes in contact with a FROS-containing environment, the metal linkage may become cleaved as a result of the dehalogenation reaction to relieve the toxic metal, such as mercury, at the site. In the case of mercury, the Hg atom bonded to the halogenated phenol ring may retain a charge and thus be formulated as a salt with a counter anion, such as chloride. Such a composition may be used to deliver and release the cytotoxic metal to a site of a cancerous tissue or tumor.

As described above in connection with FIGS. 6 and 7, polymers of two or more halogenated phenol rings (with or without empty or "spacer" units) may be utilized for delivering multiple drugs of the same or different type to sites of high FROS in the body, which may be associated with inflammation or disease. By way of example, these figures and their associated text focus on the use of an ether linkage between each of the units. However, as described above and in connection with immediately preceding FIGS. 15-20, such polymers of two or more halogenated phenol rings in FIGS. 6 and 7 may instead be linked by one of the alternative types of linkages including thioether linkages, nitrogen linkages, carbonyl linkages, sulfinyl linkages or possibly C—C bonds. To visualize these structures, the ether linkages in formulas in FIGS. 6 and 7 may simply be replaced with the respective alternative linkage. Although the structure and other substituents may otherwise be the same, some of the products of the reaction may be slightly different due to a different substituent being produced by the alternative linkage. For example, instead of the remaining chain having a hydroxyl group in place of the cleaved ether linkage, an amino group may be left in place of the cleaved nitrogen linkage, or a carboxyl group may be left in place of the cleaved carbonyl linkage, etc. It also envisioned that combinations of different types of linkages could be used between different neighboring units of a chain or polymer.

One of the main challenges in treating central nervous system (CNS) diseases is taking or administering pharmaceutical drug compounds that are able to cross the formidable blood-brain barrier (BBB) to exert their therapeutic effect in cells and tissues of the CNS. Large macromolecules and hydrophilic small molecules generally have difficulty crossing the BBB and thus insufficient availability in the brain without active transport. However, hydrophobic or lipophilic small molecules may be able to diffuse more readily across the membranes of the BBB and enter the brain. One key advantage of embodiments of the present invention is that the presence of a halogen(s), especially iodine (I), on the phenol ring of compounds of the present invention increases their hydrophobicity and improves the ability of these compounds to diffuse across the BBB and exert their effects in the brain. This is especially important for drugs intended for use in treating CNS diseases.

Improving the ability of CNS drugs to cross the BBB may have enormous benefits in treating CNS disease. For example, L-DOPA is the gold standard for treating Parkinson's disease, but the L-DOPA compound is slow to cross the BBB and causes unwanted side effects in peripheral tissues outside of the brain. According to an embodiment of the present invention, for example, a 3-hydroxy-3'-iodo-thyronamine compound (Compound 8) shown in FIG. 8A (or a 3-hydroxy-3'-iodo-thyronine compound in FIG. 8B) may diffuse across the BBB more easily largely due to the presence of the iodine on the phenol ring. Once Compound 8 crosses the BBB, it may exert its effects in a targeted region of the brain as a result of being converted to dopamine by the dehalogenation and cleavage reaction in the presence of free radicals and/or oxidative agents (i.e., FROS) present in affected brain tissue of individuals suffering from Parkinson's disease. Similarly, the 3-hydroxy-3'-iodo-thyronine compound in FIG. 8B may also cross the BBB and form L-DOPA in the presence of FROS, which may then be converted into dopamine. According to another embodiment described below in connection with FIG. 27 for example, a monoiodotyrosine (MIT) compound may diffuse more easily across the BBB and become converted by a dehalogenation reaction without cleavage to yield L-DOPA in the brain, which may then be converted into dopamine (other non-cleavage examples are also provided below for the production of dopamine or L-DOPA in targeted regions of the brain). Therefore, compounds of the present invention intended to treat CNS diseases may be taken or administered at lower doses since a greater proportion of these compounds in the bloodstream will cross the BBB and exert targeted effects in the brain.

Another key advantage of embodiments of the present invention is that by linking a drug compound to a halogenated phenol ring, the normal biological activity or effect of the drug compound may be masked (i.e., sterically blocked or hindered) until its release at the target site of inflammation or disease. For example, the halogenated phenol linked drug(s) may not be able to bind to, interact with, modify, etc., their molecular or cellular targets in cells or tissues until the drug compound is liberated as described herein. The presence of a halogenated phenol ring linked to the drug compound may also sterically hinder the ability of drug metabolizing enzymes to bind and modify the drug compound until its release at the target site. The covalently attached halogenated phenol ring may further serve to help shield or protect the drug from other non-specific chemical or enzymatic degradation until its release at the target site, thus potentially reducing side effects, and/or provide a more sustained release of the drug. In addition, shielding of the drug by the halogenated phenol ring may also help to block unintended or abusive use of the drug by other routes of administration (e.g., inhalation). It may also be true that by achieving targeted delivery, lower dosages may be required for a given therapeutic effect.

Figure 27:
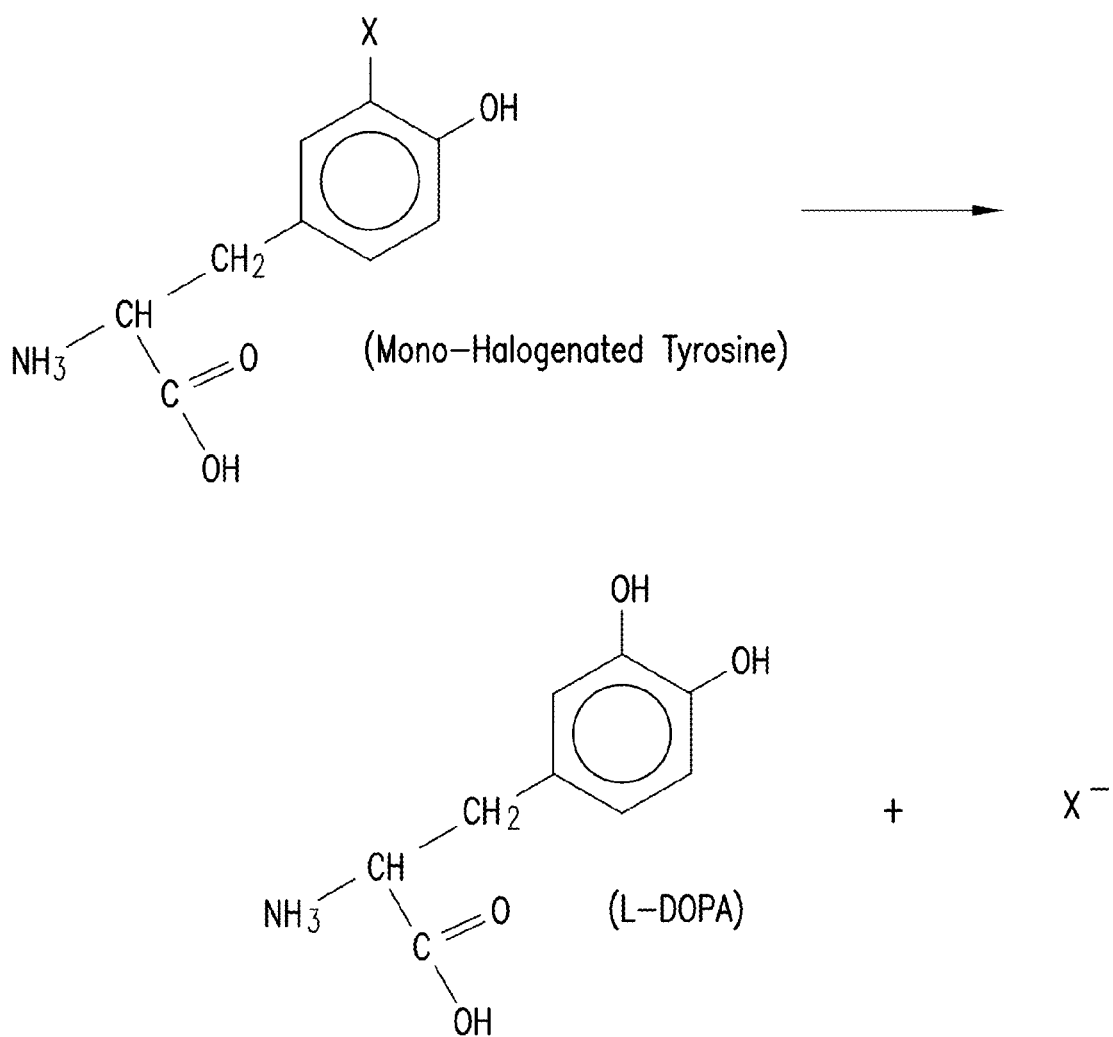
FIG. 27 is a diagram of a dehalogenation reaction without cleavage according to a compound embodiment of the present invention.

Thus, the halogenated phenol ring provides a "pro-drug" format for the protection and masking of the conjugated drug compound until its release at the target site. Upon removal of the blocking phenol ring, the compound or drug may be freed to bind a target or receptor or to exert its activity. For example, L-DOPA is used to effectively treat Parkinson's disease. However, L-DOPA causes many unwanted side effects as a result of its conversion to dopamine by DOPA decarboxylase in peripheral tissues outside of the brain. Currently, L-DOPA is administered in combination with another drug (e.g., Carbidopa) which does not cross the BBB to suppress these undesired effects by blocking the conversion of L-DOPA to dopamine in these other tissues. One key advantage of dopamine or L-DOPA releasing or producing compounds of the present invention, such as the halogenated phenol compound linked to dopamine or L-DOPA, such as in FIG. 8, reverse T3 in FIG. 22, monoiodo-phenylalanine or the monoiodo-tyrosine compound in FIG. 27, are each not recognized by the DOPA-decarboxylase enzyme. Accordingly, the dopamine or L-DOPA releasing or producing compounds of the present invention may be taken or administered alone (i.e., without or with only minimal or small doses of Carbidopa) because their conversion to bioactive dopamine might be limited to desired sites of inflammation and disease in the CNS, which may be deficient in levels of dopamine.

In addition to providing the targeted delivery of a drug compound, compounds of the present invention have the further advantage of providing an anti-oxidant and/or free radical scavenging benefit. Following administration or taking of a halogenated phenol compound according to embodiments of the present invention to an individual, the starting compound undergoes dehalogenation and cleavage of the relevant linkage in the presence of free radicals or oxidative agents. During this dehalogenation and cleavage reaction, which may result in the release of a drug compound, free radicals or oxidative agents that trigger the reaction are consumed. Thus, the amounts of FROS at the site may be reduced or depleted by the reaction. In addition, one of the products of the dehalogenation and cleavage reaction is likely to be a benzenetriol- or benzenetetrol-based compound, which also has strong anti-oxidant and/or free radical scavenging properties to consume more free radicals or oxidative agents in subsequent or additional reaction step(s). Generally speaking, increasing the number of hydroxyl groups on the benzene-containing product of the reaction may also make the compound more reductive and thus a more potent anti-oxidant and/or free radical scavenger.

According to some embodiments, if the compound of the present invention comprises two or more halogenated phenol rings linked together by an ether linkage(s) or group(s), then the anti-oxidant and/or free radical scavenging benefit may be multiplied further by consuming an even greater number of free radicals or oxidative agents in multiple dehalogenation reaction(s). Therefore, one of the key benefits and advantages of compounds of the present invention, in addition to targeted delivery of a drug compound, is that free radicals and/or oxidative agents may be consumed at or during multiple reaction steps (i.e., during the dehalogenation reaction and by virtue of the one or more anti-oxidant and/or free radical scavenging products of the reaction).

The combination of targeted drug delivery to sites of disease and/or inflammation, increased stability, sustained release, antioxidant and/or free radical scavenging properties and/or masked bioactivity in non-targeted tissues with halogenated phenol compounds of the present invention may provide enormous benefit and efficacy for improved treatment of disease over existing therapies. In addition, compounds of the present invention intended for the treatment of CNS diseases may have the further benefit of having increased hydrophobicity due to the presence of halogens and phenol ring(s), which may greatly improve the ability of these drug compounds to cross the blood-brain barrier.

According to another broad aspect of the invention, a compound according to some embodiments may provide anti-oxidant and/or free radical scavenging benefits without the targeted delivery of a drug compound per se (i.e., without the targeted delivery and release of a drug compound that is linked to the halogenated phenol ring), although any antioxidant and/or free radical scavenging compound products of the reaction may themselves be thought of as a "drug compound." In other words, the dehalogenation and cleavage reaction may be used primarily to consume the oxidizing agents and/or free radicals (i.e., FROS). In addition, as mentioned above, products of this reaction, such as quinones, etc., may themselves further function as free radical and/or oxidative scavengers. Although the compounds according to these embodiments are used primarily as anti-oxidant, anti-inflammatory and/or EROS scavenging agents, it cannot be ruled out that some products of the dehalogenation and cleavage reaction from these compounds may have other bioactivities (i.e., not related to anti-oxidant, anti-inflammatory and/or FROS scavenging functions). However, it may be preferred that according to these embodiments, any other (non-related) bioactivities of such products be minimal or non-existent.

Compounds according to these embodiments having anti-oxidant and/or free radical scavenging effects (i.e., FROS scavengers) may be taken by, or administered, provided or given to, an individual to avoid cellular or tissue damage or aging caused by oxidizing agents and/or free radicals or to lessen the pathological consequences and/or symptoms of disease, inflammation or normal aging which are mediated by oxidizing agents and/or free radicals. These anti-oxidant and/or free radical scavenging effects may be site-specific or systemic depending on the route of administration and/or the nature of the condition being treated. For example, such compounds having anti-oxidant and/or free radical scavenging effects may be used to treat particular inflammation-mediated diseases, such as autoimmune disease, arthritis, atherosclerosis, ischemic bowel disease, multiple sclerosis (MS), retrolental fibroplasia (RLF), and cardiovascular disease, as well as secondary free radical-mediated conditions associated with various diseases, such as cachexia or sepsis, and to protect the skin from damage that might otherwise result from solar or radiation exposure. In addition, compounds of the present invention may be used to offset FROS exposure and tissue damage during ischemic and/or reperfusion conditions, such as ischemia and/or reperfusion associated with myocardial infarction.

Figure 21:
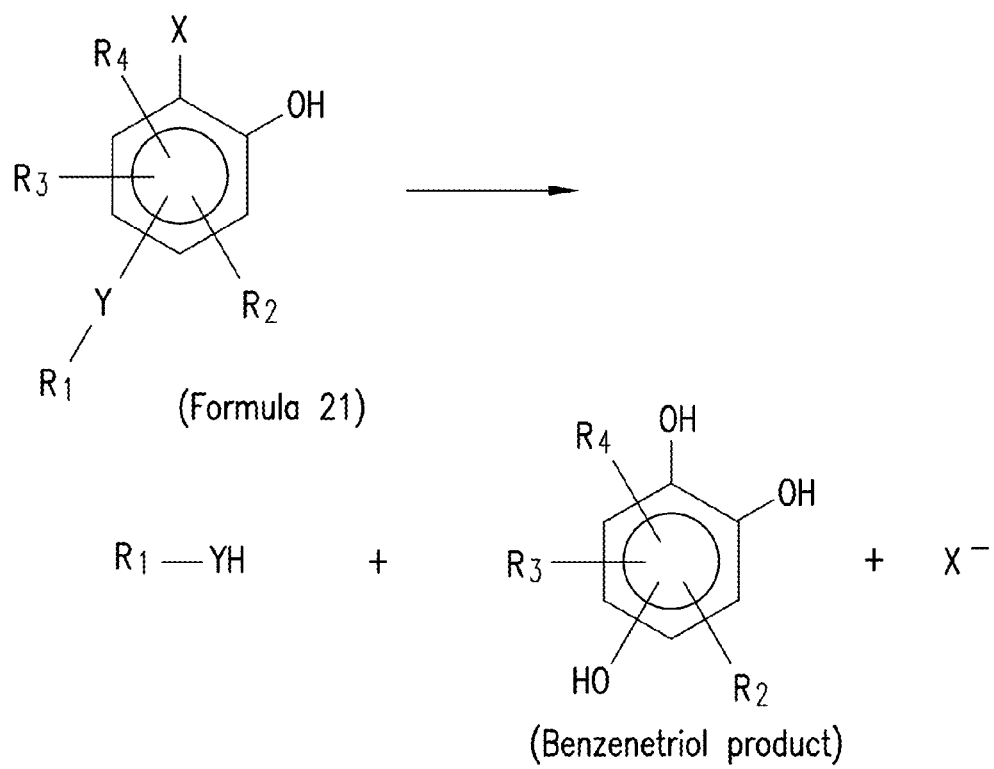
FIG. 21 is a diagram of a dehalogenation and cleavage reaction according to formula embodiments of the present invention for use as an antioxidant and/or free radical scavenger.

FIG. 21 provides a general class of compounds (Formula 21) according to embodiments of the present invention which may be used as an anti-oxidant, free radical scavenger, and/or anti-inflammatory agent. According to these embodiments, a substituent ($R_1$) may be bonded by an ether or thioether linkage to a halogenated phenol ring to faun part of the compound of the present invention. The ether or thioether linkage (—Y—) may be (i) an ether linkage if Y is an oxygen atom and the —YH group on the $R_1$—YH product of the cleavage reaction is a hydroxyl group or (ii) a thioether linkage if Y is a sulfur atom and the —YH group on the $R_1$—YH product of the cleavage reaction is a sulfhydryl group. X is a halogen in the ortho position relative to a hydroxyl group (—OH) on the phenol ring (i.e., X is a halogen that is bonded to a carbon that is adjacent to a carbon bonded to a hydroxyl group (—OH) on the phenol ring). The halogen X may be selected from either iodine (I) or bromine (Br), but generally may not include fluorine (F) or chlorine (Cl). The difference between embodiments shown in FIG. 21 and those shown in FIGS. 1-20 above is that the compound $R_1$—YH released by the reaction in FIG. 21 is not necessarily a drug compound per se and may include a broader group of compounds and chemical groups, some of which may function as FROS scavengers as well. According to these embodiments, $R_1$ may include, for example, a hydrogen, an alkyl, an aryl, an amino, a nitro, etc., groups. According to some of these embodiments, a varied class of halogenated diphenyl or dihydroxy-diphenyl compounds are proposed (see FIG. 23 below).

According to these embodiments in FIG. 21, the ether or thioether linkage (—Y—) may be positioned anywhere on the phenol ring not occupied by the ortho-positioned hydroxyl group and halogen X (i.e., on any of the remaining carbons of the phenol ring). Similarly, additional substituents $R_2$, $R_3$, and $R_4$ may be positioned anywhere on the phenol ring not occupied by the ortho-positioned hydroxyl group and halogen X (i.e., on any of the remaining carbons of the phenol ring). The identity of each of the other substituents, $R_2$, $R_3$, and $R_4$, present on the phenol ring may vary and may include, for example, a hydrogen, a hydroxyl, a sulfhydryl, an alkyl, a halogen, an amino, a nitro, etc., groups. Unlike halogen X adjacent to the hydroxyl group of the phenol ring, substituents $R_2$, $R_3$, and $R_4$ may be any halogen atom. According to some alternative embodiments, one, two or three of these variable substituents may be hydrogen. Furthermore, combinations of these other substituents, $R_2$, $R_3$, and $R_4$, present on the phenol ring may themselves form fused rings with the halogenated phenol ring.

According to some embodiments, the addition of a second halogen ortho to the hydroxyl group may influence the acidity of the hydroxyl groups due to the electron withdrawing character of the halogen. Thus, at physiological pH, the $O^-$ form may predominate over the —OH form of the substituent. This ionization of the substituent may prove useful in some circumstances for improved solubility and/or diffusion through cellular membranes and tissues.

According to embodiments of the present invention, when a compound of Formula 21 comes in contact with an oxidizing agent or free radical, or is present in an oxidizing and/or free radical containing environment, the halogen X is cleaved and removed from the phenol ring and replaced with a hydroxyl group. This free radical attack or oxidation of the phenol ring further results in the breaking or cleavage of the ether or thioether linkage (—Y—) to release a compound $R_1$—YH, and the ether or thioether linkage is replaced by a hydroxyl group on the phenol ring. In addition to release of a proton ($H^+$; not shown), a halide ($X^-$) and compound $R_1$—YH, a benzenetriol-based or hydroxyhydroquinone-based compound (e.g., 1,2,4-benzenetriol) may be formed. However, the exact formula name for this product of the reaction will depend on the identity of the additional substituents, $R_2$, $R_3$, and $R_4$. In addition to an oxidizing agent or free radical being consumed in the dehalogenation and cleavage reaction, the benzenetriol-based product of the reaction may also function as an anti-oxidant and/or free radical scavenger in a subsequent reaction. Depending on the exact identity of the $R_1$ substituent, the product compound $R_1$—YH may also function as an anti-oxidant and/or free radical scavenger.

Alternatively, the type of linkage used for these FROS scavenging embodiments may vary and may instead include a nitrogen linkage, a carbonyl linkage, a sulfinyl linkage, or a C—C bond in place of the ether or thioether (Y) linkage. Such embodiments would function similarly in consuming FROS during a dehalogenation and cleavage reaction but would produce slightly different products with a different substituent at the site of the alternative linkage. The structures of these alternative embodiments may be deduced from the description herein, particularly in reference to FIGS. 15, 17 and 20.

Figure 22:
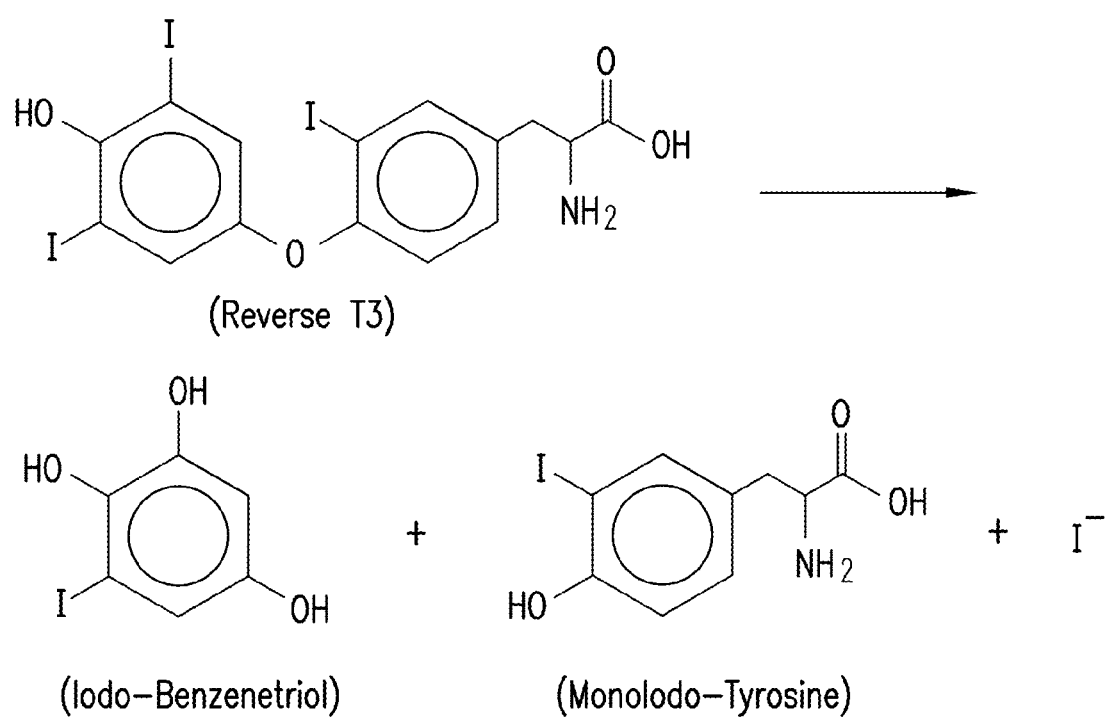
FIG. 22 is a diagram of a dehalogenation and cleavage reaction according to a compound embodiment of the present invention using reverse T3 as an antioxidant and/or free radical scavenger.

As shown in FIG. 22, reverse T3 or rT3 (i.e., 3,3',5'-triiodothyronine) could be used as an anti-oxidant, free radical scavenger, and/or anti-inflammatory agent. As shown in FIG. 22, when the reverse T3 compound comes in contact with an oxidizing agent or free radical, or is present in an oxidizing and/or free radical containing environment, the iodine (I) on the outer phenol ring of reverse T3 is cleaved and replaced with a hydroxyl group. This free radical attack or oxidation of the outer phenol ring of reverse T3 further results in the breaking or cleavage of the ether linkage to form an iodo-benzenetriol compound, a monoiodo-tyrosine compound (MIT), and a halide. In addition to an oxidizing agent or free radical being consumed in the dehalogenation and cleavage reaction, the iodo-benzenetriol and monoiodo-tyrosine products of the reaction may also function as an anti-oxidant and/or free radical scavenger in a subsequent reaction. However, the use of reverse T3 strictly as an anti-oxidant or free radical scavenger may be problematic due to the potential biological activity of a downstream product of the reaction (i.e., L-DOPA and/or dopamine from MIT—see discussion below in reference to FIG. 27).

According to other embodiments, an antioxidant compound of the present invention may comprise a halogenated phenol ring directly bonded to a metal or metalloid atom or element, which may be part of an R-group (i.e., via a "metal linkage"). For example, such a composition may comprise boron (B) bonded three ways to three R-groups, R, R', R", one or more of which may be a halogenated phenol ring. When such a compound comes in contact with a FROS-containing environment, the metal linkage between the boron atom and the one or more halogenated phenol rings may become cleaved as a result of the dehalogenation reaction to consume FROS. In addition to the benzentriol-based compounds formed, a boric acid or sodium borate molecule may also be generated by the reaction.

Figure 23A:
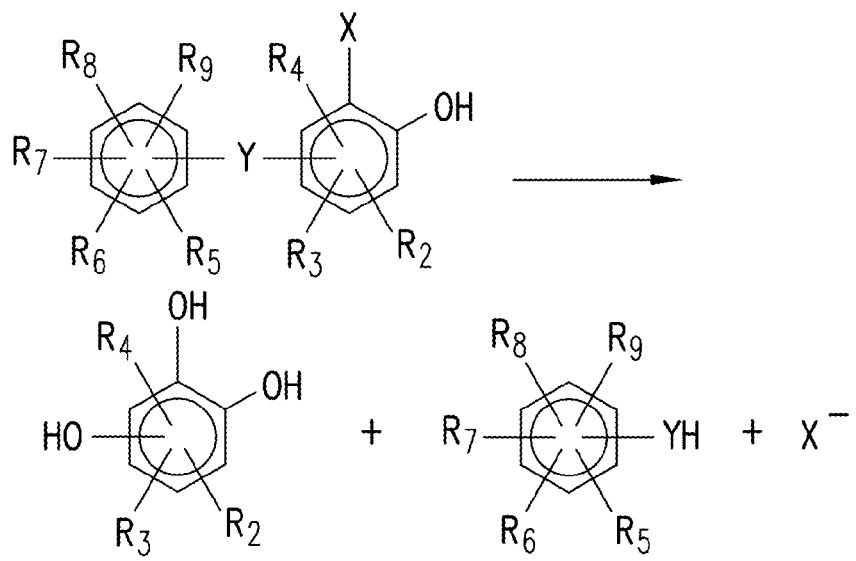
FIG. 23A is a diagram of a dehalogenation and cleavage reaction according to diphenyl formula embodiments of the present invention with an ether or thioether linkage.
Figures 23B, 23C:
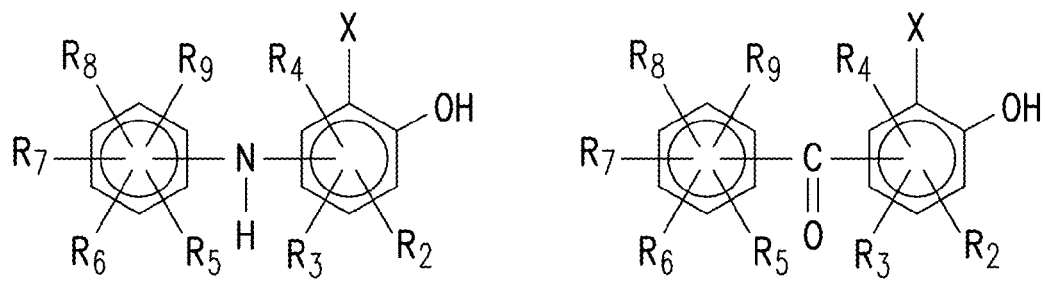
FIG. 23B is a diphenyl formula for embodiments of the present invention with a nitrogen linkage.
FIG. 23C is a diphenyl formula for embodiments of the present invention with a carbonyl linkage.

FIGS. 23A-D provide general classes of diphenyl compounds comprising a halogenated phenol ring linked to another benzene ring. X is a halogen and may be either iodine or bromine (but may preferably be iodine). The other substituents, $R_2$, $R_3$, $R_4$, $R_5$, $R_6$, $R_7$, $R_8$, and $R_9$, may vary and may include, for example, a hydrogen, a hydroxyl, a sulfhydryl, an alkyl, a halogen, an amino, a nitro, etc., groups. According to some alternative embodiments, one, two, three, four, five, six, seven or eight of these variable substituents may be hydrogen. FIG. 23A represents a general class of diphenyl ether or thioether compounds. Similarly to FIG. 21, the ether or thioether linkage (—Y—) in FIG. 23A may be an ether linkage if Y is an oxygen atom or a thioether linkage if Y is a sulfur atom. The cleavage reaction would form products similarly as shown in FIG. 21.

Figure 23D:
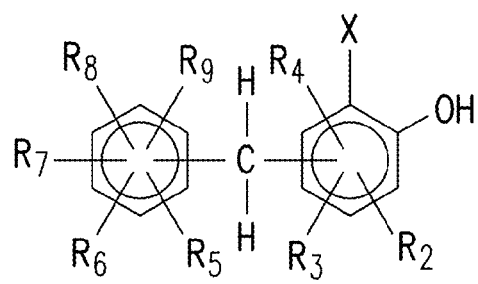
FIG. 23D is a diphenyl formula for embodiments of the present invention with a C—C bond.

As described above, the ether (or thioether) linkage of the starting compound formula in FIG. 23A may alternatively be replaced with, for example, a nitrogen linkage (FIG. 23B; a diphenylamine structure), a carbonyl linkage (FIG. 23C; i.e., a benzophenone), a sulfinyl linkage, or a C—C bond (FIG. 23D). Although the products of a cleavage reaction involving one of these alternative starting compounds may be different due to the different substituent formed at the site of the alternative linkage, these alternative starting compounds may be used similarly to consume FROS. As a few examples, these compounds may include 3-iodo-4,4'-dihydroxy-benzophenone (forming a 4-carboxy-phenol in FROS), 3-iodo-4-hydroxy-phenylsulfoxide (forming p-toluene sulfonic acid), 3-iodo-4-hydroxy-diphenyl amine (forming benzyl amine), or diiodo-hydroxy-diphenylmethane (forming benzyl alcohol).

FIGS. 23E-H provide more limited classes of dihydroxy-diphenyl compounds according to embodiments of the present invention which may be used as an anti-oxidant, free radical scavenger, and/or anti-inflammatory agent. These formulas correspond to those in FIGS. 23A-D, respectively, with one of the substituents on the ring being a hydroxyl group and at least two of the other substituents being a hydrogen. The substituents on the α-ring would include at least two hydrogens. For example, FIG. 23E (corresponding to FIG. 23A) provides a subset of compounds falling under the more general formulas of FIG. 21 wherein $R_1$ is an aryl group, and which may include a variety of dihydroxy-diphenyl ether compounds (DHDPEs). According to these embodiments, in contrast to FIGS. 23A-D, each of the variable substituents $R_2$, $R_3$, and $R_4$ may be either a hydrogen or a halogen. X is a halogen and may be either iodine or bromine (but may preferably be iodine). Likewise, if one or more substituents $R_2$, $R_3$, and $R_4$ are a halogen, they may be either iodine or bromine (but may preferably be iodine). Similarly to FIG. 21, the ether or thioether linkage (—Y—) in FIG. 23E may be an ether linkage if Y is an oxygen atom or a thioether linkage if Y is a sulfur atom. The cleavage reaction would form products similarly as shown in FIG. 21.

Figure 23E:
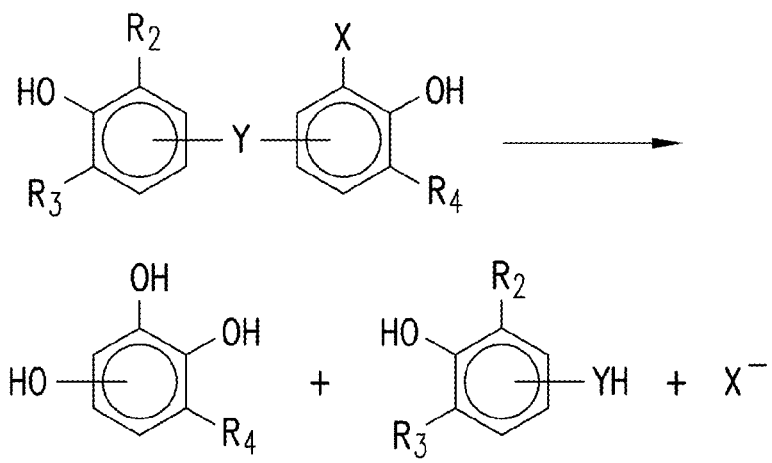
FIG. 23E is a diagram of a dehalogenation and cleavage reaction according to dihydroxy diphenyl formula embodiments of the present invention with an ether or thioether linkage.
Figure 23F:
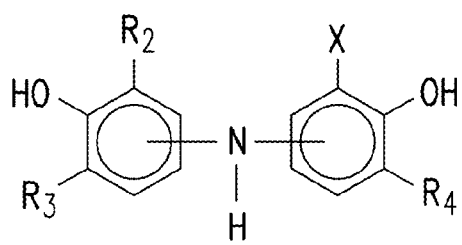
FIG. 23F is a dihydroxy diphenyl formula for embodiments of the present invention with a nitrogen linkage.
Figure 23G:
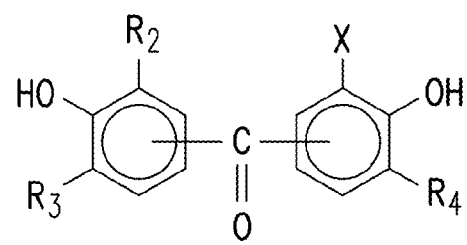
FIG. 23G is a dihydroxy diphenyl formula for embodiments of the present invention with a carbonyl linkage.
Figure 24:
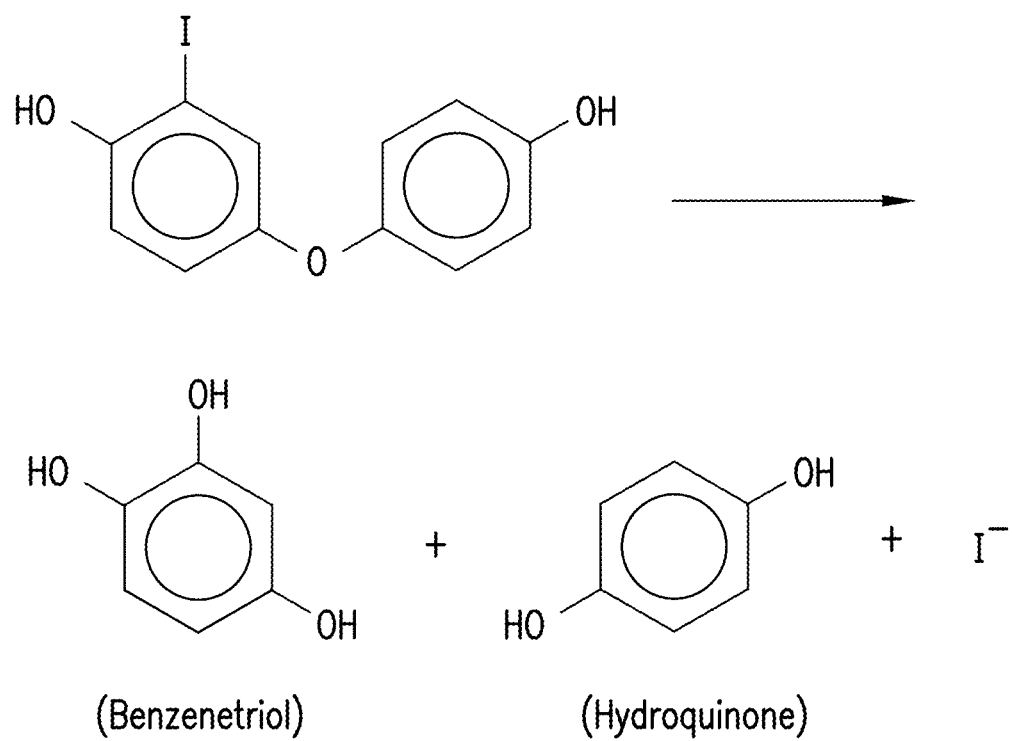
FIG. 24 is a diagram of a dehalogenation and cleavage reaction according to a compound embodiment of the present invention (3-iodo-4,4'-dihydroxy-diphenyl ether) for use as an antioxidant and/or free radical scavenger.

FIG. 24 shows a specific example embodiment of the present invention according to FIG. 23E of a 3-iodo-4,4'-dihydroxy-diphenyl ether compound that may be used as an anti-oxidant, free radical scavenger, and/or anti-inflammatory agent. Such a compound may be used to treat inflammation or diseases associated with inflammation, such as arthritis, etc., or to reduce free radical or oxidative load generally within the body. According to this example, when the 3-iodo-4,4'-dihydroxy-diphenyl ether compound comes in contact with an oxidizing agent or free radical, or is present in an oxidizing and/or free radical containing environment, the iodine (I) is cleaved and removed from the phenol ring and replaced with a hydroxyl group. This free radical attack or oxidation of the phenol ring further results in the breaking or cleavage of the ether linkage to form or produce a benzenetriol (or hydroxyhydroquinone) compound, a hydroquinone, and a halide. In addition to an oxidizing agent or free radical being consumed in the dehalogenation and cleavage reaction, both of the benzenetriol (or hydroxyhydroquinone) and hydroquinone products of the reaction may further function as an anti-oxidant and/or free radical scavenger in a subsequent reaction. According to a similar embodiment, a 3,3'-diiodo-4,4'-dihydroxy-diphenyl ether compound is proposed having two halogens on one of the phenol rings.

Figure 23H:
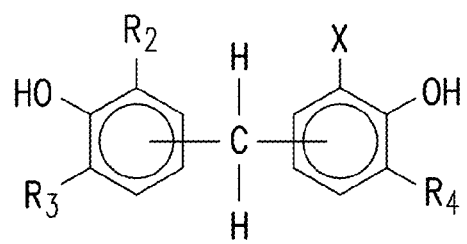
FIG. 23H is a dihydroxy diphenyl formula for embodiments of the present invention with a C—C bond.

As described above, the ether (or thioether) linkage of the starting compound formula in FIG. 23E may alternatively be replaced with a nitrogen linkage (FIG. 23F; a diphenylamine structure), a carbonyl linkage (FIG. 23G; i.e., a benzophenone), or a C—C bond (FIG. 23H). Although the products of a cleavage reaction involving one of these alternative starting compounds may be different due to the different substituent formed at the site of the alternative linkage, the reaction may be used similarly to consume FROS.

According to some of these embodiments, a pharmaceutical composition is provided comprising any compound(s) having a structural formula according to FIGS. 23A-H in combination with a pharmaceutically acceptable carrier.

According to other embodiments, one or more of these halogenated diphenyl or dihydroxy-diphenyl (DHDP) compounds shown in FIG. 23 are proposed for use as a sunscreen topically applied to the skin. Such dihydroxy-diphenyl compounds may include those having any of the alternative linkages shown between the two phenyl groups. For example, one or more halogenated dihydroxy-diphenyl ether (DHDPE) compounds according to FIG. 20A are proposed for use in a sunscreen composition. In addition, dihydroxy-diphenyl (DHDP) compound(s) similar to those in FIG. 23 but lacking the halogen substituent (X) (i.e., any of the formulas in FIG. 23 with a hydrogen replacing X and substituents $R_2$, $R_3$, and $R_4$ each being a hydrogen) are also proposed for this purpose. The phenol rings of these compounds are believed to be effective in directly absorbing UV light with some amount of a sun protection factor (SPF). Furthermore, according to the reactions described herein, halogenated diphenyl or dihydroxy-diphenyl compounds of FIG. 23 having one or more halogens (e.g., iodines) on the phenol rings may also be effective at scavenging FROS produced by sunlight exposure in the skin (e.g., in the extracellular spaces) via the dehalogenation and cleavage reaction, perhaps in addition to functioning as a direct sunlight absorber. Therefore, a variable number of halogens (i.e., between 0-4 halogens or iodines) may be placed on the phenol rings of these compounds as substituents.

Radiation from the sun can cause the formation of damaging oxidants and/or free radicals by interaction with molecules in the skin. Therefore, by topically applying any of the halogenated diphenyl or DHDP compound(s) of FIG. 23 (including any halogenated DHDPE compounds) to the skin, the FROS produced by the solar radiation may be consumed by the dehalogenation reaction prior to the cells and tissue of the skin becoming damaged thereby (possibly in addition to protecting the skin by direct absorption of UV light). Moreover, increasing the number of halogens (e.g., iodines) on the phenol rings is believed to further increase the amount of direct absorption or blocking of UV light by the phenol ring(s). In addition, these halogenated compounds (especially those with one or more iodines) can be "dissolved" into hydrophobic oils or lotions of a topically applied sunscreen composition due to their own hydrophobicity. As stated above, however, if there are no iodines or other halogens on the rings, then the compound will not function as FROS scavenger via the dehalogenation/cleavage reaction, but may still be effective as a direct UV absorber.

According to these embodiments, one or more such halogenated or non-halogenated (e.g., iodinated or non-iodinated) diphenyl or dihydroxy-diphenyl compound(s) of FIG. 23 may be combined with any suitable sunscreen vehicle(s), excipient(s) and/or carrier(s) for topical application to the skin (e.g., as a lotion, oil, salve, etc.) as described herein or known in the art. These sunscreen compositions may be spread, rubbed, or sprayed onto the skin. Any suitable ingredient(s) or vehicle(s), such as oils including olive oil, coconut oil, mineral oil, etc., emollients, shea butter, emulsifiers, etc., that are normally used as part of, or in formulating, tanning or sunscreen lotions, etc., may be used as part of the present sunscreen compositions in combination with any of these halogenated or non-halogenated compound(s) for topical application. Indeed, some of these additional ingredients, such as oils, may aid in wicking, pulling or absorbing the compounds deeper into the skin. The sunscreen composition may be a water-in-oil emulsion and may include an aqueous phase and an oil phase with or without an emulsifier. Sunscreen compositions that are spray applied to the skin may include a propellant as an additional vehicle or ingredient. As an example sunscreen formulation, any of the halogenated DHDPE compounds described herein may be formulated as a 0.1% suspension in coconut oil to provide a topical lotion, which may be applied topically to provide additional epidermal hydration and protect the skin from harmful solar UV radiation. For a description of suitable sunscreen vehicles or ingredients that may be used in combination with the proposed halogenated (and/or non-halogenated) dihydroxy-diphenyl compound(s) as part of a sunscreen composition of the present invention, see, e.g., U.S. Pat. Nos. 5,188,831; 5,250,289; 5,935,556; and 6,858,200, the entire contents and disclosures of which are incorporated herein by reference Embodiments of the present invention further include methods of topically applying, spreading, spraying, etc., a sunscreen composition of the present invention to the skin of an individual to provide sun protection.

According to some of these embodiments, DHDPE compounds that may be used in a sunscreen composition may include those having hydroxyl groups at the 4 and 4' positions. Examples of these 4,4'-hydroxy compound embodiments include those having iodines at one or more of the 3-, 5-, 3'- or 5'-position(s) of the DHDPE molecule (in any possible combination), such as 3-iodo-DHDPE, 3,5-diiodo-DHDPE, 3,3'-diiodo-DHDPE, 3,5,5'-triiodo-DHDPE, 3,3',5,5'-tetraiodo-DHDPE, etc. For example, the 3-iodo-DHDPE is shown in FIG. 24.

Figure 25:
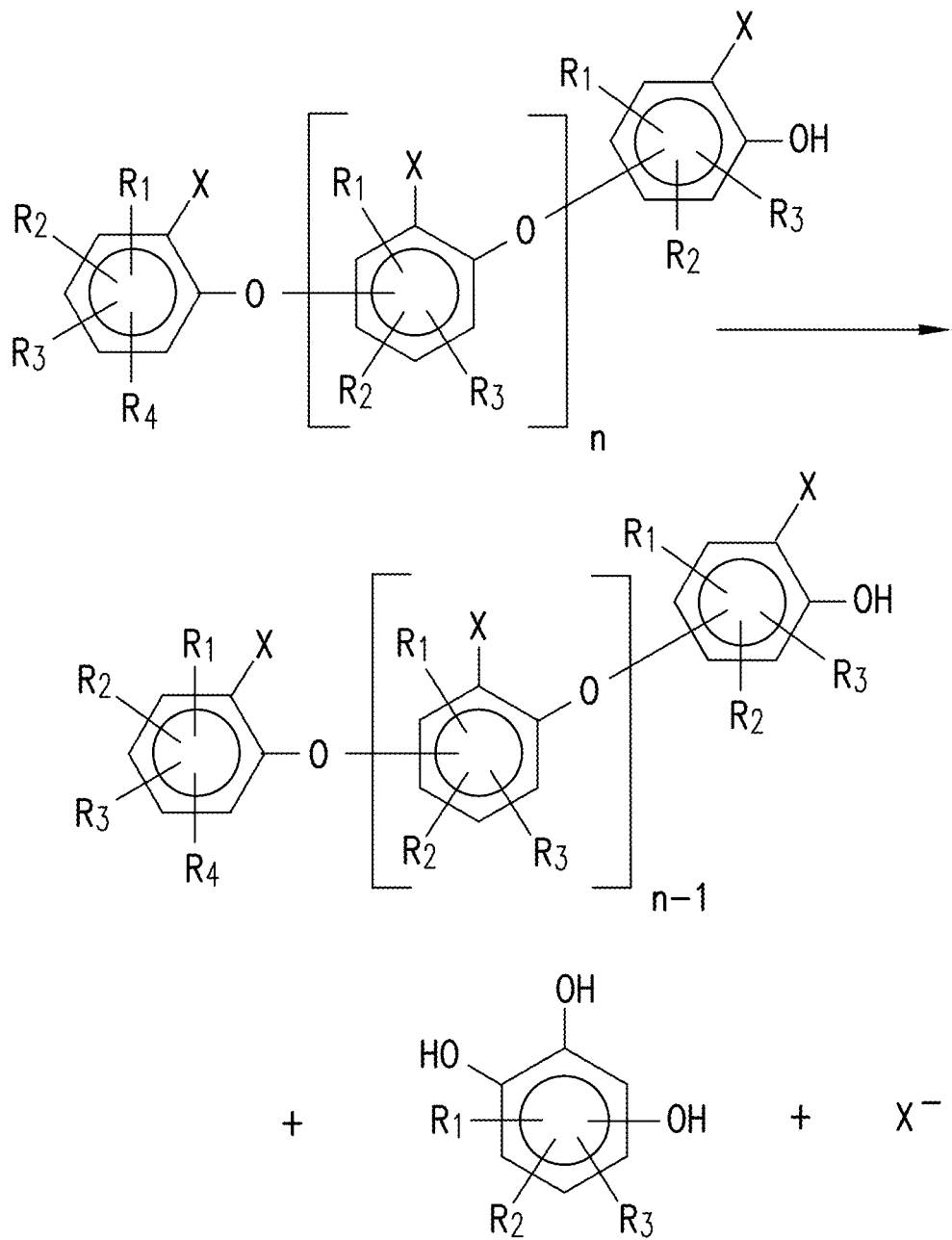
FIG. 25 is a diagram of a dehalogenation and cleavage reaction with a formula for a polymer embodiment of the present invention for use as an antioxidant and/or free radical scavenger.

As supported by the classes of compounds and examples in FIGS. 21-24, embodiments of the present invention may potentially include anti-oxidant, anti-inflammatory and/or FROS scavenging polymers of halogenated phenol ring units of any length (i.e., halogenated or iodinated polyphenols) with each unit of the polymer linked by an ether or thioether linkage to its neighboring unit(s) of the polymer. As shown in FIG. 25, individual phenol ring units may be dehalogenated and released sequentially (one at a time) along with a benzenetriol or like product (depending on chemical formula) and a halide through discrete depolymerization reaction events or steps triggered by exposure of the polymer to oxidizing agents and/or free radicals. The number of units in a polymer may vary widely and may include polymers of 2-200 units in length, or alternatively polymers of 2-100 units, 2-50 units, 2-25 units, 2-10 units, or 2-5 units in length, but longer polymers are also possible. According to some embodiments, the polymers may have a minimum of three (3) units in a range having the same upper limits. In reference to FIG. 25, the number of units will depend on the number of units (n) inserted between the first and last unit in the chain or polymer. If n=0, then the total number of units in the chain or polymer would be two (2), and the starting molecule would be able of undergoing only one dehalogenation and cleavage reaction. If n=1, then the total number of units in the chain or polymer would be three (3), and the starting molecule would be able to undergo two rounds of dehalogenation and cleavage reactions, and so on. Therefore, the number (n) may vary from zero (0) to about the number of total units in the chain desired (e.g., 10, 25, 50, 100, 200, etc.).

Each round of dehalogenation and ether cleavage will consume an oxidizing agent or free radical from the chemical environment of the halogenated phenol ring polymer. In addition to consuming an oxidizing agent or free radical during the dehalogenation and cleavage reaction itself, the benzenetriol or like products of the cleavage and depolymerization reaction may further function as an anti-oxidant and/or free radical scavenger in a subsequent or side reaction. Thus, compounds or polymers according to embodiments shown in FIG. 25 may be used as a FROS scavenger with extended activity.

The substituents on each unit of the polymer or chain shown generally in FIG. 25 may vary similarly as described above in reference to other compounds. The substituents ($R_1$, $R_2$, $R_3$, and $R_4$), present on the phenol ring may vary and may each be, for example, a hydrogen, a hydroxyl, a sulfhydryl, an alkyl, a halogen, an amino, a nitro, etc., group. The leading or first unit in the chain will have four potentially variable substituents ($R_1$, $R_2$, $R_3$, and $R_4$), whereas the remaining units in the chain will have only three potentially variable substituents ($R_1$, $R_2$ and $R_3$) due to their being one less unoccupied carbon available on the rings of the remaining units. Although $R_1$, $R_2$ and $R_3$ may be the same on each unit and/or occupy the same positions, the identity of $R_1$, $R_2$ and $R_3$ may instead be different between units of the chain and/or occupy different positions on each respective unit of the chain.

According to another broad aspect of the present invention, a compound according to some embodiments may undergo dehalogenation without cleavage. According to these embodiments, a compound containing a halogenated phenol ring may contain a different type of bond (e.g., a C—C, C—N, or C—H bond), which is not generally cleaved when the phenol is dehalogenated in the presence of free radicals and/or oxidative agents. As observed, destabilization of the electron cloud of the phenol ring as a result of dehalogenation, does not appear to result in the cleavage of the C—C, C—N, or C—H bond in these cases. Instead, only the halogen of the phenol ring is replaced with a hydroxyl group to reach a lower energy state. As a caveat, a C—C bond or linkage may become cleaved in some circumstances depending on the identity of the starting compound and the type of substituent linkage by the C—C bond. In other circumstances, however, a compound according to embodiments of the present invention may be designed to exploit this outcome with a C—C, C—N, or C—H bond (i.e., without a cleavable linkage), such that the compound will undergo a different kind of conversion or modification in response to free radicals and/or oxidative agents without cleavage of the C—C, C—N, or C—H bond. As an advantage, this approach may be preferred to avoid other cleavage products of the reaction.

Figure 26:
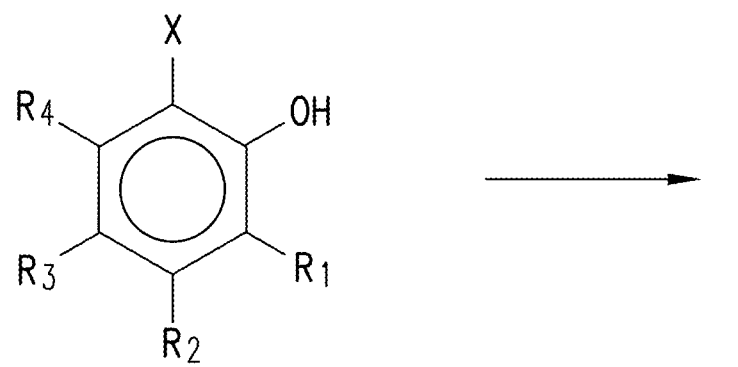
FIG. 26 is a diagram of a dehalogenation reaction without cleavage according to formula embodiments of the present invention.
Figure 26:
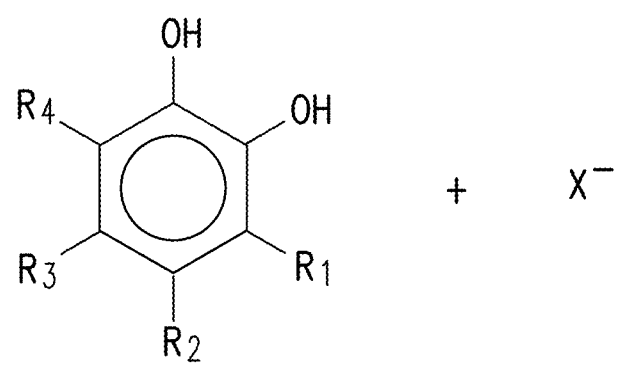

FIG. 26 provides a general class of compounds (Formula 26) which may be used according to embodiments of the present invention when it is desired that the product of the dehalogenation reaction be the same as the original or starting compound of Formula 26 except for the replacement of a halogen X on the phenol ring with a hydroxyl group. According to these embodiments, a halogenated phenol ring is bonded to four additional substituents $R_4$, $R_2$, $R_3$, and $R_4$. X is a halogen in the ortho position relative to a hydroxyl group (—OH) on the phenol ring (i.e., X is a halogen that is bonded to a carbon that is adjacent to a carbon bonded to a hydroxyl group (—OH) on the phenol ring). The halogen X may be selected from either iodine (I) or bromine (Br), but generally may not include fluorine (F) or chlorine (Cl). The identity of each of the remaining substituents $R_1$, $R_2$, $R_3$, and $R_4$ may vary and may include, for example, a hydrogen, a hydroxyl, a sulfhydryl, an alkyl, a halogen, an amino, a nitro, etc., groups. However, in contrast to the embodiments described above, these compounds do not have an ether or thioether bond or linkage on the phenol ring that could be cleaved as a result of the dehalogenation reaction. As a result, the product of the reaction closely resembles the starting compound except for the replacement of the halogen at the ortho-position relative to the hydroxyl group on the phenol ring with a hydroxyl group. According to some embodiments, substituents $R_1$, $R_2$, $R_3$, and $R_4$ would not include an aromatic ring, which is believed to encourage cleavage with dehalogenation.

According to these embodiments in FIG. 26, when a compound of Formula 26 comes in contact with an oxidizing agent or free radical, the halogen X is cleaved and removed from the phenol ring and replaced with a hydroxyl group. However, unlike compounds containing a cleavable linkage on the phenol ring, the C—C bond in this case is not cleaved in conjunction with, or spontaneously as a result of, the cleavage and removal of the halogen as part of the reaction. Therefore, in addition to a halide ($X^-$), the product of the reaction is an ortho-hydroxy phenyl compound with the substituents $R_1$, $R_2$, $R_3$, and $R_4$ still bonded to the phenol ring. Compounds or drugs formed by the dehalogenation reaction proposed in FIG. 26 may potentially include those linked to a halogenated phenol ring via a C—C linkage or bond (with the caveat that for some compounds, the C—C bond may become cleaved). According to these embodiments where cleavage does not occur, the starting compound would have the chemical structure of the drug compound except that a hydroxyl group (—OH) on the phenol ring of the drug product of the reaction is replaced with the halogen (X) in the starting compound. Compounds of the present invention according to Formula 26 may be cloaked (i.e., their activity is masked) but may become converted into bioactive products as a result of the dehalogenation reaction in the presence of FROS in the targeted tissue or cells. Compounds according to these embodiments may include modified thyroid hormones, such as a halogenated thyroid hormone, that are converted into thyroid hormone by dehalogenation.

Alternatively, compounds of the present invention according to Formula 26 may include compounds that consume oxidants and/or free radicals during the dehalogenation reaction, but which generally do not form a bioactive compound or drug. In other words, the product of the dehalogenation reaction may be partially, mostly, or completely biologically or medically inert. As an example, such compounds may include diiodotyrosine (DIT). However, some compounds according to these embodiments may form products that function as an anti-oxidant and/or free radical scavenger in a subsequent or additional reaction(s).

FIG. 27 provides an example of an embodiment of the present invention (according to the general Formula 26 in FIG. 26) for the targeted delivery of a drug, L-DOPA, to targeted cells or tissues, which may be useful for the treatment of Parkinson's disease. According to these embodiments, a mono-halogenated tyrosine compound (e.g., monoiodo-tyrosine or MIT, such as 3-iodo-4-hydroxy-L-phenylalanine or 3-iodo-tyrosine) may be taken by or administered to an individual and converted to L-DOPA in a targeted tissue of the individual in response to free radicals and/or oxidative agents present in the targeted tissue. The C—C bond between the halogenated phenol ring and the remainder of the mono-halogenated tyrosine molecule is not cleaved during the dehalogenation reaction triggered by the presence of free radicals and/or oxidative agents in the targeted tissue. Therefore, the product of the reaction, L-DOPA, may be delivered to targeted sites within the body of the individual due to elevated levels of free radicals and/or oxidative agents present at these sites without the production of a benzenetriol or like product. According to this embodiment, X is a halogen in the ortho position relative to a hydroxyl group (—OH) on the phenol ring (i.e., X is a halogen that is bonded to a carbon that is adjacent to a carbon bonded to a hydroxyl group (—OH) on the phenol ring). The halogen X may be selected from either iodine (I) or bromine (Br), but generally may not include fluorine (F) or chlorine (Cl).

Another example embodiment of the present invention may include a compound similar to the mono-halogenated tyrosine compound shown in FIG. 27 but with the positioning of the halogen X and hydroxyl group reversed (e.g., 3-hydroxy-4-iodo-L-phenylalanine). This compound would also be converted to L-DOPA by dehalogenation in the presence of free radicals and/or oxidative agents. According to these embodiments, the L-DOPA product of these reactions may also be further converted into dopamine via the activity of a DOPA decarboxylase enzyme present in the targeted tissue.

According to other embodiments, a dehalogenation reaction without cleavage may also be used to generate dopamine directly. For example, a mono-halogenated tyramine with the halogen at the 3-position, such as 3-iodo-tyramine, which is like dopamine but with a halogen, such as iodine, in place of one of the hydroxyl groups, may be used as a starting compound. In the presence of FROS, a 3-dodo-tyramine starting compound may be converted by dehalogenation without cleavage into dopamine. Similarly, as described above in reference to L-DOPA, the positioning of the halogen and the hydroxyl group may be reversed relative to the mono-halogenated tyramine compound. Such a 3-hydroxy-4-iodo-phenethylamine compound may also be used to generate dopamine by dehalogenation without cleavage in the presence of FROS. Much like the MIT and 3-hydroxy-4-iodo-L-phenylalanine compounds, the 3-iodotyramine and 3-hydroxy-4-iodo-phenethylamine compounds may be used to treat Parkinson's disease by releasing or generating dopamine in a targeted tissue of the brain.

According to other embodiments of the present invention, reverse T3 or rT3 (i.e., 3,3',5'-triiodothyronine) may also be used instead of MIT to form L-DOPA in the body. As described above in connection with FIG. 22, reverse T3 is converted to MIT via a dehalogenation and cleavage reaction. However, the MIT produced by this reaction may then be subsequently converted to L-DOPA by an oxidative de-iodination reaction without cleavage as described immediately above in reference to FIG. 27. Therefore, rT3 may be converted to L-DOPA through a two-step process according to these two reactions in combination. As also described above, the L-DOPA once formed may then be converted into dopamine in the targeted tissue, such as by endogenous enzymes. Reverse T3 has no measurable thyroid hormone activity and is believed to be generally inert unless it is converted into other compounds. Therefore, the inertness of rT3 allows it to be taken by or administered to an individual with little concern for cross-reactivity or side effects except by its downstream products (i.e., particularly L-DOPA or dopamine). Accordingly, compositions of the present invention may further include those comprising MIT and/or reverse T3 that may be used for the treatment of disease, such as Parkinson's disease. Like the monoiodo-tyrosine (MIT) compound in FIG. 24 (or the monoiodo-phenylalanine alternative), reverse T3 is able to more effectively cross the blood-brain barrier (BBB) relative to L-DOPA due to the presence of the iodines.

Similarly as described above for halogenated phenols linked to drug compounds by cleavable linkages, these halogenated phenol compounds with non-cleavable linkages in FIGS. 26 and 27 have the potential of providing improved targeted drug delivery to sites of disease and/or inflammation, increased stability, sustained release, and/or masked bioactivity in non-targeted tissues compared to existing therapies. In the case of the monoiodotyrosine compound in FIG. 27, for example, the presence of the halogen (e.g., iodine) on the phenol ring effectively blocks the ability of DOPA decarboxylase to recognize this compound. As a result, the ability of monoiodotyrosine to be converted into dopamine is masked or blocked until it is converted into L-DOPA by the dehalogenation reaction in a targeted tissue due to the presence of free radicals and/or oxidative agents. In addition, much like the halogenated phenol compounds described above with cleavable linkages to drug compound(s), potential CNS drug compounds according to these embodiments, such as monoiodo-tyrosine or 3-hydroxy-4-iodo phenylalanine (or the 3-iodotyramine and 3-hydroxy-4-iodo-phenethylamine compounds), may also have the benefit of increased hydrophobicity (due to presence of the halogen) leading to improved ability to cross the blood-brain barrier to exert their effects in the brain due to the presence of the halogen on the phenol ring. These embodiments may provide further benefits as a result of its simpler design and fewer products of the dehalogenation reaction (e.g., no benzenetriol-based or hydroxyhydroquinone-based compounds are produced) relative to the halogenated phenol compounds with cleavable linkages described above.

Embodiments of the present invention may further include compositions comprising a stereoisomer, such as a D- and L-isomer, of any of the compounds and formulas, or portions thereof, described herein in connection with FIGS. 1-29 that are asymmetric or chiral.

According to some embodiments, any of the compositions, compounds and formulas of the present invention, and combinations thereof, such as those in FIGS. 1 through 29, including any salt, solvate, or hydrate thereof, may be formulated as pharmaceutical compositions in combination with a pharmaceutically acceptable carrier. Such pharmaceutical embodiments of the present invention may be formulated as pharmaceutical compositions comprising a therapeutically effective (or desired) amount of any of the compounds or formulas as described herein, such as in FIGS. 1 through 29, or a salt, solvate, or hydrate thereof, in combination with a pharmaceutically acceptable carrier.

For the various embodiments of compounds of the present invention formulated as pharmaceutical compositions in combination with a pharmaceutically acceptable carrier, examples of pharmaceutically acceptable carriers and other suitable additives and adjuvants for pharmaceutical compositions that may be used in combination with embodiments of compounds of the present invention for taking by, or administration, providing or giving to, an individual, subject, or patient include those known to those skilled in the pharmacological or pharmaceutical arts. As used herein, such pharmaceutically acceptable carriers may be either liquid or solid and may include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, fillers, diluents, disintegration agents, lubricants, sweetening agents, flavoring agents, dyes, glidants, wetting agents, etc., and combinations thereof. For a description of suitable pharmaceutical compositions, carriers, etc. that may be used in formulating pharmaceutical compositions and compounds of the present invention, see, for example, Remington, *The Science and Practice of Pharmacy*, (University of the Sciences in Philadelphia, 21st ed., Lippincott Williams & Wilkins Co., 2005). See also, for example, U.S. Pat. Nos. 7,390,808, 7,354,928, 7,348,325, 7,326,713, and 7,282,504 (the contents and disclosures of which are incorporated herein by reference) for a description of suitable pharmaceutical compositions, carriers, etc., that may be used with pharmaceutical compositions and compounds of the present invention.

Except insofar as any conventional pharmaceutical carrier is incompatible with embodiments of the compounds or compositions of the present invention, their potential use in pharmaceutical compositions of the present invention is contemplated. Embodiments of the pharmaceutical compositions and formulations of the present invention may utilize different types of carriers depending on whether they are to be taken or administered in solid, liquid or aerosol form and whether they need to be sterile for certain routes of administration, such as local or systemic injection or infusion.

For embodiments of compounds of the present invention formulated as pharmaceutical compositions in combination with a pharmaceutically acceptable carrier, examples of pharmaceutically acceptable carriers may further include other delivery systems and reagents known in the art. Where appropriate, such delivery systems or reagents may include, for example, liposomes, microparticles or nanoparticles, microcapsules, emulsions, polymers, etc., or any combination thereof. Liposomes may be coated with opsonization-inhibiting moieties or molecules (e.g., PEG) to avoid detection by the immune system and may be specifically formulated and/or associated with other molecules, antibodies, or conjugates to improve delivery, intake, and/or specificity into specific tissues or cells. See, e.g., Szoka et al., "Comparative properties and methods of preparation of lipid vesicles (liposomes)," *Ann. Rev. Biophys. Bioeng.*, 9:467 (1980); Immordino, M. L., "Stealth liposomes: review of the basic science, rationale, and clinical applications, existing and potential," *Int. J Nanomedicine* 1(3):297-315 (2006); Samad, A., "Liposomal Drug Delivery Systems: An Update Review," *Current Drug Delivery* 4(4): 297-305 (2007); and Gregoriadis, G., *Liposome Technology* (Three-Volume Set), ($3^{rd}$ Ed., Informa Healthcare, 2006), the contents and disclosures of which are incorporated herein by reference in their entirety. See also, e.g., U.S. Pat. Nos. 4,501,728, 4,837,028, and 5,019,369, the contents and disclosures of which are incorporated herein by reference.

A therapeutically effective amount of a compound may include an amount of the compound effective to achieve a desired result or purpose or therapeutic benefit, including the effective treatment, alleviation, abatement, inhibition, prevention, management, etc., of inflammation, disease, and/or oxidative or free radical stress in an individual, or any symptoms associated with inflammation, disease, and/or oxidative or free radical stress. Determination of a therapeutically effective amount of a compound may be carried out in a manner known to those skilled in the art. For example, a therapeutically effective amount may comprise any appropriate dosage depending on the exigencies of a given situation including the age, gender, weight, etc. of the individual to be treated. To determine an amount or dosage that is appropriate for taking by or administration to an individual, subject, or patient, treatment dosages may be titrated to optimize safety and effectiveness. Lower than expected dosages may be administered first to an individual, subject, or patient, and these dosages may then be titrated upward until a therapeutically effective and safe concentration amount (or a potentially unsafe concentration or amount) is reached.

A therapeutically effective amount or dosage for a particular compound of the present invention may be determined or predicted from empirical evidence. Dosages or concentrations tested in vitro for embodiments of compounds of the present invention may provide useful guidance in determining therapeutically effective and appropriate amounts for in vivo administration. For example, a therapeutically effective dose of a compound according to embodiments of the present invention may be estimated initially from values obtained from any cell culture or in vitro assay. Such values may be used, for example, to translate into appropriate amounts for use in animal testing or for clinical trials in humans. Determining an appropriate dosage for an embodiment of a compound of the present invention may be discerned from any and/or all information or data available from any assay or experiment performed.

Animal testing of predicted dosages for compounds of the present invention may provide additional indication of a proper dosage or therapeutically effective amount for other types of animals, including humans. For example, a proper dosage or therapeutically effective amount of a compound of the present invention may be deduced from an amount that results in a circulating concentration of the compound in a test animal that roughly approximates concentrations shown to be effective according to cell culture and/or in vitro assays. Test animals may be used initially to determine the effectiveness and/or safety at such a circulating concentration or to determine or extrapolate a useful dosage or therapeutically effective amount of the compound for other animals, such as humans.

Toxicity and therapeutic efficacy of such a compound may be determined or predicted from any standard pharmaceutical procedures based on any cell culture or in vivo data. For example, an $LD_{50}$ value (i.e., dose lethal in 50% of the population) and an $ED_{50}$ value (the dose therapeutically effective in 50% of subjects according to a certain criteria) may be determined for a given compound in an animal test subject, and the ratio of $LD_{50}/ED_{50}$ may be expressed as a therapeutic index. Compounds that exhibit a high therapeutic index may indicate that higher concentrations of the compound are safe and non-toxic and/or that lower doses may be efficacious in an individual, subject, or patient. However, a lower therapeutic index may indicate that only lower (and perhaps ineffective) concentrations of a compound may be acceptable in terms of safety. The level of a compound in the blood or plasma of an individual, subject, or patient may be measured or monitored by any known technique including, for example, high performance liquid chromatography. In most cases, an appropriate dosage or therapeutically effective amount of a compound will be a balance of factors mainly including efficacy and safety. Furthermore, a therapeutically effective amount of a compound may vary depending on the particular composition and mode of administration.

According to another broad aspect of the present invention, methods are provided for effectively treating, alleviating, inhibiting, preventing, managing, etc., inflammation, disease, and/or oxidative or free radical stress in an individual, subject, or patient, or any symptoms associated with inflammation, disease, and/or oxidative or free radical stress in an individual, subject, or patient, by a composition or compound of the present invention, or a salt, solvate, or hydrate thereof administered to, or taken by, the individual, subject, or patient. A compound of the present invention may be administered to an individual, subject, or patient having or experiencing (or suspected of having or experiencing) inflammation, disease, and/or oxidative or free radical stress, or any symptoms associated with inflammation, disease, and/or oxidative or free radical stress. Indeed, a compound of the present invention may be taken by, or administered, provided or given to, an individual, subject, or patient having or experiencing (or suspected of having or experiencing) a condition, disease or inflammation associated with elevated levels of FROS.

These methods of treatment embodiments may comprise taking, delivering or administering a composition comprising one or more of the compounds of the present invention, such as those in FIGS. 1 through 27, or a salt, solvate, or hydrate thereof, perhaps in combination with a pharmaceutically acceptable carrier. Such a method may comprise a therapeutically effective amount of the compound taken by or administered to an individual. A therapeutically effective amount or dosage for a particular compound of the present invention may be adjusted after administering an initial dosage or amount by monitoring progress against inflammation, disease, and/or oxidative or free radical stress in an individual, subject, or patient, or against any symptoms associated with inflammation, disease, and/or oxidative or free radical stress in an individual, subject, or patient. Although release or formation of the product of the dehalogenation reaction may occur spontaneously in FROS containing tissues, release or formation of the product of the dehalogenation reaction may also be induced by externally applied radiation to the body of an individual being treated, such as focused radiation at a particular location(s) within the body of the individual.

Progress against inflammation, disease, and/or oxidative or free radical stress, or one or more symptoms thereof, may be monitored or measured in terms of efficacy and safety in response to administration of a composition or compound of the present invention and may be used to modify subsequent treatments. Progress against inflammation, disease, and/or oxidative or free radical stress, or one or more symptoms thereof, may be monitored or measured by any known pathological or clinical test or procedure for a given disease, including, for example, any known genetic, molecular, or biochemical techniques using tissue biopsies, blood samples, etc. There are numerous research methods, reagents, and/or diagnostic kits, assays and tools known and available in the art for measuring or monitoring progress against a disease (e.g., gene expression, molecular markers, genetic testing, labels, antibodies, karyotyping, chemical detection, etc.). In addition, progress against disease may be monitored according to any known or established veterinary, medical, and/or pathological technique (e.g., by observation of symptoms, etc.). Although such techniques, assays, reagents, and/or diagnostic kits are numerous, it is envisioned that any such method, reagent, and/or diagnostic procedure or kit, as well as any known or established veterinary, medical, research, and/or pathology technique, may be used to monitor progress against disease. Progress against a particular disease or condition may be evaluated according to known and available methods and diagnostics for that particular disease or condition as chosen by a qualified physician, veterinarian, or scientist attending to the care or treatment of an individual, subject, or patient being treated.

According to embodiments of present compositions, the exact formulation, route of administration, and dosage of a particular compound may be chosen according to the judgment of a skilled scientist, veterinarian, or physician in view of the characteristics and conditions of an individual, subject or patient. Factors considered in determining an appropriate dosage or therapeutically effective amount for an individual, subject, or patient in clinical settings may include the manner/route of administration, timing of administration, rate of excretion, target site, disease or physiological state, medical history, age, sex, physical characteristics, other medications, etc. This list of factors is illustrative and not exhaustive, and may include any or all factors which might be considered by a skilled scientist, veterinarian, or physician (as the case may be) in determining an appropriate treatment. For appropriate considerations and guidance in determining a therapeutically effective amount or dosage as well as appropriate formulations and/or routes of administration, see, e.g., Remington, *The Science and Practice of Pharmacy*, (University of the Sciences in Philadelphia, 21st ed., Lippincott Williams & Wilkins, 2005); and Goodman & Gillman, *The Pharmacological Basis of Therapeutics*, (11$^{th}$ Edition, McGraw-Hill Professional, 2005).

An appropriate dosage or therapeutically effective amount for embodiments of the compounds or compositions of the present invention may be in the range of, for example, from about 0.1 to about 100 mg per kg of body mass per day, from about 0.5 to about 60 mg per kg of body mass per day, or from about 1.0 to about 40 mg per kg of body mass per day. According to some embodiments, a therapeutically effective amount may be formulated as a unit dosage amount, which may be in the range of from about 1.0 to about 500 mg, from about 1.0 to about 250 mg, or from about 5.0 to about 150 mg. However, the appropriate dosage or therapeutically effective amount for embodiments of the compounds or compositions of the present invention will depend on a consideration of relevant factors, including the relative levels of therapeutic effectiveness and safety, the mode of administration, etc., as well as available empirical data about the compound or composition according to the knowledge and expertise of one skilled in the relevant art.

According to embodiments of compounds of the present invention formulated as a pharmaceutical composition, such a pharmaceutical composition may be taken or administered in a variety of unit dosage forms depending on the method of administration. For example, unit dosage forms suitable for oral administration may include solid dosage forms, such as powders, granules, tablets, pills, capsules, suppositories, depots, or dragees; or liquid dosage forms, such as elixirs, syrups, suspensions, sprays, gels, lotions, creams, slurries, foams, jellies, ointments, salves, solutions, suspensions, tinctures, and/or emulsions. Because of their ease of administration, tablets and capsules may be used as an oral dosage unit form when solid pharmaceutical compositions are employed. Pharmaceutical compositions may further include time-release or sustained-release formulations. For parenteral administration, pharmaceutical compositions of the present invention may be formulated as sterile solutions, emulsions, and/or suspensions. Pharmaceutical compositions for topical administration may further include patches (e.g., dermal patches, creams, etc.) or sprays, and pharmaceutical compositions for pulmonary administration may include aerosols.

According to many embodiments, compounds of the present invention may include a compound comprising a halogenated phenol ring linked to a drug compound via a cleavable linkage, which may be liberated in a desired chemical (i.e., FROS-containing) environment. Therefore, methods of treatment according to some embodiments may include taking by, or administering, providing or giving to, an individual one or more of these compounds of the present invention, such as those in FIGS. 1 through 20, (e.g., as a pharmaceutical composition) to any individual, subject, or patient that may otherwise receive the same drug compound without the covalently attached halogenated phenol ring. According to other embodiments, novel compounds of the present invention may also include modified drug compounds that contain a halogenated phenol ring but do not contain a cleavable linkage to the phenol ring apart from the halogen. Such a modified drug compound may be converted without such cleavage to become the drug compound in a desired chemical environment. Therefore, methods of treatment according to some embodiments may include taking by, or administering, providing or giving to, an individual one or more of these alternatively modified drug compounds of the present invention, such as those in FIGS. 26 and 27, (e.g., as a pharmaceutical composition) to any individual, subject, or patient that may otherwise receive the same drug compound product formed by these embodiments in the appropriate chemical (i.e., FROS-containing) environment.

Generally speaking, present methods of treatment will depend on the nature of the drug compound formed linked to the halogenated phenol ring of a starting compound of the present invention (or formed by a non-cleavable starting compound of the present invention). Thus, if a specific drug compound X is used to treat disease or condition Y in an individual, then compositions comprising a starting compound of the present invention that releases or forms the same drug compound X in FROS tissues (as a result of the dehalogenation reaction) may generally be administered in the same clinical context(s) that drug compound X would be administered.

As an example, L-DOPA is a standard therapy for the treatment of Parkinson's disease. The disease is characterized by motor symptoms, and may later include cognitive and behavioral problems as well. Thus, according to embodiments of the present invention, a person determined to have, diagnosed as having, having or suspected of having Parkinson's disease, dopamine deficiency, or other neuromuscular disorder or symptoms may take or be given, provided, or administered a pharmaceutical composition comprising one or more of: 3-hydroxy-3'-iodo-thyronamine (FIG. 8A), 3-hydroxy-3'-iodo-thyronine (FIG. 8B), reverse T3 (FIG. 22), 3-hydroxy-4-iodo-phenylalanine, mono-iodotyrosine or MIT (FIG. 27), 3-iodotyramine and/or 3-hydroxy-4-iodophenethylamine. Such pharmaceutical may be administered orally, such as a tablet, etc., but may also be administered parenterally, especially if there are digestive issues. For treatment of Parkinson's with L-DOPA, a common dosage may include about 100 mg every 3 hours. Accordingly, a dosage amount for embodiments of the present invention may be about the same within an order or two of magnitude. However, as with any drug, the precise regimen and dosage will depend on a variety of factors including feedback from treatment according to good pharmaceutical management of the patient and symptoms. Indeed, some patients may receive a reduced dose or be excluded from treatment due to toxicity to the drug or extrapyramidal symptoms. As mentioned above, compounds of the present invention may be better able to diffuse across the BBB and/or minimize or eliminate the need for co-treatment with Carbidopa due to targeted delivery.

Another treatment example of the present invention may include delivering an antibiotic to a site of infection and/or inflammation. Sites of infection may be highly associated with inflammation and high FROS production. Thus, embodiments of the present invention may be used for targeted delivery of an antibiotic to a site of infection. Any antibiotic having a "linkable" substituent for linking to a halogenated phenol ring may be used as a starting compound. According to these embodiments, an individual determined to have, diagnosed as having, having or suspected of having an infection may take or be given, provided, or administered a pharmaceutical composition comprising a starting compound of the present invention that will produce or release an antibiotic in a targeted tissue. For example, such a composition may comprise Compound 18 (in FIG. 18) for release of penicillin or related compounds.

According to another set of treatment examples of the present invention, a composition comprising a starting compound of the present invention may be taken or administered that will produce or release an analgesic (pain reducer) in a targeted tissue. Sites of tissue or bone injury, burns, autoimmunity, bone or joint degeneration, infection, disease and/or inflammation may be associated with pain symptoms as well as high levels of FROS. Thus, embodiments of the present invention may be used for targeted delivery of an analgesic to these sites in the body. Accordingly, embodiments of the present invention may include methods of taking by, or administering, giving or providing to, an individual having or experiencing pain or discomfort, a pharmaceutical composition comprising a starting compound of the present invention that will produce or release an analgesic drug in targeted tissues (i.e., location(s) of pain). As one example embodiment, a composition comprising Compound 11A (in FIG. 11A) may be used to produce or release acetaminophen at a site of pain, especially for mild pain. According to other example embodiments, a composition comprising Compound 11B (in FIG. 11B) or Compound 11C (in FIG. 11C) may be used to produce or release dihydromorphinone (DILAUDID®) or morphine, respectively, at a site of pain, especially for treatment of more severe or extreme pain.

According to another set of treatment examples of the present invention, a composition comprising a starting compound of the present invention may be taken or administered, provided or given that will produce or release an anti-inflammatory drug in a targeted tissue, which may also have analgesic effects. Sites of tissue or bone injury, such as cuts, burns, breaks, etc., autoimmunity, bone or joint degeneration, such as arthritis, etc., infection, and/or disease, such as cancer, etc., may be associated with inflammation and pain symptoms as well as high levels of FROS. Thus, embodiments of the present invention may be used for targeted delivery of an anti-inflammatory/analgesic to such sites in the body. Accordingly, embodiments of the present invention may include methods of taking by, or administering, providing or giving to, an individual having or experiencing inflammation and/or pain or discomfort, a pharmaceutical composition comprising a starting compound of the present invention that will produce or release an anti-inflammatory drug in a target tissue (i.e., at the location of inflammation). As one example embodiment, a composition comprising Compound 19A (in FIG. 19A) may be used or administered to produce or release aspirin at sites of inflammation and/or pain or discomfort. As another example, a composition comprising Compound 19B (in FIG. 19B) may be used to produce or release naproxen at sites of inflammation and/or pain or discomfort. As yet another example, a composition comprising Compound 19C (in FIG. 19C) may be used to produce or release ibuprofen at sites of inflammation and/or pain or discomfort to reduce pain, inflammation and/or swelling.

In a related treatment example, particularly when a more potent anti-inflammatory effect is desired, a pharmaceutical composition comprising a starting compound of the present invention that will produce or release a steroidal anti-inflammatory, such as cortisol or cortisone, may be used. Accordingly, embodiments of the present invention may include methods of taking by, or administering, providing or giving to, an individual having or experiencing inflammation and/or pain or discomfort, a pharmaceutical composition comprising a starting compound of the present invention that will produce or release a steroidal anti-inflammatory drug in a target tissue (i.e., at location(s) of inflammation, that may be). For example, a composition comprising Compound 13 (in FIG. 13) may be used to produce or release cortisone at sites of inflammation. Again, these embodiments may be used to deliver the steroidal anti-inflammatory to high FROS-producing sites in the body, such as sites of tissue injury, autoimmunity, bone or joint degeneration, such as arthritis, etc., infection, and/or disease, such as cancer, etc., that may be associated with inflammation and/or swelling of tissue.

As yet another treatment example of the present invention, a pharmaceutical composition comprising a starting compound that will produce or release an anti-tumor, chemotherapy and/or cytotoxic compound or agent at a cancerous or tumor site. Sites of cancerous cells, tissues or tumors are often associated with inflammation and high FROS. Thus, compositions and methods of the present invention may be used for targeted delivery of such compounds or agents to cancerous cells, tissues or tumors. Accordingly, embodiments of the present invention may include methods of taking by, or administering, providing or giving to, an individual determined or diagnosed as having, having or suspected of having cancer, a pharmaceutical composition comprising a starting compound of the present invention that will produce or release a chemotherapeutic, anti-tumor or cytotoxic drug at or in a target tissue (i.e., at sites or locations of cancerous cells or tissues and/or tumors). As one example embodiment, a composition comprising Compound 16 (in FIG. 16) may be used or administered to produce or release methotrexate in or near cancerous tissues or cells and/or tumor sites. As another example for targeted delivery of a chemotherapeutic agent to sites of cancerous cells or tissue and/or tumors, such a composition may alternatively comprise Compound 14 (in FIG. 14) for targeted delivery of 5-iodo-uracil to cancerous or tumor sites in the body.

Another treatment example of the present invention may include methods of administering or delivering serotonin to an individual. Deficient levels of serotonin are associated with psychological conditions, such as depression, anxiety, and some personality disorders. Serotonin reuptake inhibitors (SRIs) or selective serotonin reuptake inhibitors (SSRIs) are existing therapies. It is theorized that serotonin deficiency may be related to ischemic conditions and/or mini-stroke events at key locations in the brain that can lead to production of FROS, which can damage cells or tissue and impair function. Also, regions of the brain responsible for production of serotonin, such as the Raphe nuclei, may be damaged by FROS. Accordingly, embodiments of the present invention may include methods of taking by, or administering, providing or giving to, a person determined to have, diagnosed as having, having or suspected of having a serotonin deficiency, depression, anxiety or like symptoms, a pharmaceutical composition comprising a starting compound of the present invention that will produce or release serotonin in a targeted tissue. For example, a composition comprising Compound 10 (in FIG. 10) may be administered. Compounds of the present invention may also be given or administered in addition to, or in conjunction with, standard therapies, such as serotonin, SRIs and/or SSRIs. Again, due to the presence of the halogenated phenol ring, the compound will diffuse across the BBB and enter the brain.

As yet another example, embodiments of the present invention may include methods of administering a pharmaceutical composition comprising a starting compound of the present invention that will produce or release estradiol or estrogen in a targeted tissue. For example, such a composition may comprise Compound 9 (in FIG. 9). Such a composition may be taken by, or administered, provided or given to, postmenopausal women having an estrogen deficiency. Tissue or cells that are estrogen dependent may be experiencing cellular stress, which could result in high FROS. Such compositions may also be used to target and treat some types of cancers or tumors that are inhibited by or sensitive to estrogen or its derivatives.

According to additional embodiments, novel compounds of the present invention may also include anti-inflammatory, anti-oxidant, and/or free radical scavenging compounds comprising a halogenated phenol ring with a cleavable linkage, but which may not release or produce a drug compound apart from its anti-inflammatory, anti-oxidant, and/or free radical scavenging ability. Such compounds may remove, consume or deplete oxidizing agents and/or free radicals from an in vivo environment or targeted tissue, which may be associated with inflammation and/or disease. Therefore, methods of treatment according to these additional embodiments may include taking by, or administering, providing or giving to, an individual one or more of these anti-inflammatory, anti-oxidant, and/or free radical scavenging compounds of the present invention, such as those in FIGS. 21 through 25, (e.g., as a pharmaceutical composition) to any individual, subject, or patient in need thereof.

According to these embodiments, such compositions comprising starting compounds represented in FIGS. 21-25 may be taken by, or administered, given or provided to, someone experiencing heightened levels of FROS and/or inflammation, either systemically or in a particular tissue, to scavenge, quench or consume FROS and thus protect cells and tissues of the body from damage. Such heightened levels of FROS and/or inflammation may be associated with a variety of diseases or conditions characterized by inflammation, immune reactions and/or altered metabolism, such as autoimmune conditions, arthritis, multiple sclerosis (MS), ischemic bowel disease, retrolental fibroplasias (RLF), ischemia and/or reperfusion associated with myocardial infarct or stroke, cachexia, sepsis, etc. Thus, in addition to providing a protective function, these antioxidant and/or FROS scavenging compositions may also be used to reduce, treat or alleviate symptoms associated with these diseases or conditions. These compositions may be used to treat or reduce symptoms associated with disease, such as cancer, etc., in addition to, or apart from, treatment with a drug. By reducing FROS, protecting cells and tissues and/or reducing inflammation, these compositions may be able to slow, contain or impede disease progression and/or mask its symptoms, possibly as an effective "cure," in some cases. By "mopping up" FROS present in a tissue, normal cells may be better able to survive and function normally, and stem cells may be able to migrate to affected areas and/or proliferate and differentiate to repair damaged tissue.

In addition, these antioxidant and/or FROS scavenging compositions comprising starting compounds in FIGS. 21-25 may be used or administered instead for preventative or prophylactic purposes, such as in normal or healthy individuals. An individual could take a composition comprising one of more of these compounds on a regular basis, much like a daily vitamin, as a means of general protection against cell or tissue damage resulting from FROS. Such regular preventative use of these compositions may minimize or avoid chances for disease, improve quality of life and vigor, as well as provide an anti-aging benefit. In many cases, the cause of disease as well as its progression and symptoms may be mediated by FROS generation in tissues, which may result in wear-and-tear over time and lead to tissue damage, impaired tissue function and possibly cell death. Thus, compositions of the present invention may be useful in protecting these cells and tissues over time. For example, compositions of the present invention may be used to protect cells and tissue in highly metabolic regions of the brain, such as the substantia nigra, from insults caused by high levels of FROS to avoid tissue damage and disease and improve cognitive function.

Embodiments of the present invention may also include compositions, such as pharmaceutical compositions, comprising any compound linked to a halogenated phenol ring described herein that produces a colored or detectable product(s) in the presence of FROS. Such compounds may include, for example, any indigogenic compound represented in FIGS. 28 and 29. Methods of taking by, or administering, providing or giving to, an individual or patient any such compositions are further provided, wherein the detectable product(s) of the dehalogenation reaction may then be detected or measured systemically, in bodily fluids, or in a specific tissue(s) of the individual or patient in which the detectable compound is formed (i.e., in situ or by taking a sample as part of an assay) for diagnostic purposes (see below). If the starting compound administered is any compound represented by FIGS. 1-25, 28 and 29, then the product that may be detected or measured may include a benzenetriol-based or benzenetetrol-based product, as a quinone and/or phenolic species, or a halide. In the case of detection or measurement of a halide, the halide may be produced by any of the starting compounds represented by FIGS. 1-29. As discussed further below, the benzenetriol-based or benzenetetrol-based product(s) may be detected or measured, for example, by absorbance, nuclear magnetic resonance (NMR), mass spectrometry (MS), chemical test, etc. For absorbance, the benzenetriol-based or benzenetetrol-based product(s) may be detected or measured by a spectrophotometer at wavelength absorptions in the UV range, and in the color range for quinone species. Halides, such as iodide, may be detected or measured by known methods. The amount, level and/or rate of increase of these detectable products may be indicative of the amount or level of FROS systemically or in a particular tissue, which may indicate the existence and stage of disease or inflammation.

In any case, the ability to detect or measure systemic levels of one or more detectable product(s) of the reaction from a starting compound of the present invention by taking a sample from an individual provides a useful tool that may be used as a replacement for detection of C-reactive protein (CRP) as a measure of general inflammation or FROS load in the body of an individual, which may indicate the presence of disease.

Thus, according to embodiments of the present invention, a starting compound of the present invention may be taken by, or administered, provided or given to, an individual, and product(s) of the dehalogenation reaction (e.g., benzenetriol-based or benzenetetrol-based product(s) in the case of starting compounds in FIGS. 1-25, 28 and 29; and/or halides in the case of starting compounds in FIGS. 1-29) may be detected or measured either from a sample, such as blood, urine, or tissue biopsy. Such a sample may be further processed to isolate, purify, concentrate, etc., the detectable product from the sample prior to detection or measurement.

As described further below in connection with FIGS. 28 and 29, indigogenic compounds are cleaved by the dehalogenation reaction to form visibly colored indigo-like products in the presence of FROS. The indigo-like compounds formed by these reactions may also generally have higher residence time where formed (i.e., in high FROS tissues), allowing for their detection in situ as an indication of sites of inflammation and/or disease. However, some amount of indigo-like product (once formed) may flow away from its site of formation, which may be detected or measured systemically from a sample. Indeed, the indigo-like compound is preferably not permanent in the tissue and will clear from the tissue as some rate. As further explained below, other products of the reaction without residence time in the tissue may also be detected or measured systemically for diagnostic purposes. As described above, according to some embodiments, any compound of the present invention, such as those represented in FIGS. 1-29, may be administered, and the amount of product (e.g., benzenetriol-based product, benzenetetrol-based product and/or halide) may be detected and/or measured.

Figure 28A:
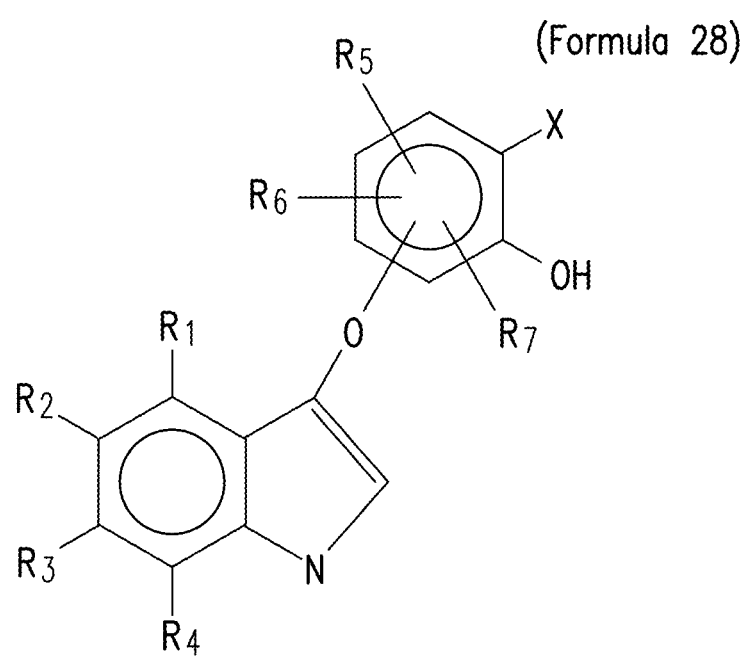
FIG. 28A is a formula for indigogenic embodiments of the present invention for the production of a detectable product for diagnostic purposes.
Figure 28B:
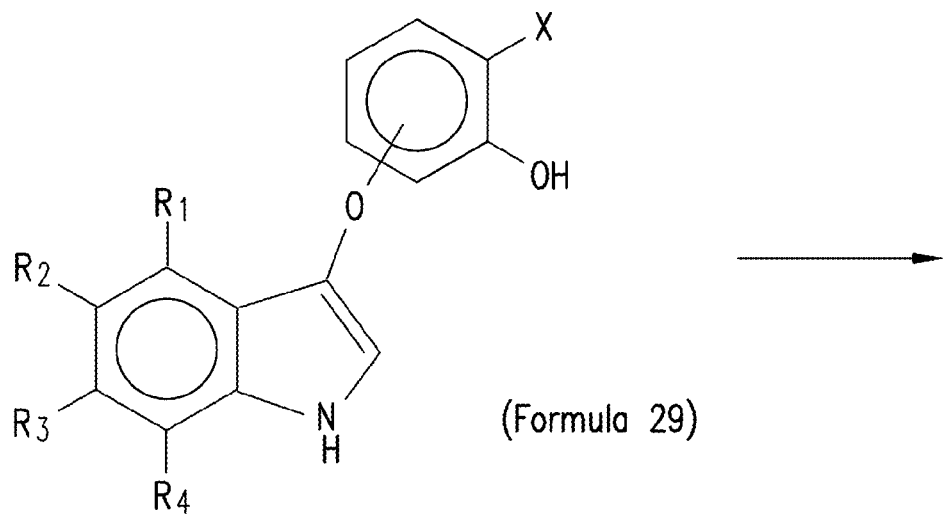
FIG. 28B is a diagram of a dehalogenation and cleavage reaction according to a formula of indigogenic compounds of the present invention for the formation of detectable or radio-isotope-carrying compounds that may have higher residence times in target FROS-containing tissues.
Figure 28B:
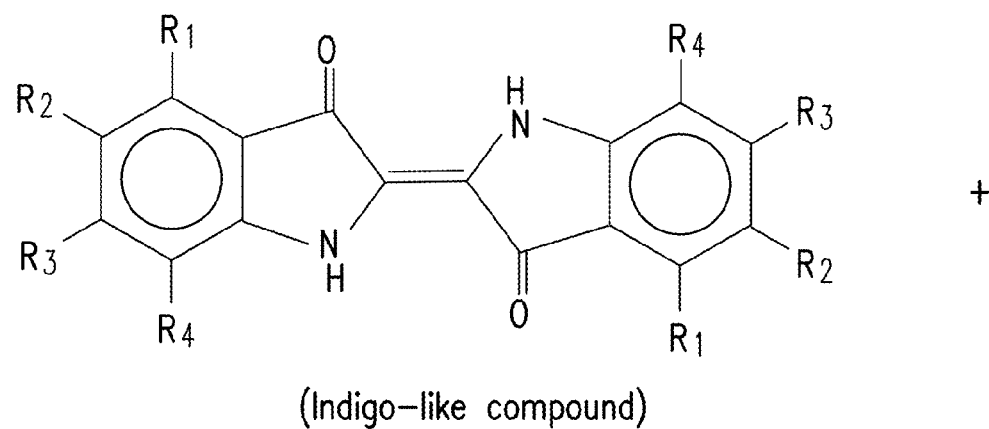
Figure 28B:
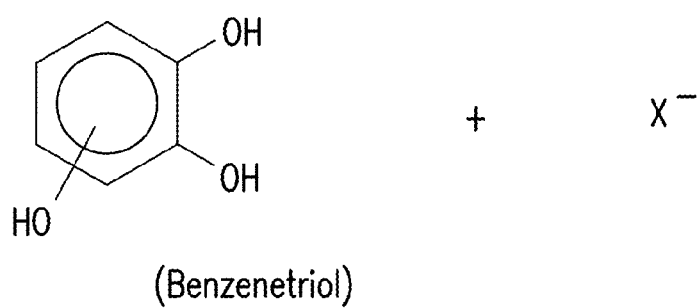
Figure 29A:
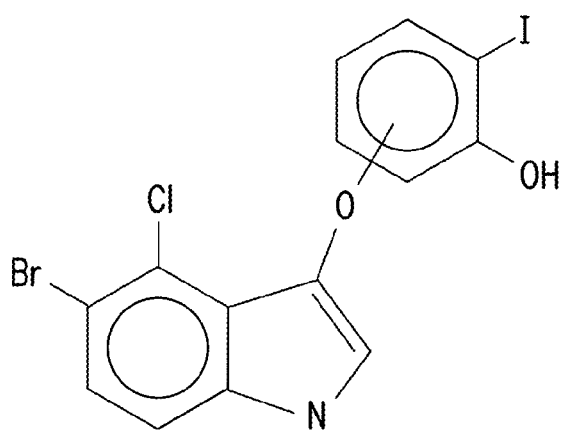
FIG. 29A is an indigogenic compound embodiment of the present invention containing a bromine and chlorine to produce a detectably colored indigo-like product.
Figure 29B:
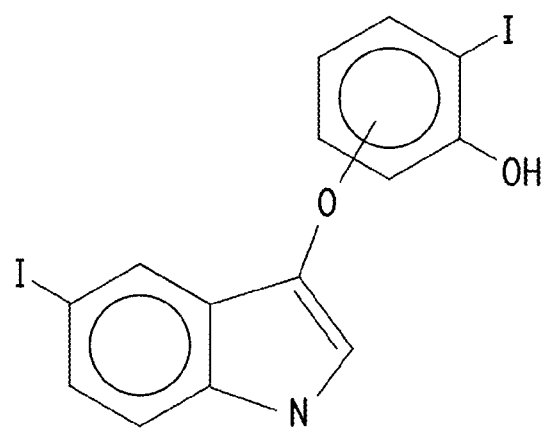
FIG. 29B is an indigogenic compound embodiment of the present invention containing an iodine to produce a detectable and radio-opaque indigo-like product.
Figure 29C:
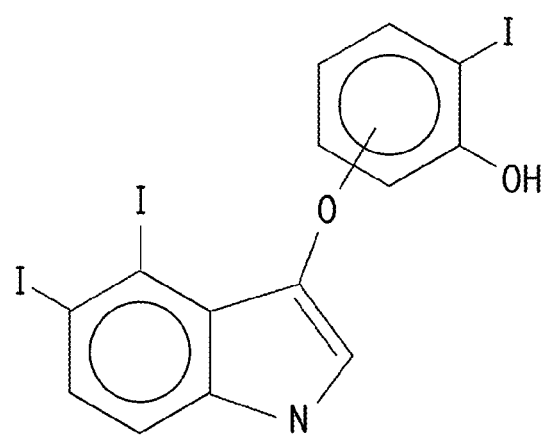
FIG. 29C is an indigogenic compound embodiment of the present invention containing two iodines to produce a detectable and radio-opaque indigo-like product.

Accordingly, embodiments of the present invention include methods of taking by, or administering, providing or giving to, an individual a composition comprising an indigogenic compound of the present invention, such as a starting compound represented in FIGS. 28 and 29, to an individual and detecting the formation of an indigo-like product. In those situations where the indigo-like product is detected in situ due to its residence time in tissues where it is formed, the product may be detected visually (in the case of a distinguishably colored product; e.g., FIG. 29A) or by radiography or X-ray imaging (due to the halogenated indigo-like compound being radio-opaque; e.g., FIGS. 29B and 29C). In the case of distinguishably colored indigo-like products, the product may be directly visualized, which may provide assistance, for example, during a surgical operation. In some cases, an intermediate of the dehalogenation reaction involving an indigogenic compound may be visualized by fluorescence caused by UV light excitation.

In each of the in situ contexts, the indigo-like product formed by the reaction from a starting compound of the present invention may be detected to determine sites of disease or cancer, such as ductal carcinoma, etc. In addition to cancer or tumors, FROS sites of formation and residence of an indigo-like product may also indicate sites of infection or other disease. In the case of CNS conditions or diseases, localization of an indigo-like product may provide information about affected areas for diagnosis. Different areas of the brain are associated with different cognitive and neurochemical functions. Thus, correlation between (i) behavioral symptoms and patient history and (ii) localization of FROS-producing indigo-like products to specific regions of the brain may provide strong evidence for a causal connection. For example, the substantia nigra (SN) of the brain is highly metabolic with high FROS in patients with Alzheimer's disease or dementia, which affects the dopamine tracts in the SN. The frontal lobe is associated with executive and analytical functions, which may also be affected in dementia, and the temporal lobes are associated with memory and may be affected with memory loss. The complementarity of disease detection and drug delivery (plus FROS scavenging) by the same chemical reaction allows for targeted treatments according to embodiments of the present invention to match sites of detection. Following detection, FROS scavengers may be effective at protecting these highly metabolic tissues from cellular and tissue damage to improve their function and reduce disease symptoms.

Even though indigo-like products of the reaction may have some amount of residence time in the tissue where they are formed, they do gradually and eventually diffuse away from their site of formation. Thus, these indigo-like products may be further detected or measured by other methods, such as absorbance, NMR, etc., using a sample taken from the individual.

Another method for diagnosis is the detection or measurement of $^{13}C$ containing products of the reaction from starting compounds containing this stable isotope in place of carbon 12. The presence of this stable isotope provides a basis for distinguishable detection of the product. Following its administration, such a product may be detected or measured by NMR or MS in the case of detection or measurement in a sample. Such detection may provide the same information as described above for other detectable products, such as high levels of PROS systemically or in a particular tissue, which may indicate disease and/or inflammation. Given that the $^{13}C$-containing product may be detected by NMR, it is theorized that magnetic resonance imaging (MRI) might potentially be used to detect localization of a detectable product in situ from a $^{13}C$ containing indigogenic compound. However, further work is needed to develop this technology.

Embodiments of the present invention may further include methods of taking by, or administering, providing or giving to, an individual similar indigogenic compound(s) containing radioactive isotopes (see below), which may be converted in an appropriate chemical (i.e., FROS-containing) environment (i.e., in an inflamed and/or diseased target tissue) to form a compound having a higher residence time where formed to preferentially irradiate such target tissue. Thus, methods of treatment according to some embodiments may include taking, administering, providing or giving a composition, such as a pharmaceutical composition, comprising a halogenated phenol linked indigogenic compound containing a radioactive isotope, such as according to the compounds or formulas 28 and 29 represented in FIGS. 28 and 29, to an individual, subject, or patient in need thereof. For example, such radioactive compounds of the present invention may be used to treat cancerous tissues, such as a tumor, and may be administered to a person having a cancerous tumor to locally irradiate the tumor due to its targeted delivery and prolonged residence time in these tissues.

According to embodiments of the present invention, whether for therapeutic, diagnostic or combined purposes, compositions and compounds of the present invention may be suitably administered by or given or provided for any known mode or route of administration. Such mode or route of administration may depend on the particular compound and/or condition to be treated and may be chosen to maximize delivery of a compound of the present invention to a desired target site in the body of an individual, subject, or patient. Pharmaceutical compositions and compounds may be administered in a number of ways, including any suitable enteral, parenteral, topical, or local mode or route, depending on whether local or systemic treatment is preferred and/or the specific area to be treated. Suitable enteral routes for administration may include oral, rectal, intestinal, and gastric. Suitable parenteral routes may include intravascular routes, such as intravenous (bolus and infusion), intrarterial, and intracardiac; mucosal routes, such as transmucosal (e.g., insufflation), sublingual, buccal, intranasal, pulmonary (e.g., inhalation), and vaginal; intracranial; intraocular; intrathecal; intraperitoneal; intramuscular; intradermal; subcutaneous; intramedullary; or intraosseus. Embodiments of the pharmaceutical compositions of the present invention may be further administered via topical or transdermal routes as well as by local injection at a desired site of action, including peri- and intra-tissue injections, such as at or near a site of disease and/or inflammation in the body of an individual, subject, or patient.

Compounds or compositions according to embodiments of the present invention may be administered for therapeutic and/or diagnostic purposes either as a single dose or as part of a dosage regimen. A dosage regimen may be adjusted to provide an optimum therapeutic response or diagnostic measurement. For example, several different doses may be administered daily or doses may be proportionally reduced as indicated by the exigencies of a therapeutic situation. By administering an embodiment of a compound or composition of the present invention as part of a dosage regimen, circulating concentrations may be allowed to reach a desired equilibrium concentration for a compound through a series of doses. For convenience, a predetermined total daily dosage may be divided and administered in portions during the day as required. The compounds may be administered according to a dosage regimen of from about 1 to about 5 times per day, for example, 1, 2 or 3 times a day.

According to a broad aspect of the present invention introduced above, diagnostic compounds or compositions forming detectable product(s) as a result of the dehalogenation reaction, along with diagnostic methods of using the same, are provided for the indirect detection, indication and/or measurement of FROS present systemically or in a particular tissue. Such detection or measurement of these products may serve as an indication of specific sites and/or systemic levels of FROS in the body of an individual, which may be an indication of inflammation, disease or pathology systemically or in a particular location or tissue. These embodiments may be based on compounds that form a colored or otherwise detectable product(s) upon exposure to an oxidative and/or free radical (FROS) containing environment, which may accompany disease or inflammation, and the amount of colored or otherwise detectable product may correlate or relate to the degree or level of oxidants and/or free radicals systemically or in a tissue, which may also indicate the stage or advancement of a disease.

According to some embodiments, the detectable product may include a cleavage product of the dehalogenation reaction that is detectable due to its properties or interaction with light or other electromagnetic radiation. For example, the detectable product may include a quinone or phenolic species formed by the dehalogenation and cleavage reaction from a variety of compounds of the present invention. For example, the detectable product may include a quinone, hydroquinone, hydroxyhydroquinone, benzenetriol-based or benzenetetrol-based product of the reaction as discussed further herein that may be produced from dehalogenation and cleavage of any of the compounds in FIGS. 1-25, 28 and 29 as described above, or from a thyroid hormone or an iodo-thyronine compound. Any of these compounds may be administered to the body of an individual, and the amount of the detectable product may be measured from a sample or biopsy taken from the individual. For any of these in vitro detection or diagnostic embodiments, a "sample" (or "test sample") from an individual may include both (i) a sample taken from an individual, as well as (ii) any sample derived therefrom by further processing, such as purification, concentration, etc. The term "from" in this sense, means directly or indirectly from the individual. A "sample" (or "test sample") from an individual may further include a sample produced by processing of a biopsy taken from the individual. The term "processing" means to perform any chemical procedure or technique to alter the sample and improve detection of a detectable product in a sample produced thereby.

Thus, detection of the detectable product may be used as an indication of the amount, level or degree of oxidants and/or free radicals (FROS) present systemically or in a particular tissue. The administered compound may generally (or preferably) be one that does not contain or give rise to a bioactive drug compound since the administered compound would be used in these instances primarily for production of the detectable product. However, the administered compound may include a FROS scavenger and/or anti-oxidant or anti-inflammatory agent. Indeed, the compound may serve a dual role as a FROS scavenger and a diagnostic compound that gives rise to a detectable product. Alternatively, it is also proposed that a compound containing a drug compound could be used simultaneously for diagnostic purposes with any incidental production of a detectable product detected in conjunction with treatment.

Quinones are uniquely colored and may thus be detected or measured by spectrophotometric methods of absorption, etc., at particular EM or light wavelengths or within ranges of EM or light wavelengths, or possibly by other methods, such as mass spectrometry (MS), nuclear magnetic resonance (NMR), chemical test, etc. For example, the products of the dehalogenation reaction may be detected or measured in terms of their characteristic peaks by NMR spectroscopy. The benzenetriol-based or benzenetetrol-based products of the dehalogenation reaction may resonate between (i) a phenolic or hydroxyl-form (or tautomer) and (ii) a keto-form (or tautomer) (i.e., as a quinone) in an equilibrium, which may be affected by an oxidative or reductive environment (i.e., affecting its oxidation state). Thus, both the phenolic and quinone species may potentially be detected or measured as an indication of FROS. A detectable product of the present invention may have a "hydroxy-quinone structure" including either or both, or any combination of, the phenolic and/or quinone species of a detectable product formed as a result of a dehalogenation and cleavage reaction from a starting compound of the present invention. A "hydroxy-quinone structure" further includes a detectable product having any combination of the alternative keto and hydroxyl groups at different sites on the detectable product (especially in the case of a detectable product having an intermediate or incomplete oxidation state). Although the body may have a tendency to reduce these structures to their more reduced form, a benzenetriol-based or benzenetetrol-based product formed from a starting compound of the present invention that has a "hydroxy-quinone structure" would include any collection of these products having any combination of keto and/or hydroxyl groups at each site (i.e., at each site where the hydroxyl groups of the detectable product would be located in its fully reduced form).

Phenolic species may be generally measured by absorbance at UV wavelengths, such as in a range from about 275 nm to about 285 nm. Any quinone species may also be detected or measured by UV absorbance within this same wavelength range. However, quinone species may also be detected or measured by visible coloration and by absorbance of light within visible color wavelength ranges. However, the precise range of wavelengths of absorbance within the visible light spectrum (and/or the coloration of the product for direct detection) will depend on the exact chemical formula of the quinone species, which will depend on the starting compound of the present invention.

Since the quinone species may be differentially detected within a visible color range, the phenolic and quinone species may be separately detected and/or measured, and their relative amounts may be expressed as a ratio as a method for improved accuracy and/or standardization. As an alternative method to improve accuracy and/or standardization, the amount of benzentriol-based or benzenetetrol-based products of the reaction in either the phenolic or quinone form may be compared against a control or in relation to a series of different titrated amounts of an administered starting compound.

Regardless of the detection method, however, the quinone and/or phenolic products of the dehalogenation reaction may be first concentrated, purified, isolated, etc., from a sample, such as blood, sputum or urine, or tissue biopsy according to any known technique(s), or combinations thereof, such as by solvent extraction (e.g., separation into an organic phase), chromatography, etc., prior to measurement. In the case of blood, the hemoglobin and/or red blood cell fraction (and possibly all cellular components) may be removed from the sample by any known method (e.g., centrifugation, etc.). The benzenetriol-based compound and benzenetetrol-based (i.e., phenolic) compounds may be relatively more soluble in water compared to the quinone species. Thus, phase separation may be used not only to isolate, purify or concentrate the product, but possibly also to selectively separate the species. One confounding factor is that the relative amounts of the phenolic and quinone species may depend on the degree of oxidation or reduction, and resonance between these forms may be partial or incomplete. In other words, each site containing a hydroxyl or keto group is capable of independently resonating. Therefore, a sample, or isolate, purification or concentration thereof, may be first exposed to either an oxidizing or reducing agent to drive all of these substituents to one or the other form or species (i.e., a keto or quinone species, or a hydroxyl or phenolic species, respectively) to help standardize the measurement. As an alternative, embodiments of the present invention further contemplate the detection or measurement of a halide, such as iodide, produced by the dehalogenation reaction according to any known method, such as color indicator detection kits, slow neutron activation assay, NMR, etc., that is present in a sample taken from an individual as an indication of the level of FROS.

According to some embodiments, a product of the dehalogenation reaction may be detected or measured over a time course following administration of a starting compound to an individual by taking a series of samples from the individual with the detection profile providing information about the level of FROS and/or degree or extent of inflammation or disease. For example, a time plot showing quick rise in the level of the detectable product, such as an indigo-like compound, benzenetriol-based compound, benzenetetrol-based compound or halide, in a sample following administration of a starting compound may be indicative of a high level of FROS and/or inflammation or disease in the body. In contrast, a relatively slow rise in the level of detectable product might indicate lower levels of FROS and/or inflammation or disease in the body. This amount, rate of increase and/or subsequent decay in the time course experiment or test may be expressed mathematically as a differential function, tangential line, half-life, area-under-the-curve, etc.

According to embodiments of the present invention as introduced above, the detectable and/or diagnostic product may include an indigo-like compound that may be formed from two indoxyl, hydroxyl-indolyl or hemi-indigo intermediates due to cleavage of an indigogenic compound (e.g., 5-Iodo-Indolyl-3'-Iodo-4'-Hydroxy Ether compound) in the presence of FROS (see below). These indigo-like compounds may be visually colored and/or give off another detectable wavelength(s) of non-visual light. Detection of the light may be aided through the use of an appropriate device or instrument, especially for detection of non-visible or low intensity light. When a measurement of the amount of the detectable product in a sample is desired, other methods may be used to further concentrate, purify, isolate, etc., the detectable product, including the removal of hemoglobin and/or cells in the case of blood samples, or extraction or removal of cellular and/or extracellular material in the case of tissues. According to some embodiments, the visible color or other detectable wavelength of light from the indigo-like compound or hydroxyl-indolyl intermediate of the dehalogenation and cleavage reaction (i.e., the reactive indole heterocyclic compound—see below) may be created or enhanced by its further excitation, exposure or irradiation with light or other electromagnetic radiation, such as light having a particular wavelength(s). For example, an indigogenic compound lacking halogen substituents may form a classic indigo compound that is visually detectable due to its blue color. However, the hydroxyl-indolyl, indoxyl or hemi-indigo intermediate resulting from the dehalogenation and cleavage of the indigogenic compound lacking halogen substituents on the indolyl portion may be detected by fluorescence when irradiated with, or exposed to, UV light. By administering this indigogenic compound to the patient prior to surgery, a surgeon may be aided in localizing sites of FROS, which may indicate diseased tissues, during a surgical operation. Indeed, the fluorescence may be generally more detectable, sensitive and contrasting than visual detection of a colored compound. According to some embodiments, the indigo-like compound may also (or alternatively) be detected due to its absorbance, scattering, etc., of light or EM radiation, thus causing a reduction in the amount of transmitted light or EM radiation detected. For example, an indigo-like compound bonded to one or more halogen atoms, such as iodine, may appear to be radio-opaque when resident in intact tissues and irradiated with, or exposed to, X-rays or other EM radiation.

FIG. 28A provides an exemplary class of indogenic compounds (Formula 28) according to embodiments of the present invention which may be used for detection or diagnostic purposes. According to these embodiments, an indole heterocyclic portion of the compound (i.e., a hemi-indigo compound), containing variable substituents $R_1$, $R_2$, $R_3$, and $R_4$, may be linked by an ether linkage to a halogenated phenol ring as part of the compound of the present invention. X is a halogen in the ortho position relative to a hydroxyl group (—OH) on the phenol ring (i.e., X is a halogen that is bonded to a carbon that is adjacent to a carbon bonded to a hydroxyl group (—OH) on the phenol ring). The halogen X may be selected from either iodine (I) or bromine (Br), but generally may not include fluorine (F) or chlorine (Cl). According to these embodiments, the ether linkage (—O—) may be positioned on any of the remaining four carbons of the halogenated phenol ring that are not occupied by the ortho-positioned hydroxyl group (—OH) and halogen X. The identity of each of the substituents $R_1$, $R_2$, $R_3$, and $R_4$ of the indole heterocyclic compound (i.e., a hemi-indigo compound) may vary and may include, for example, a hydrogen, a hydroxyl, a sulfhydryl, an alkyl, a halogen, an amino, a nitro, etc. As described above, the identity of each of the other substituents present on the phenol ring may also vary. For example, substituents $R_5$, $R_6$ and $R_7$ on the phenol ring may include a hydrogen, a hydroxyl, a sulfhydryl, an alkyl, a halogen, an amino, a nitro, etc., groups. However, substituents $R_5$, $R_6$ and $R_7$ may each be hydrogen (see Formula 29 in FIG. 28B).

According to embodiments of the present invention in FIG. 28B, when a compound of Formula 29 comes in contact with an oxidizing agent or free radical, or is present in an oxidizing and/or free radical containing environment, the halogen X is cleaved and removed from the phenol ring and replaced with a hydroxyl group. This free radical attack or oxidation of the phenol ring further results in the breaking or cleavage of the ether linkage (—O—) between the indole heterocyclic portion (i.e., a hemi-indigo portion) and the phenol ring to release a reactive indole heterocyclic compound. In addition, a halide ($X^-$) and a benzenetriol-based or hydroxyhydroquinone-based compound (e.g., 1,2,4-benzenetriol) are formed. Two of the indole heterocyclic compounds formed during the dehalogenation and cleavage reaction may then react with each other in a subsequent reaction to form an indigo or indigo-like compound composed of the two indole heterocyclic compounds joined by a double bond. The indole heterocyclic compound products of the reaction have a strong preference for reacting with themselves to form the indigo or indigo-like compound. Following dehalogenation and cleavage, the hemi-indigo intermediate has a hydroxyl group formed on the carbon where the ether linkage was located. However, either before the intermediate reacts (with like intermediates) to form the indigo-like product or after forming the indigo-like product, this hydroxyl group formed by the reaction undergoes a keto-enol transition to form a keto group on that carbon (i.e., the third carbon).

According to these embodiments, the six-membered indole ring of the indigogenic compound may be designed to achieve different objectives or properties, such as to select for optimal characteristics or advantages based on color, X-ray profile and residence time (see below). The visible or light-interacting properties of the indigo-like compound may depend on the substituents bound to each of the indole rings. For example, the inclusion of halogens and other substituents in the indigogenic compound may affect the color of the indigo-like product of the reaction. Generally, the presence of halogens may give indigo-like compounds color properties that may be detected visually, but other substituents may also affect their color. As mentioned above, indigo-like compounds lacking halogen substituents may also be visualized or detected by exposing the tissue to UV light and detecting fluorescence.

According to some embodiments, an indogenic or non-indogenic compound that forms a detectable product(s) in the presence of FROS may potentially be used as part of a diagnostic test to determine the amount of systemic FROS load in the body of an individual (instead of or in addition to detection in a specific tissue). A sample may be taken from the body of the individual, such as a blood, sputum or a urine sample, and exposed or combined with the indogenic or non-indogenic compound to test for the amount of detectable product formed in vitro. The sample may optionally be processed to isolate or concentrate a portion or fraction of the sample prior to being combined with the compound to carry out the in vitro test. Alternatively, an indogenic or non-indogenic compound may be administered to an individual, and a sample, such as a blood, urine or tissue sample or biopsy) may then be taken from the individual (perhaps after a period of time) to test for the amount of detectable product in the sample. The sample may also be optionally processed to isolate, purify, extract or concentrate the indogenic or non-indogenic compound from the rest of the sample. According to these embodiments, the amount of product formed, as detected or measured by light measurement (e.g., absorbance, etc.), may be used to infer the amount of FROS present in a tissue or systemically in the body of the individual. As an alternative to indigo-like compounds, an in vitro test for detecting or measuring other products formed by the dehalogenation reaction, such as a quinone species, a phenolic species, or a halide (or iodo-tyrosine compounds that may be formed from iodo-thyronine compounds), may also be used following administration of an indogenic compound of the present invention.

In vitro detection methods based on the detection or measurement of indigo-like compounds or other detectable products (e.g., a benzenetriol-based product, a benzenetetrol-based product, or a halide) formed from starting compound or formula embodiments of the present invention by the dehalogenation reaction in the presence of FROS are proposed as a possible replacement for any current methods for detecting inflammation or FROS load in an individual, such as those based on the detection of C-reactive protein (CRP). For detection methods designed for measuring general inflammation or FROS load throughout the body of an individual, systemic samples, such as blood, sputum or urine, may be used. In addition, detection of products formed from the compound or formula embodiments of the present invention may also be used as a diagnostic indicator for progression against disease and/or levels of FROS exposure during treatment. As another example, diiodotyrosine (DIT) may be a detectable product formed in the presence of FROS during treatment with thyroxine.

Another feature of these indigo-like compounds of the present invention formed in the presence of the FROS is that they have a higher residence time in the tissue in which they are formed. With reference to FIG. 28, in comparison to the starting indigogenic compound having Formula 28 or 29, the indigo-like compound product of these reactions would have a much higher residence time in the tissue environment where it is formed because the indigo-like compound is more hydrophobic and lipophilic (and less soluble) compared to the original or starting indigogenic compound or precursor of Formula 28 or 29. The increased residence time of indigo-like products formed from the indogenic starting compounds of the present invention provides another useful feature to exploit for diagnosis and detection. In other words, the combination of its detectability and localization (at least transiently) to sites or tissues where it is formed provides the ability to detect specific sites or locations of FROS, which may be associated, for example, with particular sites of inflammation, infection or disease, such as cancer, etc.

According to some embodiments, when a compound of Formula 28 or 29 is converted into an indigo-like compound having higher residence time in a FROS-containing tissue as described above, the indigo-like compound (especially those with iodine) may be detected by radiological techniques, such as by being radio-opaque when analyzed by radiological, radiographic or X-ray imaging, such as a plain or projection radiograph. Furthermore, halogenated indigo-like compounds may also have a distinctly colored appearance, which may depend on the halogens and other substituents present on the indole heterocyclic rings, which may be detected by imaging or visualization, such as during surgery. For example, the detection or visualization of a colored or radiopaque portion of a tissue may be used to detect the location or site of infection or disease, such as cancerous tumor, etc., which may be used as part of a screen, test or diagnostic method, such as a mammography, etc. The combination of both colored and radiopaque characteristics of some indigo-like compounds of the present invention may be used together, for example, to coordinate procedures during surgery with pre- and/or post-operative radiological imaging of the surgical site. Therefore, one key advantage of some compounds of Formula 28 or 29 is that effective and targeted delivery of a colored indigo-like compound to a site of disease of inflammation in the body of an individual may be confirmed by separate X-ray or other radiological, imaging and/or visualization techniques. In addition, an indigo-like compound containing a radioisotope (see below) may be used to deliver the radioisotope to a target site with residence time for treatment of a diseased tissue, and the targeted delivery may then be separately confirmed by visualization and/or radiological detection or measurement. According to some embodiments, it is also envisioned that combinations of different indigogenic compounds may be co-administered to an individual, and their products from the dehalogenation reaction measured jointly, subsequently or in parallel by the same or different methods.

According to an exemplary embodiment, the at least transient deposition of a 5-iodo-indigo or 4,5-diiodo-indigo compound formed from the administration of 5-iodo-indolyl-3'-iodo-4'-hydroxy ether compound (see FIG. 29B) or the 4,5-diiodo analogue (see FIG. 29C), respectively, may be detected in situ where formed in the body of an individual by X-ray radiographic detection methods. A 4,5-diiodo-indolyl-3',5'-diiodo-4'-hydroxyl-p-phenol ether compound is also proposed as an example having an additional substitution on the phenol ring. These iodo-indigo-like compounds formed in high FROS-containing tissues may have a purple or grape color that may be difficult to visualize in situ by eye relative to surrounding tissues having similar coloration. However, since the iodo-indigo compounds deposited in the tissue are radio-opaque, X-ray doses and radiographic imaging may be used to detect their at least transient formation in FROS-containing tissues, perhaps by comparison to control tissues (See, e.g., Example 6 below).

Potentially, detection or measurement of the iodo-indigo compound formed may also be done in vitro by light measurement (e.g., absorbance, etc.) by taking a sample, such as a urine, blood, sputum, or tissue sample or biopsy, and measuring the amount of iodo-indigo compounds contained therein. For example, both the mono-iodo indigo-like product and the di-iodo indigo-like product may be detected by light absorbance in a wavelength range from about 300 nm to about 310 nm. Such in vitro measurement may be done after further processing to extract, purify or isolate iodo-indigo compounds from the rest of the sample and would avoid the issue of having similar coloration as intact tissue.

Although the 4,5-diiodo analogue above would produce an indigo-like compound that is more radio-opaque than the 5-iodo indigo-like product (due to the additional iodine), the presence of the additional iodines on the 4,5-diiodo-indigo-like product may also lead to higher residence time, and such higher residence time may be less tolerable for safety reasons and/or may interfere with subsequent or follow up tests and measurements. Thus, with any indigogenic compound described herein, the type and number of halogens on the indigo-like product of the reaction must be chosen to balance between (i) the strength of signal, coloration or radio-opaqueness of the indigo-like product and (ii) the amount of residence time of the indigo-like product in a tissue.

According to another exemplary embodiment, 5-Br-4-Cl-Indolyl-3'-Iodo-4'-Hydroxy Ether compound (see FIG. 29A) may be taken or administered orally or intra-venously followed by an optional time for in vivo color development in the body or tissue. As described generally above, the localization of the 5-Br-4-Cl indigo-like compound product may then be visualized in situ in the tissue where formed, such as during surgery. The 5-Br-4-Cl indigo-like compound may have a visible color (e.g., aquamarine) that is distinguishably visible from surrounding tissues and may thus be used to label diseased tissues (e.g., tumors, etc.). Thus, their site of formation and deposition may be determined visually, such as during surgery, as an indication or labeling of tissues in situ of these diseased tissues having high FROS. Alternatively or additionally, the 5-Br-4-Cl indigo-like compound may also be detected or measured in vitro by light measurement (e.g., absorbance, etc.) by taking a sample, such as a urine, blood or tissue sample or biopsy, and measuring the amount of 5-Br-4-Cl indigo-like compounds therein as described above, which may be done after further processing to extract, purify or isolate the 5-Br-4-Cl indigo-like compounds from the rest of the sample. For example, detection or measurement may be performed by measuring the light absorbance of the 5-Br-4-Cl indigo-like compound at a wavelength within a range from about 595 nm to about 605 nm.

According to another set of embodiments, molecules produced by the FROS-mediated reactions described herein may be differentially detected or measured by other methods, such as mass spectrometry (MS), nuclear magnetic resonance (NMR) spectroscopy, magnetic resonance imaging (MRI), chemical test, etc., (perhaps in combination with phase separation, chromatography, and/or other method of separation or purification) to quantitate and/or locate their presence and/or site of formation in the body for diagnostic purposes. Some products of the reaction from compound embodiments the present invention may be distinguished by their appearance with MRI and/or by size or characteristics of peaks displayed by NMR spectroscopy. For NMR spectroscopy, the presence or amount of a product in a blood, urine or tissue sample taken from an individual may be determined.

Compound embodiments of the present invention, such as those represented in FIGS. 1-25, 28 and 29, may further include those compounds containing the carbon-13 isotope ($^{13}C$) in place of carbon-12 ($^{12}C$), which may be differentially detected or measured by NMR or MRI. In particular, the benzene or phenol rings of these compounds containing $^{13}C$ as one or more of the carbons of the ring may be differentially detected or measured by these methods. In addition, compounds containing $^{13}C$ may be differentially detected or measured by mass spectrometry (MS) techniques. Because $^{13}$C is a stable isotope, the isotope itself does not pose a health risk to the individual taking it. Thus, products of the reaction containing $^{13}$C, including benzenetriol-based products or benzenetetrol-based products, may be detected or measured by these methods.

According to some of these embodiments, any of the indigogenic compounds in FIGS. 25 and 26 (e.g., according to Formula 25 or 26) may have $^{13}$C as one or more of the carbons of the six-membered ring of the indole heterocyclic portion or hemi-indigo portion of the indigogenic compound. As discussed above, when the indigogenic compound is present in a high FROS-containing tissue or environment within the body of an individual, it undergoes a dehalogenation and cleavage reaction to liberate $^{13}$C-containing indole heterocyclic compound products having a strong preference for reacting with themselves to form the indigo or indigo-like compounds containing the $^{13}$C in the resident tissue or environment. Once the indigo or indigo-like compounds are formed, they will remain in the tissue where formed with a prolonged residence time as described herein. These indigo or indigo-like compounds may then be differentially detected in situ by MRI of the individual due to the presence of $^{13}$C in the six-membered indole ring. The MRI may be conducted such that only a small area, volume or region of the body is imaged, or alternatively such that the whole body of the individual is imaged. Such imaging may be done in connection with imaging of a known site of disease or to search for sites of high FROS or inflammation that may be indicative of sites of disease, such as cancer.

According to another broad aspect of the invention, a compound according to some embodiments may provide targeted delivery of a radioactive or rare stable isotope-containing compound to diseased cells and/or tissue (e.g., cancerous cells or tissues, etc.) to cause diseased cells of the targeted tissue to die, undergo apoptosis, favorably senesce, stop dividing, differentiate, etc., which may be favorable for the treatment of the disease. According to these embodiments, a halogenated phenol ring compound may be bonded to one or more radioactive isotopes, such as radioactive iodine (e.g., $^{125}$I, $^{131}$I). A key factor for the effective delivery of a radioactive isotope-containing compound to a targeted tissue or cells (e.g., cancerous or diseased cells or tissues) is avoiding as much as possible unwanted accumulation of the radioactive compound in other normal tissues and cells, while achieving sufficient residence time in one or more targeted tissues (e.g., cancerous or diseased cells or tissues) to exert the desired effect.

According to embodiments of the present invention, compounds having these balanced properties may include radioactive isotope-containing indigogenic compounds that dissolve in an aqueous solution, but which form radioactive compounds with high residence time in a targeted tissue following dehalogenation and ether or thioether cleavage in a reaction triggered by oxidizing agents and/or free radicals present in the targeted cells or tissue. In other words, much like the drug-linked halogenated phenol ether (or thioether) compounds described above, the radioactive isotope-containing halogenated phenol ether (or thioether) compounds of the present invention may behave like a pro-drug. Once the radioactive isotope-containing halogenated phenol ether (or thioether) compounds encounter an oxidizing and/or free radical containing environment, the halogenated phenol ether (or thioether) compound may become cleaved as a result of a dehalogenation reaction to produce a relatively insoluble radioactive isotope-containing product with relatively high residence time in the target tissue or cells in which it is formed. Generally speaking, a compound may have a higher residence time in a targeted tissue if it is more hydrophobic or lipophilic.

Therefore, according to some embodiments of the present invention, a radioactive compound may be designed such that the solubility of the radioactive compound becomes altered in a targeted tissue as a result of the dehalogenation and cleavage reaction triggered by oxidative agents and/or free radicals present in the targeted tissue. According to some of these embodiments, a radioactive compound may be designed such that a radioactive compound is converted in the targeted tissue as a result of the dehalogenation and cleavage reaction from being a hydrophilic compound dissolved in an aqueous solution to a relatively hydrophobic or lipophilic compound with increased residence time in the targeted tissue. It is further possible that the residence time of a product of a given compound may be engineered depending on the number and/or types of substituents present on the radioactive isotope-containing compound. As described above, the present invention further encompasses compositions comprising radioactive compounds of the present invention as well as any suitable method of treating, administering to, etc., an individual with these compositions comprising radioactive compounds of the present invention, perhaps in combination with a pharmaceutically acceptable carrier, to an individual or patient.

According to embodiments presented in FIG. 25, the compound of Formula 25 or 26 may be used to deliver a radioactive isotope present on the indigogenic compound. The indigo-like compound product formed by the dehalogenation reaction will retain the radioactive isotope and have a higher residence time (at least transiently) in the targeted tissue where it is formed to deliver focused treatment of the radioactive isotope to the site of its formation. In contrast, the indigogenic precursor compound would be relatively soluble and would tend to circulate throughout the body until being expelled or excreted from the body. According to these embodiments, one or more of variable substituents $R_1$, $R_2$, $R_3$, and $R_4$ of the indole heterocyclic compound (i.e., a hemi-indigo compound) in FIG. 19 may include a radioactive isotope, such as a radioactive halogen (e.g., $^{131}$I or $^{125}$I), which provides the therapeutic dose of radioactivity for the targeted (i.e., diseased) tissue.

EXAMPLES

Example 1

Synthesis of 1-Acetyl-4-Iodo-Indoxyl

N-Acetyl-3-Iodo-2-Methyl Aniline. Charge a 5 L, 3 neck flask equipped with a mantle, stirrer, condenser, with 708 grams (5M) 3-Iodo-2-Methyl Aniline, followed by 700 ml glacial acetic acid. Add in a stream of 520 grams (5.1M) acetic anhydride and allow the solution to come to a gentle reflux for an hour. The solution is allowed to cool and poured in a stream in a large container of 8 L ice water. The product will crystallize immediately and is filtered and squeezed under vacuum and air-dried. Yield was 900 grams (Theoretical yield=918 g).

N-Acetyl-6-Iodo Anthranilic Acid. Charge a 22 L flask equipped with a stirrer, thermometer, condenser and heating mantle with 616 grams Magnesium Sulphate (heptahydrate) followed by 10 L water, and 800 grams N-Acetyl-3-Iodo-2-Methyl-Aniline The mixture is stirred and heated to 85° C., over about an hour, and heat is stopped. Potassium Permanganate (1200 grams, 8 mol) is added in portions over about 2 hours while the temperature rises to 95° C. from the exotherm. After all the KMnO$_4$ is added, the reaction is stirred for 1 hour with the temperature between 80° C. to 90° C. If excess purple permanganate is present, add 20 to 50 cc of Methanol to quench. The mixture is filtered while still not through a large Buchner funnel, and the MnO$_2$ "cake" is washed with hot water. The clear filtrates are cooled to about 20° C., and the acidity is adjusted to pH=1 (paper) with 20% H$_2$SO$_4$. The precipitated product is isolated by filtration and dried. Yield was 623 grams (66%) (Theoretical yield=924 grams). Melting point (m.p.) at 202-205° C.

6-Iodo Anthranilic Acid Hydrochloride. Charge a 12 L, 3-neck flask, equipped with a stirrer, condenser, heating mantle and thermometer with N-Acetyl-6-Iodo-Anthranilic acid (400 grams) and 2.5 L concentrated HCl. Adjust the temperature to 50-55° C. and maintain for 24 hours. Higher temperatures may decompose the product. Chill the reaction to less than 5° C. in an ice bath, filter the product, wash the filter "cake" with acetone, then diethylether. Air dry the product. Yield was 340 grams. (Theoretical yield=374.4 grams). Melting point (m.p.) at 176-180° C.

N-(3-Iodo-2-Carboxy Phenyl) Glycine-Potassium Salt. Charge a 5 L, 3 neck flask, equipped with a stirrer, thermometer and heating mantle, with 6-Iodo-Anthranilic acid HCl (416 grams, 0.2 mol), followed by 1 L water and 248 grams (4 mol) KOH in 250 cc water, to result in a solution with pH=8 to 9. Adjust if necessary. Add sodium chloroacetate (250 grams, 2.1 mol) and stir the reaction for 18 hours at 50-60° C. Cool the reaction to 18 to 20° C., filter off the product, and wash with acetone. Air dry the product. The filtrates will yield about 20 grams second crop. Yield was 368 grams (67%). (Theoretical yield=556 gm).

3-Iodo-Indoxyl Diacetate. Charge a 5 L, 3 neck flask equipped with a heating mantle, stirrer and condenser with N-(3-Iodo-2-Carboxy Phenyl) Glycine (250 grams, 0.8 mol), fused Sodium Acetate (200 grams) and 1.5 L acetic anhydride. Heat the mixture to gentle reflux until CO$_2$ evolution stops. The hot, dark solution is poured into a beaker and cooled in an ice bath to 18-22° C. to crystallize the product. Filtrates can be concentrated in vacuo to remove most the acetic anhydride, then precipitated by the addition of ice (temperature less than 70° C.) to yield a second crop. Filter, wash with water, and dry. Re-crystallize from hot acetone (about 1 gram/10 cc) or hot ethyl acetate (about 1 gram/10 cc). Yield was 165-180 grams of well-formed crystals. Melting point (m.p.) at 150-152° C. Shows 1 spot on TLC in CH$_2$Cl$_2$: MeOH (95:5).

4-Iodo-N-Acetyl Indoxyl. Equip a 2 L beaker with a large magnetic stirrer in an ice bath. Add in 600 cc of 90% H$_2$SO$_4$ (535 cc H$_2$SO$_4$ into 65 cc H$_2$O) and cool to 20° C. Add the 3-Iodo-Indoxyl Diacetate (128 grams, 0.39 mol) in portions over 20 minutes, with good mixing, keeping temperature less than 28° C. Stir the resulting solution for an additional 60 minutes at 18 to 22° C., and pour in a stream into 2 L of ice and water mix, with good mixing. The settled product is filtered, washed with ice water, and the filter "cake" is mixed with 1 L CHCl$_3$. The aqueous phase is separated, and the organic phase concentrated to a solid in vacuo. The product is slurried with 0.6 L n-Hexane, filtered, washed with minimal n-Hexane and dried. Yield was 104 gm (88%). (Theoretical yield=121.6 grams). Melting point (m.p.) at 166° C.

Example 1A

Synthesis of 1-Acetyl-4,5-Diiodo-Indoxyl

N-(3-Iodo-2-Carboxy-Phenyl) Glycine. Potassium Salt of Example 1 was iodinated in the 4-position by suspension (35.7 grams, 0.1 mol) in 150 ml 1.0 N HCl and cooled to about 20° C. A second solution of 100 ml 1.0 N HCl containing ICl (20 grams, 0.125 mol) was added to the suspension with stirring and reacted for 6 hours at about 20 C. The settled product was collected by filtration and re-crystallized from ethanol/water to yield 28.2 gram (84%), m.p. 182-186 C. The Diiodo indoxyl product is produced in the subsequent steps described in Example 1, starting with ring closure and acetylation in acetic anhydride.

Example 2

Synthesis of 1-Acetyl-5-Br-4-Cl-Indoxyl

1-Acetyl-5-Br-4-O-Indoxyl was synthesized according to the methods described in Example 1 above for 5-Iodo-Indoxyl, by utilizing 2-Methyl-3-Chloro-Aniline as the starting material and including a bromination step. Specifically, the resulting N-(3-Chloro-2-Carboxy-Phenyl) Glycine (267.6 grams, 1.0 mol) is brominated by mixing with 550 cc glacial acetic acid, followed by addition of 52 cc of liquid Bromine to the vigorously stirred suspension. Bromination is exothermic and results in complete solution followed by precipitation of the product during the last 10 cc of Bromine addition. The reaction was diluted with 2 L of ice water and the brominated product was isolated by filtration and air dried to yield about 240 grams. Melting Point (m.p.) 176-178 C. The remaining procedures described in Example 1 result in the desired 1-Acetyl-5-Br-4-Cl-Indoxyl.

Other syntheses of ring substituted indoxyl and indigo compounds are described, for example, in Holt, S. J., "General Cytochemical Methods" J. F. Danielli, Ed., Academic Press, New York, N.Y., p. 375 (1958), the entire contents and disclosure of which are incorporated herein by reference, wherein the 4,5,6 indoxyl positions can be substituted, individually and in combination, and are anticipated as Br, Cl, and I. These compounds may have advantages of solubility, tissue distribution, residence time, lower toxicity, ease of synthesis and quality of the indigo precipitate for the intended purpose as described in the present invention.

Example 3

Synthesis of 1-Oxaspiro-3,5-Diiodo-Bicyclooctadiene-6-One

This synthesis was adapted and extended from prior works. See, e.g., Salamonczyk, G. M. et al., *Tetrahedron Letters*, 38(40): 6965-6968 (1997), the entire contents and disclosure of which are incorporated by reference.

P-hydroxy benzaldehyde was diiodinated, followed by reduction of the aldehyde to the benzyl alcohol product. The alcohol was oxidized to the epoxy and purified to yellow orange crystals by removal of hydrophilic components by silica gel chromatography:

A solution of p-hydroxybenzaldehyde (31.0 grams, 0.25 mol) was prepared in 450 ml 20% HCl by heating to 75° C. in a stirred reaction vessel. A second iodinating solution was prepared by dissolving 81.25 grams ICl to 125 ml 20% HCl. This solution was added to the first solution over about 5 minutes (no exotherm). The reaction temperature was raised to 55° C. for about 90 minutes as the reaction becomes clear and yellow. The reaction was poured into 4 L of ice-cold water and allowed to precipitate overnight. The product was isolated by filtration, washed with water, dried down in vacuuo with rubber dam (50° C.). Yield was 79.1 grams of off-white powder (85% of theoretical yield). The diiodo product can be purified by dissolving as a 10% solution in hot ethanol and precipitation by addition of hot water and cooling on ice with stirring. Melting Point (M.P).: at 201-203° C. A second crop containing monoiodinated product can be obtained by adding cold water and storage at 4° C.

The benzyl alcohol product was formed by reaction of a solution of 3,5-Diiodo-4-Hydroxy-Benzaldehyde (49.6 grams, 0.133 mol) in 0.665 L isopropanol. Sodium borohydride (8 grams) was added with stirring, and the reaction was warmed to 82° C. over about 10 minutes to become homogeneous. The entire reaction was treated with 3 N HCl (58 ml) to pH=5. The precipitate was not removed. Water was added all at once at ambient temperature with stirring. The boric acid will dissolve, and the desired benzyl alcohol product will form over about 10 minutes. The reaction was cooled on ice to less than 15° C. to fully precipitate and isolate the product by filtration, which was then washed with minimal cold water. The filter cake was dried in vacuo at 50° C. Yield was 40 grams of off-white crystals. Melting Point (M.P.) at 139-140° C.

The epoxide function was formed from the alcohol (16 grams, 0.425 mol) by dissolving in a mixture of ethyl acetate (128 ml), acetic acid (102 ml) and water (13 ml) and treating with sodium bismuthate (23.9 grams, 0.085 mol) at 36° C. for 4 hours. The boric acid precipitate was filtered off, and 200 ml of toluene was added to the filtrate. The phases were separated, and the organic phase was dried with anhydrous sodium sulfate. The organic phase was filtered through anhydrous silica, and the filtrate was dried down to form the crystalline diiodo-epoxy product. Yield 8.9 gm (42% of theoretical yield) containing less than 8% of the mono-iodo substituted epoxy product.

Example 4

Synthesis of 5-Iodo-Indolyl-3',5'-Diiodo-4'-hydroxyl-p-Phenol Ether

A suspension of 3-Hydroxy-5-Iodo-Indole Acetate (8.30 grams, 0.02 mol) was prepared in was prepared as a suspension in 1 L of 50 mM sodium borate buffer, pH=8.0. The Diiodo Epoxy reagent from Example 3 (8.25 grams, 0.022 mol) was added as a solution in 200 ml of DMF, the cloudy suspension was reacted with stirring for 18 hours at about 20 C, and the precipitated product allowed to settle. The supernatant solution was decanted, and the product collected by filtration and washed with acetone prior to drying in vacuo. The final product (12.3 grams) was deacetylated in 123 ml anhydrous methanol containing 20 mg sodium methoxide. The solution will clarify followed by precipitation of the final product (11.6 grams, 0.016 mol) at 81% yield based on the diiodo-indole.

Example 4A

Synthesis of 4,5-Diiodo-Indolyl-3',5'-Diiodo-4'-Hydroxy-p-Phenyl Ether

This product was produced as in Example 4 except that the Diiodo Indoxyl of Example 1A is utilized. All remaining steps are the same with a yield of 12.4 grams (85%).

Example 5

Synthesis of 5-Bromo-4-Chloro-3',5'-Diiodo-4'-Hydroxy-p-Phenol Ether

The diiodo epoxy reagent of Example 3 was reacted with the product of Example 2,5-Br-4-Cl-Indolyl Acetate (8.24 g, 0.02 mol), and as described in Example 4. The final product was formed by deacetylation in 123 ml of anhydrous methanol containing 20 mg of sodium methoxide.

Example 6

X-Ray Detection of Mouse Tumors with Iodo-Indigo Compound

As described above, oxidative foci or tumors may be identified by X-ray radiographic imaging of animals following administration of an indigogenic compound of the present invention. The radio-opaque indigo-like product formed and deposited with residence time in FROS-containing tumor tissues may then be detected.

Figure 30:
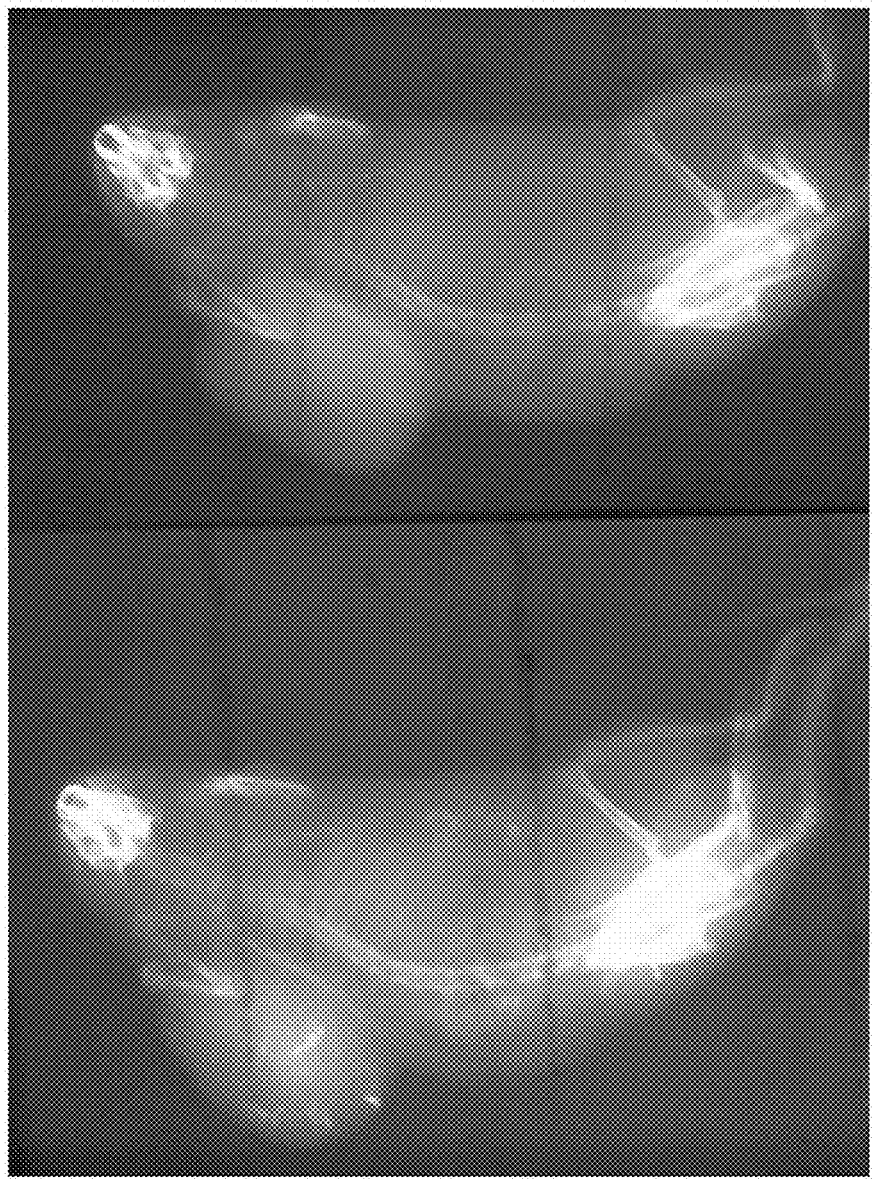
FIG. 30 is a pair of images showing radio-opaque sites of formation of an indigo-like product with an administered indigogenic compound, which are absent prior to administration of the indigogenic compound.

In this example, female C3H/HeN mice were obtained as multiparous retired breeders (i.e., after 3 to 4 litters) that were positive for a mammary tumor virus. See, e.g., Sellitti, D. F., Tseng, Y-C., and Latham, K. R., "Effect of 3,5,3'-Triiodo-L-thyronine on the Incidence and Growth Kinetics of Spontaneous Mammary Tumors in C3H/HeN Mice," *Cancer Research*, 41: 5015-19 (1981), the entire contents and disclosure of which are incorporated herein by reference. Mice showing spontaneous tumors were given 10 mg of 5-Iodo-Indoxyl-3',5'-Diiodo-4'-hydroxy ether substrate (product of Example 4) by gavage. These mice were then subjected to X-ray imaging of the tumors about two hours after being fed the iodo-indigogenic compound. Mice that were treated with the iodo-indigogenic compound showed radio-opaque tumor regions or foci by X-ray demonstrating that the 5,5'-diiodo-indigo-like product was formed and deposited in the oxidative tumor tissues (See FIG. 30, bottom panel). In contrast, control X-ray images of the same mice prior to treatment did not show these foci (See FIG. 30, top panel). When developed, the X-ray film appears dark in areas where more transmission occurs and light in areas where less transmission occurs.

As a result of handling the animals and keeping them in cages, some of the mice that were administered the 5-iodo-indigo compound experienced various small injuries or wounds (e.g., cuts, scratches, etc.). When some of these animals were subjected to X-ray imaging, a strong detection was observed at the sites of the wound or injury (data not shown). Without being bound by any theory, it is believed that a local infection and/or wound healing mechanisms were responsible for high FROS at these sites that led to local production of high levels of the detectable radio-opaque indigo-like product.

Example 7

Administering 5-Br-4-Cl-Indolyl-3'-Iodo-4'-Hydroxy Ether for Color Detection

According to one embodiment, patients may be given an amount of 5-Br-4-Cl-Indolyl-3',5'-Diiodo-4'-Hydroxy-Ether (e.g., about 200 mg) orally or intra-venously followed by an optimal time for in vivo color development in the body or tissue (e.g., for about two hours). The formation of 5,5'-Dibromo-4,4'-Dichloro indigo in tissue locations may be observed macroscopically and used as a diagnostic indicator for further treatment (eg. Surgical removal). Alternatively, urine, blood or other tissue biopsy or samples may then be taken from the patient for absorption or optical density (OD) or other analytical measurement of the 5-Br-4-Cl Indigo compound formed. Extraction of the indigo-like compound from the tissue or urine sample with chloroform or other solvent or assay may be used to minimize, reduce or eliminate substances that may compete or alter indigo detection and quantification.

Example 8

Synthesis of 3-Hydroxy-3',5'-Diiodo-Thyronimine

The general synthesis scheme includes the formation of the ring ether link under basic conditions followed by reaction with nitromethane at the aldehyde. The ring nitro group is then reduced to the amine, diazotized and converted to the hydroxyl product by boiling in water. Reaction with hydroquinone instead of p-methoxyphenol eliminates need for subsequent de-blocking, but results in slightly lower product yield. The product is reduced to yield the amine, and iodination yields the final product:

P-hydroxy phenol (100 g, 0.81 mol) was reacted under reflux for 1.5 hours with 3-Nitro-4-Chloro-Benzaldehyde (100 g, 0.54 mol) in 1.1 L water containing 41.5 g potassium carbonate and 5.35 g sodium bisulphate. The reaction mix was poured into 8 L of water with rapid stirring and allowed to precipitate for 18 hours. The precipitate was isolated by filtration and dissolved in 500 ml hot ethanol, then cooled to obtain 66 grams of a yellow, microcrystalline precipitate (66 grams) in about 45% yield that is isolated by filtration and washing with n-propanol. This vacuum-dried product was suitable for the next step and was stored under dry argon to protect the aldehyde from oxidation.

Nitromethane (32 gm, 28.2 ml, 0.52 mol) and the aldehyde (136.55 g, 0.5 mol) were suspended in 1.0 L ethanol in a 5 L reaction vessel with stirring and cooled to less than 10° C. The reaction was initiated by the slow addition of a solution containing 50 ml water, 35 g potassium hydroxide and 100 ml methanol while maintaining the reaction temperature to less than 10° C. A thick precipitate was formed after an additional 15 minutes of reaction, and the product was fully precipitated by the addition of 2.5 L isopropyl alcohol. The potassium salt precipitate was isolated by filtration, and the filter cake was washed with 2 floods of isopropyl alcohol prior to drying in vacuum oven at 50 C to yield 160 gm (86%) of product, suitable for ring nitro group reduction.

The potassium salt (44.6 gm, 0.12 mol) was suspended in 250 ml methanol, and a solution containing 110 ml water, 18 gm NaHS (monohydrate) and 150 ml methanol was prepared in a separate container. This solution was added with mixing to the solution of the potassium salt and reacted under reflux for about 60 minutes. Cool the reaction to less than 20° C., and 1.2 L ice cold 0.5 N sulfuric acid was added with mixing. The settled precipitate was isolated by filtration and washed with cold water and rubber dam. The product was dried in vacuo at 50° C. Yield was about 35 grams (75% theory) of a yellow amorphous powder suitable for diazotization. The side chain amide was protected from diazotization.

The amine (23.0 gm, 0.06 mol) was suspended in 140 ml concentrated sulfuric acid, with cooling and temperature monitoring and cooled to less than 10° C. A solution of sodium nitrite (4.14 gm, 0.06 mol) was prepared in 60 ml concentrated sulfuric acid and cooled to less than 10° C. This solution was added to the amine solution with adequate stirring while maintaining the reaction at less than 10° C. The reaction proceeded for 18 hours and then the exothermic reaction was warmed to 110° C. with nitrogen evolution to convert the diazo function to the hydroxy. The reaction was poured into 880 grams of ice with good stirring, diluted with 3 L cold water, and the precipitated product was allowed to settle. The supernatant was decanted, and the product was isolated by filtration and washed with cold water. Yield was 12.5 grams (73% theory).

The side-chain amide was further reduced to the primary amine with RedAl prior to iodination to from the final product as the HCl salt. Diiodination of the 3,4'-Dihydroxy product occurred by suspending the di-hydroxy compound (31 grams) in 350 ml of 20% HCl. A second solution containing 125 ml of 20% HCl and 81.25 grams ICl was added in a steady stream (no exotherm). Mono-Iodination with 42.0 gm ICL was used and was added over 1 hour. at 4° C., followed by heating to 55° C. The Diiodo reaction turned yellow over about 1.5 hours at 55° C. The reaction was poured into a 5 L vessel, and 3 L of water was added with active mixing. Precipitation was performed with continued stirring for 12 hours, and the product was isolated by filtration. The filter cake was washed with water. The dioxane purified product was dried in vacuuo at 50° C. Yield was 52 grams (89% of theoretical yield) of a sl. off-white product. MP 231-236 dec. HNMR (AcetoneD6. 270 MHz): 2.63-2.65 (m, 2H, CH2), 2.91-2.98 (m, 2H, CH2NH2), 3.61 (contam. Dioxane), 3.81 (m, 4H, OH, OH, NH2) 6.10 (m, 1H, pos 3 aromatic, 6.71-6.76 (m, 2H, pos. 2,6 aromatic), 7.44-7.46 (2H, pos 2',6' aromatic). CHNI: carbon (C) (34.02 found, 33.81 theory); hydrogen (H) (3.45 found, 2.60 theory); nitrogen (N) (2.79 found, 2.80 theory); and iodine (I) (50.26 found, 51.11 theory).

Example 9

Synthesis of 3,5-diiodo-4-hydroxy-(N-Acetyl Tryptamine)

Serotonin was treated with acetic anhydride by standard methods, and the N-Acetyl Tryptamine (20.30 gm, 0.1 mol) was suspended in 1 L of 50 mM sodium borate buffer, pH=8.0. The Diiodo Epoxy reagent of Example 3 (37.5 grams, 0.1 mol) was added as a solution in 200 ml of DMF, the cloudy solution was reacted with stirring for 18 hours, and the precipitated product was allowed to settle. The supernatant solution was decanted, and the product was collected by filtration and washed with acetone prior to drying in vacuo. The product (46.0 grams) was de-acetylated in 240 ml anhydrous methanol containing 50 mg sodium methoxide. The solution was allowed to clarify, and was followed by precipitation of the final product (41.6 grams, 0.072 mol) at 72% yield based on the N-Acetyl Tryptamine.

Example 10

Synthesis of 3,3'-Diiodo-4-4'-Dihydroxy-Diphenyl Ether

Di-hydroxy-di-phenyl ether (50.25 gm, 0.28 mol) was dinitrated at the 3,3' positions by suspending in 342 ml of water with cooling, while treating slowly with 265 gm of concentrated nitric acid. After all of the nitric acid was added, the solution became homogeneous. The reaction was exothermic and was kept at less than 25° C. while the nitration product precipitates over about 5 hours. The crystals were collected by filtration and dissolved in minimal hot water, and the solution was adjusted to pH=6 with aqueous ammonia. Crystals of the dinitro product were immediately precipitated for isolation by filtration. A further crystallization from water with carbon decolorization was done to provide a product suited to reduction: 146 gm (0.5 mol) of this product was dissolved in 1.5 L methanol and reduced under pressure with 8.0 gm of Paladium/Charcoal. When completed, the filtrate was evaporated in vacuo at less than 30° C. The residue was purified from hot ethanol to yield about 43 grams of product. This product (40 grams) was dissolved in 80 ml acetic acid and added slowly to 40 ml concentrated sulfuric acid with stirring, keeping the temperature below 20° C. This solution was added carefully over several hours at about 0° C. to a solution containing 125 ml concentrated sulfuric acid and 17.5 gm of sodium nitrite. The reaction was continued for another hour at 0° C. A second solution was prepared by adding sodium iodide (80 gm), iodine (67 gm), urea (10 gm) in 1300 ml water, and covered with 250 ml of chloroform and the amine solution was added slowly. The temperature rose as the reaction continued. After about an hour, the chloroform layer was saved, and the aqueous layer was extracted 2 more times with 200 ml of chloroform. The combined organic portion was extracted with water and the dried under vacuum in a 40 C water bath. The final product was purified from hot ethanol. Yield was 58 grams.

Example 11

4'-Hydroxy-3'-Iodo-6-Mercaptopurine Ether

The 6-thio-ether linked compound was formed by dissolving 6-Mercaptoguanine, monohydrate (20.4 gm, 0.12 mol) and 2-Nitro-4-Br-Phenol (26.16 gm, 0.12 mol) in acetone (200 ml) at about 20 C. A solution of KOH (2 N, 60 ml) was slowly added (4 hr) to the well mixed reaction. The KBr precipitate was removed by filtration and the acetone filtrate containing the thio-ether product is reduced in volume under vacuum until a product precipitate forms. The slurry was placed on ice to fully precipitate and the product was isolated by filtration and washed with minimal cold acetone and compressed with a rubber dam. The nitro group is reduced to the amine using 12 gm of product dissolved in 150 ml anhydrous methanol/25 mg NaOMe, as described in Example 3. The precipitated product is isolated by filtration and the amine is diazotized by dissolution (10 gm) in 100 ml concentrated sulfuric acid and cooled to about 5 C (solution 1). Sodium nitrite (gm) is dissolved in 50 ml concentrated sulfuric acid, cooled to 5 C (solution 2) and added with stirring to solution 1, with cooling, at a rate that keeps the reaction temperature at about 5 C but less than 10 C. The resulting diazo compound was converted to the iodo product by reaction in 20% HCl containing ICl as described in Example 3.

Example 12

Synthesis of 3,5-Diiodo-4-Hydroxy-1,3'-Ether-Cortisone

Cortisone (+) 7.2 grams, 0.02 mol, was dissolved in 0.5 L sodium borate buffer (0.2 M, pH 8), and the Diiodo Epoxy reagent of Example 3 was added (14.96 grams, 0.04 mol) as a solution in 200 ml of ethanol. After 4 hours of reaction, the precipitated product was isolated by filtration, washed with acetone and dried in vacuo to yield about 6.2 gm of white microcrystalline product.

While the present invention has been disclosed with reference to certain embodiments, it will be apparent that modifications and variations are possible without departing from the spirit and scope of the invention as defined in the appended claims. Furthermore, it should be appreciated that all examples in the present disclosure, while illustrating embodiments of the invention, are provided as non-limiting examples and are, therefore, not to be taken as limiting the various aspects so illustrated. The present invention is intended to have the full scope defined by the language of the following claims, and equivalents thereof. Accordingly, the drawings and detailed description are to be regarded as illustrative and not as restrictive.

What is claimed is:

1. A composition comprising a compound having the following chemical structure:

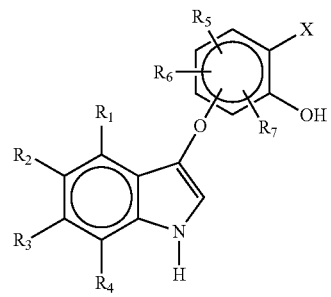

wherein $R_1$, $R_2$, $R_3$, $R_4$, $R_5$, $R_6$ and $R_7$ are each a hydrogen, a hydroxyl, a sulfhydryl, an alkyl, a halogen, an amino, or a nitro group, and wherein X is a halogen.

2. The composition of claim 1, wherein X is iodine or bromine.

3. The composition of claim 1, wherein $R_3$ and $R_4$ are each a hydrogen.

4. The composition of claim 1, wherein $R_2$ is a halogen.

5. The composition of claim 4, wherein $R_2$ is iodine.

6. The composition of claim 4, wherein $R_1$ and $R_2$ are each a halogen.

7. The composition of claim 6, wherein $R_1$ and $R_2$ are each an iodine.

8. The composition of claim 6, wherein $R_1$ is chlorine and $R_2$ is bromine.

9. The composition of claim 1, wherein $R_5$, $R_6$ and $R_7$ are each a hydrogen.

10. The composition of claim 9, wherein $R_2$ is a halogen.

11. The composition of claim 10, wherein $R_2$ is iodine.

12. The composition of claim 9, wherein $R_1$ and $R_2$ are each a halogen.

13. The composition of claim 12, wherein $R_1$ and $R_2$ are each an iodine.

14. The composition of claim 12, wherein $R_1$ is chlorine and $R_2$ is bromine.

15. The composition of claim 12, wherein $R_3$ and $R_4$ are each a hydrogen.

16. The composition of claim 1, wherein the compound has the following chemical structure:

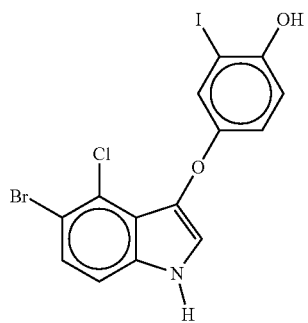

17. The composition of claim 1, wherein the compound has the following chemical structure:

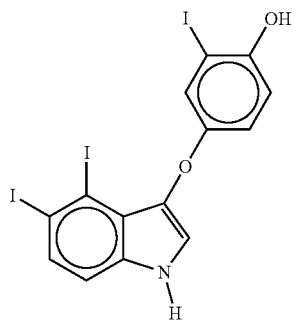

18. The composition of claim 1, wherein the compound has the following chemical structure:

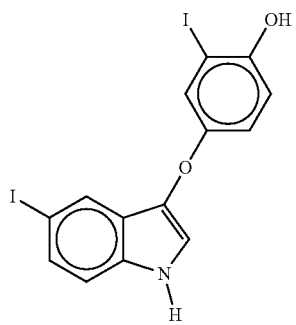

19. The composition of claim 1, wherein one or more of $R_1$, $R_2$, $R_3$ and $R_4$ contains a radioactive isotope.

20. The composition of claim 19, wherein one or more of $R_1$, $R_2$, $R_3$ and $R_4$ is a radioactive isotope.

21. The composition of claim 20, wherein one or more of $R_1$, $R_2$, $R_3$ and $R_4$ is $^{125}I$ or $^{131}I$.

22. The composition of claim 1, wherein the composition is a pharmaceutical composition further comprising a pharmaceutically acceptable carrier.

23. The composition of claim 1, wherein one or more of the carbons of the six-membered indole ring of the compound is carbon-13 ($^{13}C$).

24. A method comprising:
(a) administering to an individual having cancer a composition comprising a compound having the following chemical structure:

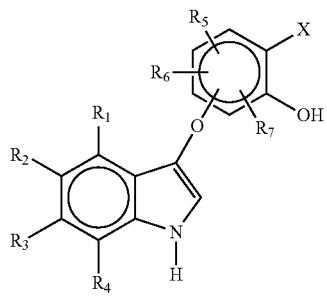

wherein $R_1$, $R_2$, $R_3$, $R_4$, $R_5$, $R_6$ and $R_7$ are each a hydrogen, a hydroxyl, a sulfhydryl, an alkyl, a halogen, an amino, or a nitro group,
wherein X is a halogen, and
wherein one or more of $R_1$, $R_2$, $R_3$ and $R_4$ contains a radioactive isotope.

25. The method of claim 24, wherein one or more of $R_1$, $R_2$, $R_3$ and $R_4$ is a radioactive isotope.

26. The method of claim 25, wherein one or more of $R_1$, $R_2$, $R_3$ and $R_4$ is $^{125}I$ or $^{131}I$.

27. The method of claim 24, wherein the composition is a pharmaceutical composition further comprising a pharmaceutically acceptable carrier.

* * * * *